(12) United States Patent
Nakamura et al.

(10) Patent No.: US 7,345,156 B2
(45) Date of Patent: Mar. 18, 2008

(54) HEPATOCELLULAR CARCINOMA-RELATED GENES AND POLYPEPTIDES, AND METHOD FOR DETECTING HEPATOCELLULAR CARCINOMAS

(75) Inventors: Yusuke Nakamura, Yokohama (JP); Yoichi Furukawa, Kawasaki (JP)

(73) Assignee: Oncotherapy Science, Incorporated, Kanagawa (JP)

( * ) Notice: Subject to any disclaimer, the term of this patent is extended or adjusted under 35 U.S.C. 154(b) by 327 days.

(21) Appl. No.: 10/490,605

(22) PCT Filed: Sep. 25, 2002

(86) PCT No.: PCT/JP02/09873

§ 371 (c)(1),
(2), (4) Date: Sep. 15, 2004

(87) PCT Pub. No.: WO03/027322

PCT Pub. Date: Apr. 3, 2003

(65) Prior Publication Data

US 2005/0019768 A1 Jan. 27, 2005

Related U.S. Application Data

(60) Provisional application No. 60/324,261, filed on Sep. 25, 2001.

(30) Foreign Application Priority Data

Aug. 23, 2002 (CA) ................................ 2399569

(51) Int. Cl.
*C12P 21/06* (2006.01)
*C07H 21/02* (2006.01)
*C12N 5/00* (2006.01)
(52) U.S. Cl. ..................... 536/23.1; 435/69.1; 435/325
(58) Field of Classification Search ...................... None
See application file for complete search history.

(56) References Cited

U.S. PATENT DOCUMENTS 6,783,961 B1 * 8/2004 Edwards et al. ........... 435/91.1

FOREIGN PATENT DOCUMENTS

| WO | WO 99/39200 | 8/1999 |
|---|---|---|
| WO | WO 00/17355 | 3/2000 |
| WO | WO 00/44900 | 8/2000 |
| WO | WO 03/027143 A2 | 4/2003 |
| WO | WO 03/027143 A3 | 4/2003 |
| WO | WO 03/027322 A2 | 4/2003 |
| WO | WO 03/027322 A3 | 4/2003 |

OTHER PUBLICATIONS

UniProt 7.2 data base.*
Carninci et al., Genome research, vol. 10, 1617-1630, 2000.*
Database, N-Geneseq-200701, accession No. AAA08583.*
EST database Accession No. BE747972 , Sep. 15, 2000.*
Edwards et al., EP 1033401A2, date of publication, Sep. 6, 2000.*
Verma et al., Nature, 1997, vol. 389, pp. 239-242.*
Eck et al., Gene-Based Therapy, In: The Pharmacological Basis of Therapeutics, Goodman and Gilman, Ed.s, 1996, pp. 77-101.*
Orkin et al., Report and Recommendation of the Panel to Assess the NIH Investment in Research on Gene Therapy, NIH, 1995.*
Ansieau, et al., *J. Biol. Chem.*, 277(7):4906-4910 (2002).
Aratani, et al., *Mol. Cell. Biol.*, 21(14):4460-4469 (2001).
Brummelkamp, et al., *Science*, 296(5567):550-553 (2002).
Cerione, et al., *Curr. Opin. Cell Biol.*, 8(2):216-222 (1996).
Chardin, et al., *Nature*, 384(6608):481-484 (1996).
Choi, et al., *Cancer*, 79(10):1879-1883 (1997).
Cukierman, et al., *Science*, 270(5244):1999-2002 (1995).
Database EMBL Accession No. AK000206, Feb. 22, 2000.
Database EMBL Accession No. BG773806, May 16, 2001.
Delwel, et al., *Mol. Cell. Biol.*, 13(7):4291-4300 (1993).
Elbashir, et al., *Nature*, 411(6836):494-498 (2001).
EMBL Accession No. AL557360, Feb. 11, 2001.
Fu, et al., *J. Virol.*, 67(12):6965-6972 (1993).
Gelmetti, et al., *Mol. Cell. Biol.*, 8(12):7185-7191 (1998).
Ghanem, et al., *Cancer*, 92(12):3120-3129 (2001).
Golub, et al., *Science*, 286(5439):531-537 (1999).
Gross, et al., *EMBO J.*, 15(8):1961-1870 (1996).
Hamamoto, et al., *Proceedings of the Am. Assoc. for Cancer Res. Annual*, 43:13(#63), and English translation, (2002).
Hamamoto, et al., *94th Annual Mtg. Of the Am. Assoc. for Cancer Res.*, 44:54(#236), and English translation, (2003).
Hamamoto, et al., *94th Annual Mtg. Of the Am. Assoc. for Cancer Res.*, 44(Second Edition):47(#236), and English translation, (2003).
Hamamoto, et al., *Jpn. J. Cancer Res.*, 92(Supplement):117(#208), and English translation, (2001).
Hamamoto, et al., *Jpn. J. Cancer Res.*, 93(Supplement):78(#2032), and English translation, (2002).
Hamamoto, et al., *Jpn. J. Cancer Res.*, 286(#3339-OP), and English translation, (2003).

(Continued)

*Primary Examiner*—Shanon Foley
*Assistant Examiner*—Lei Yao
(74) *Attorney, Agent, or Firm*—Mintz, Levin, Cohn, Ferris, Glovsky and Popeo, P.C.; Ingrid A. Beattie; Cynthia A. Kozakiewicz

(57) ABSTRACT

Genes up-regulated in hepatocellular carcinomas and polypeptides encoded by these genes are provided. Vectors, transformants and methods for producing the recombinant polypeptides are also provided. Probes and primers of these genes and antibodies against the polypeptides are also provided. The probes, primers and antibodies can be used as reagents for detecting hepatocellular carcinomas. Methods for detecting hepatocellular carcinomas using such detection reagents are further provided. Antisense nucleolide sequences of these genes are also provided and can be used to inhibit growth of hepatocellular carcinomas.

5 Claims, 14 Drawing Sheets

OTHER PUBLICATIONS

Hamamoto, et al., *Jpn Assoc. Mol. Target Ther. Cancer*, 36(#SY-1), and English translation, (2002).
Hammond, et al., *Nature*, 404(6775):293-296 (2000).
Hannon, et al., *Nature*, 418(6894):244-251 (2002).
Herbst, et al., *Cancer*, 94(5):1593-1611 (2002).
Hermouet, et al., *Proc. Natl. Acad. Sci. USA*, 88(23):10455-10459 (1991).
Ito, et al., *Br. J. Cancer*, 84(10):1377-1383 (2001).
Jackson, et al., *Trends Biochem. Sci.*, 25(10):489-495 (2000).
Kato, et al., *Jpn. J. Cancer Res.*, 93(Supplement):78(2033), and English translation, (2002).
Kibar, et al., *Nat. Genet.*, 28(3):251-255 (2001).
Lüking, et al., *Crit. Rev. Biochem. Mol. Biol.*, 33(4):259-296 (1998).
Lutterbach, et al., *Mol. Cell. Biol.*, 18(12):7176-7184 (1998).
Lyons, et al., *Science*, 249(4969):655-659 (1990).
Masselink, et al., *Oncogene*, 19(12):1538-1546 (2000).
Mendelsohn, et al., *Oncogene*, 19(56):6550-6565 (2000).
Miyagishi, et al., *Nat. Biotechnol.*, 19:497-500 (2002).
Miyaki, et al., *Int. J. Cancer*, 85(4):518-522 (2000).
Mochizuki, et al., *Gene*, 181(1-2):39-43 (1996).
Moss, et al., *J. Biol. Chem.*, 270(21):12327-12330 (1995).
Nakajima, et al., *Cell*, 90(6):1107-1112 (1997).
Okabe, et al., *Cancer Res.*, 61(5):2129-2137 (2001).
Pace, et al., *Proc. Natl. Acad. Sci. USA*, 88(16):7031-7035 (1991).
Perou, et al., *Nature*, 406(6797):747-752 (200).
Randazzo, et al., *Proc. Natl. Acad. Sci. USA*, 97(8):4011-4016 (2000).
Sharp, P.A., *Genes Dev.*, 13(2):139-141 (1999).
Tanaka, et al., *Biochim. Biophys. Acta*, 1536(1):1-12 (2001).
Tang, et al., *Mol. Cell. Biol.*, 19(5):3540-3550 (1999).
Tanner, et al., *Mol. Cell*, 8(2):251-262 (2001).
von Marschall, et al., *Gut*, 48(1):87-96 (2001).
Westermarck, et al., *EMBO J.*, 21(3):451-460 (2002).
Wolff, et al., *Development*, 125(6):1149-1159 (1998).
Yagyu, et al., *Jpn. J. Cancer Res.*, 92(Supplement):118(209), and English translation, (2001).
Yagyu, et al., *Int. J. Oncol.*, 20(6):1173-1178 (2002).
Ying, et al., *Biochem. Biophys. Res. Commun.*, 286(2):394-400 (2001).
EMBL Accession No. AK024733, Sep. 29, 2000.

* cited by examiner

HEPATOCELLULAR CARCINOMA-RELATED GENES AND POLYPEPTIDES, AND METHOD FOR DETECTING HEPATOCELLULAR CARCINOMAS

RELATED APPLICATIONS

This application is a national stage application, filed under 35 U.S.C. §371, of International Application No. PCT/JP02/09873, filed on Sep. 25, 2002, which claims the benefit of Canadian Patent Application 2,399,569, filed Aug. 23, 2002 and U.S. Ser. No. 60/324,261, filed Sep. 25, 2001.

TECHNICAL FIELD

The present invention relates to genes up-regulated in hepatocellular carcinomas, polypeptides encoded by the genes, and a method for detecting hepatocellular carcinomas.

BACKGROUND ART cDNA microarray technologies have enabled one to obtain comprehensive profiles of gene expression in normal versus malignant cells (Perou, C. M. et al., Nature. 406: 747-752, 2000; Clark, E. A. et al., Nature. 406: 532-535, 2000; Okabe, H. et al., Cancer Res. 61: 2129-2137, 2001). This approach discloses the complex nature of cancer cells, and helps to improve understanding of carcinogenesis. Identification of genes that are deregulated in tumors can lead to more precise and accurate diagnosis of individual cancers, and to development of novel therapeutic targets (Golub, T. R. et al., Science 286: 531-537, 1999).

Hepatocellular carcinoma (HCC) is a leading cause of cancer deaths worldwide. In spite of recent progress in therapeutic strategies, prognosis of patients with advanced HCC remains very poor. Although molecular studies have revealed that alterations of TP53, CTNNB1 and/or AXIN1 genes can be involved in hepatocarcinogenesis (Perou, C. M. et al., Nature. 406: 747-752, 2000; Satoh, S. et al., Nat Genet. 24: 245-250, 2000), these changes appear to be implicated in only a fraction of HCCs. Accordingly, a ultimate gene that can be a novel diagnostic marker and/or drug target for treatment of cancers has been desired.

The present inventors previously reported that a novel gene, VANGL1, was identified by genome-wide analysis of HCCs (Yagyu, R. et al., International Journal of Oncology 20: 1173-1178, 2002).

DISCLOSURE OF THE INVENTION

An objective of the present invention is to provide genes up-regulated in hepatocellular carcinomas, polypeptides encoded by the genes, and a method for detecting hepatocellular carcinomas.

The present inventors have analyzed expression profiles of HCCs by means of a cDNA micro array representing 23,040 genes. These efforts have pinpointed 165 genes, including 69 ESTs, which appear to be up-regulated frequently in cancer tissues compared with corresponding non-cancerous liver cells. The inventors isolated three genes from among the transcripts whose expression was frequently elevated in HCCs. These genes encode products that shared structural features with centaurin-family proteins.

One of the three genes corresponds to an EST, Hs.44579 of a UniGene cluster, and was found to be a novel gene over-expressed at chromosomal band 1p36.13. Since an open reading frame of this gene encoded a protein approximately 60% identical to that of development and differentiation enhancing factor 2 (DDEF2), the inventors termed this gene development and differentiation enhancing factor-like 1 (DDEFL1).

Another gene up-regulated in HCCs corresponds to an EST (Hs. 122730) of a UniGene cluster. The predicted amino acid sequence shared 40% and 63% identity with *strabismus* (Van Gogh), which is involved in cell polarity and cell fate decisions in *Drosophila*, and Van Gogh Like 2 (VANGL2). Hence, this gene was termed Van Gogh Like 1 (VANGL1).

Another gene up-regulated in HCCs was found to be LGN (GenBank accession number U54999). LGN protein interacts with alpha subunit of inhibitory heterotrimeric G proteinis ($G\alpha_{i2}$).

Gene transfer of DDEFL1 or LGN promoted proliferation of cells that lacked endogenous expression of either of these genes. Furthermore, reduction of DDEFL1, VANGL1 or LGN expression by transfection of their specific anti-sense S-oligonucleotides inhibited the growth of hepatocellular carcinoma cells.

The above findings would contribute to clarify the mechanisms of HCC and to develop new strategies for diagnosis and treatment of HCC.

The present invention specifically provides (1) an isolated nucleic acid selected from the group consisting of:

(a) a nucleic acid comprising the nucleotide sequence of SEQ ID NO: 1 or NO: 3;

(b) a nucleic acid encoding a polypeptide comprising the amino acid sequence of SEQ ID NO: 2 or NO: 4;

(c) a nucleic acid comprising a strand that hybridizes under high stringent conditions to a nucleotide sequence consisting of SEQ ID NO: 1 or NO: 3 or the complement thereof, (2) an isolated polypeptide selected from the group consisting of:

(a) a polypeptide encoded by the nucleotide sequence of SEQ ID NO: 1 or NO: 3;

(b) a polypeptide comprising the amino acid sequence of SEQ ID NO: 2 or NO: 4;

(c) a polypeptide having at least 65% identity to SEQ ID NO: 2 or NO: 4, (3) a vector carrying the nucleic acid of (1), (4) a transformant carrying the nucleic acid of (1) or the vector of (3), (5) a method of producing a polypeptide, the method comprising culturing the transformant of (4) in a culture, expressing the polypeptide in the transformant, and recovering the polypeptide from the culture, (6) an antibody that specifically binds to the polypeptide of (2), (7) a method for detecting hepatoceullar carcinoma, the method comprising the steps of:

(a) preparing a biological sample from a subject, (b) measuring the expression level of at least one of polypeptides selected from the group consisting of the polypeptide of SEQ ID NO: 1, a polypeptide of SEQ ID NO: 3, and the polypeptide of SEQ ID NO: 5;

(c) comparing the expression level with that measured in a non-cancerous sample; and (d) determining the presence or absence of the cancer in the subject, (8) a reagent for detecting hepatocellular carcinomas, comprising a nucleic acid comprising a strand that hybridizes under high stringent conditions to a nucleotide sequence cosisting of SEQ ID NO: 1, NO: 3, or NO: 5 or the complement thereof, (9) a reagent for detecting hepatocellular carcinomas, comprising the antibody of (6), and

(10) a method for inhibiting growth of hepatocellular carcinomas, the method comprising introducing at least one of antisense oligonucleotides that hybridizes with the nucleotide sequence of SEQ ID NO: 1, NO: 3, or NO: 5 into hepatocelluar carcinomas.

The present invention will be illustrated below in more detail.

Nucleic Acids

The present invention provides genes up-regulated in hepatocellular carcinomas.

The nucleotide sequence and the amino acid sequence of DDEFL1 are shown as SEQ ID NO: 1 and NO: 2, respectively. The complete cDNA of DDEFL1 consisted of 4050 nucleotides, with an open reading frame of 2712 uncleotides encoding a 903-amino-acid protein (GenBank accession number AB051853). The amino acid sequence of DDFEL1 showed 60% identity to DDEFL2 and 46% identity to DDEF/ASAP1, and contained an Arf GTPase-activating protein (ArfGAP) domain and two ankyrin repeats.

DDEFL1 showed 60% identity to a member of the centaurin family, DDEF2, a protein that regulates re-organization. of the actin cytoskeleton. This suggests that DDEFL1 may also play a role in organization of cellular structure (Randazzo, P. A. et al., The Arf GTPase-activating protein ASAP1 regulates the actin cytoskeleton, Proc. Natl. Acad. Sci. USA 97: 4011-4016, 2000). Because DDEFL1 also conserves a PH domain and an ArfGAP motif it appears to be a new member of the centaurin family, regulating Arf small GTPase by means of GAP activity. The PH domain, observed in the majority of molecules belonging to the Dbl family of GEFs, is thought to play a crucial role in relocation of proteins by interacting with specific target molecules and/or by directly regulating catalytic domains (Jackson, T. R. et al., Trends Biochem Sci. 25: 489-495, 2000; Cerione, R. A. and Zheng, Y., Curr. Opin. Cell. Biol. 8: 216-222, 1996; Chardin, P. et al., Nature 384: 481-484, 1996). Although DDEF2 is localized in peripheral focal adhesions, the inventors found myc-tagged DDEFL1 protein to be diffuse in cytoplasm.

Arf proteins have been implicated in important cellular processes such as vesicular membrane transport, maintenance of the integrity of ER and Golgi compartments, and regulation of the peripheral cytoskeleton (Cukierman, E. et al., Science 270: 1999-2002, 1995). Six members of Arf family (Arf1-Arf6) and their functions have been identified so far (Moss, J. and Vaughan, M., J. Biol. Chem. 270: 12327-12330, 1995). For example, Arf6 proteins have been implicated as regulators of the cytoskeleton to alter the morphology of focal adhesions and to block spreading of cells, and DDEF2 displays GAP activity toward Arf1.

Over-expression of DDEFL1 promoted growth promotion and survival of cells under low-serum conditions. This suggests that DDEFL1 may provide a growth advantage to cancer cells in poor nutritional and hypoxic conditions. The frequent up-regulation of DDEFL1 in HCCs underscores the importance of this gene in hepatocarcinogenesis.

The nucleotide sequence and the amino acid sequence of VANGL1 are shown as SEQ ID NO: 3 and NO: 4, respectively. The determined cDNA sequence consisted of 1879 nucleotides containing an open reading frame of 1572 nucleotides encoding a 524-amino-acid protein (GenBank accession number AB057596).

*Strabismus* (stbm) was identified as a gene responsible for a mutant fruit fly with rough eye phenotype (Wolff T. and Rubin G. M., Development 125:1149-1159, 1998). The gene is required to maintain polarity in the eye, legs and bristles and to decide cell fate of R3 and R4 photoreceptors in the *Drosophila*. A mouse gene homologous to stbm, Ltap, was altered in the neural tube mutant mouse Loop-tail, which is a human model of neural tube defects (NTDs) (Kibar Z et al., Nat Genet. 28: 251-255, 2001). Hence, VANGL1 may also play important roles in cellular polarity, cell fate decision, and/or organization of tissues. Since VANGL1 is frequently up-regulated in HCCs and suppression of its expression significantly reduced growth or survival of cancer cells, VANGL1 may confer prolonged survival and/or depolarized growth to cancer cells.

The nucleotide sequence and the amino acid sequence of LGN are shown as SEQ ID NO: 5 and NO: 6, respectively. LGN cDNA consists of 2336 nucleotides and encodes a 677 amino acid peptide.

LGN protein was previously reported as a protein interacting with alpha subunit of inhibitory heterotrimeric G proteins (Gαi2) (Mochizuki, N. et al., Gene 181: 39-43, 1996). The activating mutations of Gαi2 have ever been reported in pituitary tumor and other endocrine tumors (Hermouet, S. et al., Proc. Natl. Acad. Sci. USA 88: 10455-10459, 1991; Pace, A. M. et al., Proc. Natl. Acad. Sci. USA. 88: 7031-7035, 1991; Lyons, J. et al, Science 249: 655-659, 1990). However, involvement of LGN in tumorigenesis or carcinogenesis has not yet been reported. Colony formation assay suggested that LGN might have oncogenic activity. Enhanced expression of LGN may activate Gαi2 and mediate oncogenic signals in hepatocarcinogenesis.

The nucleic acid of the present invention includes cDNA, genomic DNA, chemically synthesized DNA, and RNA It may be single-stranded or double-stranded.

The "isolated nucleic acid" used herein means a nucleic acid the structure of which is not identical to that of any naturally occurring nucleic acid or to that of any fragment of a naturally occurring genomic nucleic acid spanning more than three separate genes. The term therefore includes, for example, (a) a DNA which has the sequence of part of a naturally occurring genomic DNA molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids of DNA molecules present in mixtures of different (i) DNA molecules, (ii) transfected cells, or (iii) cell clones; e.g., as these occur in a DNA library such as a cDNA or genomic DNA library.

In one embodiment, the nucleic acid of the present invention includes a nucleic acid comprising the nucleotide sequence of DDEFL1 or VANGL1, specifically SEQ ID NO: 1 or NO: 3.

In another embodiment, the nucleic acid of the present invention includes a nucleic acid encoding a polypeptide comprising the amino acid sequence of DDEFL1 or VANGL1, specifically, SEQ ID NO: 2 or NO: 4. Thus, the nucleic acid comprising arbitrary sequences based on the degeneracy of the genetic code are included.

In still another embodiment, the nucleic acid of the present invention includes a variant nucleic acid of SEQ ID NO: 1 or NO: 3. The variant includes a nucleic acid comprising a strand that hybridizes under high stringent conditions to a nucleotide sequence consisting of SEQ ID NO: 1 or NO: 3 or the complement thereof.

The term "complement" used herein means one strand of a double-stranded nucleic acid, in which all the bases are able to form base pairs with a sequence of bases in another strand. Also, complementary is defined as not only those completely matching within a continuous region of at least 15 contiguous nucleotides, but also those having identity of at least 65%, preferably 70%, more preferably 80%, still more preferably 90%, and most preferably 95% or higher within that region.

As used herein, "percent identity" of two nucleic acids is determined using the algorithm of Karlin and Altschul (Proc. Natl. Acad. Sci. USA 87: 2264-2268, 1990) modified as in Karlin and Altschul (Proc. Natl. Acad. Sci. USA 90:5873-5877, 1993). Such an algorithm is incorporated into the NBLAST and XBLAST programs of Altschul et al. (J. Mol. Biol. 215:403-410, 1990). BLAST nucleotide searches are performed with the NBLAST program, score=100, wordlength=12. Homology search of protein can readily be performed, for example, in DNA Databank of JAPAN (DDBJ), by using the FASTA program, BLAST program, etc. BLAST protein searches are performed with the XBLAST program, score=50, wordlength=3. Where gaps exist between two sequences, Gapped BLAST is utilized as described in Altsuchletal. (Nucleic Acids Res. 25: 3389-3402, 1997). When utilizing BLAST and Gapped BLAST programs, the default parameters of the respective programs (e.g, XBLAST and NBLAST) are used.

Preferably, the variant includes a nucleotide sequence that is at least 65% identical to the nucleotide sequence shown in SEQ ID NO: 1 or NO: 3. More preferably, the variant is at least 65%, 70%, 75%, 80%, 85%, 90%, 95%, 96%, 97%, 98%, 99%, or more, identical to the nucleotide sequence shown in SEQ ID NO: 1 or NO: 3. In the case of a variant which is longer than or equivalent in length to the reference sequence, e.g., SEQ ID NO: 1 or NO: 3, the comparison is made with the full length of the reference sequence. Where the variant is shorter than the reference sequence, e.g., shorter than SEQ ID NO: 1 or NO: 3, the comparison is made to segment of the reference sequence of the same length (excluding any loop required by the homology calculation).

The stringency of hybridization is defined as equilibrium hybridization under the following conditions: 42° C., 2×SSC, 0.1% SDS (low stringency); 50° C., 2×SSC, 0.1% SDS (medium stringency); and 65° C., 2×SSC, 0,1% SDS (high stringency). If washings are necessary to achieve equilibrium, the washings are performed with the hybridization solution for the particular stringency desired. In general, the higher the temperature, the higher is the homology between two strands hybridizing at equilibrium.

There is no restriction on length of the nucleic acid of the present invention, but it preferably comprises at least 15, 20, 30, 40, 50, 100, 150, 200, 300, 400, 500, 1000, 1500, 2000, 2500, or 3000 nucleotides.

The nucleic acid of the present invention includes polynucleotides used as probes or primers specifically hybridizing with the nucleotide sequence of SEQ ID NO: 1 or NO: 3 or its complement. The term "specifically hybridizing" means that hybridizing under a normal hybridization condition, preferably a stringent condition with the nucleotide sequence of SEQ ID NO: 1 or NO: 3, but not crosshybridizing with DNAs encoding other polypeptides.

The primers and probes comprise at least 15 continuous nucleotides within the nucleotide sequence of SEQ ID NO: 1 or 3 or complementary to the sequence. In general, the primers comprises 15 to 100 nucleotides, and preferably 15 to 35 nucleotides, and the probes comprise at least 15 nucleotides, preferably at least 30 nucleotides, containing at least a portion or the whole sequence of SEQ ID NO: 1 or NO: 3. The primers can be used for amplification of the nucleic acid encoding the polypeptide of the present invention and the probes can be used for the isolation or detection of the nucleic acid encoding the polypeptide of the present invention. The primers and probes of the present invention can be prepared, for example, by a commercially available oligonucleotide synthesizing machine. The probes can be also prepared as double-stranded DNA fragments which are obtained by restriction enzyme treatments and the like.

The nucleic acid of the present invention includes an antisense oligonucleotide that hybridizes with any site within the nucleotide sequence of SEQ ID NO: 1 or 3. The term "antisense oligonucleotides" as used herein means, not only those in which the entire nucleotides corresponding to those constituting a specified region of a DNA or mRNA are complementary, but also those having a mismatch of one or more nucleotides, as long as DNA or mRNA and an oligonucleotide can specifically hybridize with the nucleotide sequence of SEQ ID NO: 1 or NO: 3.

The antisense oligonucleotide is preferably that against at least 15 continuous nucleotides in the nucleotide sequence of SEQ ID NO: 1 or NO: 3. The above-mentioned antisense oligonucleotide, which contains an initiation codon in the above-mentioned at least 15 continuous nucleotides, is even more preferred.

The antisense oligonucleotides of the present invention includes analogs containing lower alkyl phosphonate (e.g., methyl-phosphonate or ethyl-phosphonate), phosphothioate, and phosphoamidate.

The antisense oligonucleotide of the present invention, acts upon cells producing the polypeptide of the invention by binding to the DNA or mRNA encoding the polypeptide and inhibits its transcription or translation, promotes the degradation of the mRNA, inhibiting the expression of the polypeptide of the invention.

The nucleic acid of the present invention can be prepared as follows. cDNA encoding the polypeptide of the present invention can be prepared, for example, by preparing a primer based on nucleotide information (for example, SEQ ID NO: 1 or NO: 3) of DNA encoding the polypeptide of the present invention and performing plaque PCR (Affara NA et al. (1994) Genomics 22, 205-210). Genomic DNA can be prepared, for example, by the method using commercially available "Qiagen genomic DNA kits" (Qiagen, Hilden, Germany). The nucleotide sequence of the DNA acquired can be decided by ordinary methods in the art by using, for example, the commercially available "dye terminator sequencing kit" (Applied Biosystems). The nucleic acid of the present invention, as stated later, can be utilized for the production of a recombinant protein and detection of hepatocellular carcinoma.

Vectors, Transformants, and Production of Recombinant Polypeptide

The present invention also features a vector into which the nucleic acid of the present invention has been inserted.

The vector of the present invention includes a vector. for preparing the recombinant polypeptide of the present invention. Any vector can be used as long as it enables expression of the polypeptide of the present invention.

Examples of the expression vector include bacterial (e.g. *Escherichia coli*) expression vectors, yeast expression vectors, insect expression vectors, and mammalian expression vectors. In the present invention, mammalian expression vectors such as pcDNA3.1-myc/His or pcDNA 3.1 vector (Invitrogen) can be used. Insertion of the nucleic acid of the present invention into a vector can be done using ordinary methods in the art.

The vector of the present invention also includes a vector for expressing the polypeptide of the present invention in vivo (especially for gene therapy). Various viral vectors and non-viral vectors can be used as long as they enable expression of the polypeptide of the present invention in vivo. Examples of viral vectors are adenovirus vectors, retrovirus vectors, etc. Cationic liposomes can be given as examples of non-viral vectors.

The present invention also provides a transformant carrying, in an expressible manner, the nucleic acid of the present invention. The transformant of the present invention includes, those carrying the above-mentioned expression vector into which nucleic acid of the present invention has been inserted, and those having host genomes into which the nucleic acid of the present invention has been integrated. The nucleic acid of the invention is retained in the transformant in any form as long as the transformant can express the nucleic acid.

There is no particular restriction as to the cells into which the vector is inserted as long as the vector can function in the cells to express the nucleic acid of the present invention. For example, *E. coli*, yeast, mammalian cells and insect cells can be used as hosts. Preferably, mammalian cells such as COS7 cells and NIH3T3 cells. Introduction of a vector into a cell can be done using known methods such as electroporation and calcium phosphate method.

Common methods applied in the art may be used to isolate and purify said recombinant polypeptide from the transformant. For example, after collecting the transformant and obtaining the extracts, the objective polypeptide can be purified and prepared by, ion exchange chromatography, reverse phase chromatography, gel filtration, or affinity chromatography where an antibody against the polypeptide of the present invention has been immobilized in the column, or by combining several of these columns.

Also when the polypeptide of the present invention is expressed within host cells (for example, animal cells, *E. coli*) as a fusion protein with glutathione-S-transferase protein or as a recombinant polypeptide supplemented with multiple histidines, the expressed recombinant polypeptide can be purified using a glutathione column or nickel column. After purifying the fusion protein, it is also possible to exclude regions other than the objective polypeptide by cutting with thrombin or factor-Xa as required.

Polypeptides

The present invention provides isolated polypeptides encoded by DDEFL1 or VANGL1 (e.g. SEQ ID NO: 1 or NO: 3). In specific embodiments, the polypeptides of the present invention includes a polypeptide encoded by the nucleotide sequence of SEQ ID NO: 1 or NO: 3 and a polypeptide comprising the amino acid sequence of SEQ ID NO: 2 or NO: 4.

The "isolated polypeptide" used here in means a polypeptide that is substantially pure and free from other biological macromolecules. The substantially pure polypeptide is at least 75% (e.g., at least 80, 85, 95, or 99%) pure by dry weight. Purity can be measured by any appropriate standard method, for example by column chromatography, polyacrylamide gel electrophoresis, or HPLC analysis.

The polypeptide of the present invention includes variants of SEQ ID NO: 2 or NO: 4 as long as the variants are at least 65% identical to SEQ ID NO: 2 or NO: 4. The variants may be a polypeptide comprising the amino acid sequence of SEQ ID NO: 2 or NO: 4 in which one or more amino acids have been substituted, deleted, added, and/or inserted. The variants may also be a polypeptide encoded by a nucleic acid comprising a strand that hybridizes under high stringent conditions to a nucleotide sequence consisting of SEQ ID NO: 1 or NO: 3.

Polypeptides having amino acid sequences modified by deleting, adding and/or replacing one or more amino acid residues of a certain amino acid sequence, have been known to retain the original biological activity (Mark, D. F. et al., Proc. Natl. Acad. Sci. USA (1984) 81, 5662-5666, Zoller, M. J. & Smith, M., Nucleic Acids Research (1982) 10, 6487-6500, Wang, A. et al., Science 224, 1431-1433, Dalbadie-McFarland, G. et al., Proc. Natl. Acad. Sci. USA (1982) 79, 6409-6413).

The number of amino acids that are mutated by substitution, deletion, addition, and/or insertion is not particularly restricted. Normally, it is 10% or less, preferably 5% or less, and more preferably 1% or less of the total amino acid residues.

As for the amino acid residue to be mutated, it is preferable to be mutated into a different amino acid in which the properties of the amino acid side-chain are conserved. Examples of properties of amino acid side chains are, hydrophobic amino acids (A, I, L, M, F, P, W, Y, V), hydrophilic amino acids (R, D, N, C, E, Q, G, H, K, S, T), and amino acids comprising the following side chains: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); abase containing side-chain (R, K, H); and an aromatic containing side-chain (H, F, Y, W) (The parenthetic letters indicate the one-letter codes of amino acids). A "conservative amino acid substitution" is a replacement of one amino acid belonging to one of the above groups with another amino acid in the same group.

A deletion variant includes a fragment of the amino acid sequence of SEQ ID NO: 1 or NO: 3. The fragment is a polypeptide having an amino acid sequence which is partly, but not entirely, identical to the above polypeptides of this invention. The polypeptide fragments of this invention usually consist of 8 amino acid residues or more, and preferably 12 amino acid residues or more (for example, 15 amino acid residues or more). Examples of preferred fragments include truncation polypeptides, having amino acid sequences lacking a series of amino acid residues including either the amino terminus or carboxyl terminus, or two series of amino acid residues, one including the amino terminus and the other including the carboxyl terminus. Furthermore, fragments featured by structural or functional characteristics are also preferable, which include those having α-helix and α-helix forming regions, β-sheet and β-sheet forming regions, turn and turn forming regions, coil and coil forming regions, hydrophilic regions, hydrophobic regions, α-amphipathic regions, β-amphipathic regions, variable regions, surface forming regions, substrate-binding regions, and high antigenicity index region. Biologically active fragments are also preferred. Biologically active fragments mediate the activities of the polypeptides of this invention, which fragments include those having similar or improved activities, or reduced undesirable activities. For example, fragments having the activity to transduce signals into cells via binding of a ligand, and furthermore, fragments having antigenicity or immunogenicity in animals, especially humans are included. These polypeptide fragments preferably retain the antigenicity of the polypeptides of this invention.

Further, an addition variant includes a fusion protein of the polypeptide of the present invention and another peptide or polypeptide. Fusion proteins can be made by techniques well known to a person skilled in the art, such as by linking the DNA encoding the polypeptide of the invention with DNA encoding other peptides or polypeptides, so as the frames match, inserting this into an expression vector and expressing it in a host. There is no restriction as to the peptides or polypeptides fused to the polypeptide of the present invention.

Known peptides, for example, FLAG (Hopp, T. P. et al., Biotechnology (1988) 6, 1204-1210), 6×His containing six His (histidine) residues, 10×His, Influenza agglutinin (HA), human c-myc fragment, VSP-GP fragment, p18HIV fragment, T7-tag, HSV-tag, E-tag, SV40T antigen fragment, lck tag, α-tubulin fragment, B-tag, Protein C fragment, and such, can be used as peptides that are fused to the polypeptide of the present invention. Examples of polypeptides that are fused to polypeptide of the invention are, GST (glutathione-S-transferase), Influenza agglutinin (HA), immunoglobulin constant region, β-glactosidase, MBP (maltose-binding protein), and such.

Fusion proteins can be prepared by fusing commercially available DNA encoding these peptides or polypeptides with the DNA encoding the polypeptide of the present invention and expressing the fused DNA prepared.

The variant polypeptide is preferably at least 65% identical to the amino acid sequence shown in SEQ ID NO: 2 or NO: 4. More specifically, the modified polypeptide is at least 65%, 70%, 75%, 80%, 85%, 90%, 95%, 96%, 97%, 98%, 99%, or more, identical to the amino acid sequence shown in SEQ ID NO: 2 or NO: 4. In the case of a modified polypeptide which is longer than or equivalent in length to the reference sequence, e.g., SEQ ID NO: 2 or NO: 4, the comparison is made with the full length of the reference sequence. Where the modified polypeptide is shorter than the reference sequence, e.g., shorter than SEQ ID NO: 2 or NO: 4, the comparison is made to segment of the reference sequence of the same length.

As used herein, "percent identity" of two amino acid sequences is determined in the same manner as described above for the nucleic acids.

The polypeptide of the present invention can be prepared by methods known to one skilled in the art, as a natural polypeptide or a recombinant polypeptide made using genetic engineering techniques as described above. For example, a natural polypeptide can be obtained by preparing a column coupled with an antibody obtained by immunizing a small animal with the recombinant polypeptide, and performing affinity chromatography for extracts of liver tissues or cells expressing high levels of the polypeptide of the present invention. A recombinant polypeptide can be prepared by inserting DNA encoding the polypeptide of the present invention (for example, DNA comprising the nucleotide sequence of SEQ ID NO: 1 or 3) into a suitable expression vector, introducing the vector into a host cell, allowing the resulting transformant to express the polypeptide, and recovering the expressed polypeptide.

The variant polypeptide can be prepared, for example, by inserting a mutation into the amino acid sequence of SEQ ID NO: 1 or NO: 3 by a known method such as the PCR-mediated, site-directed-mutation-induction system (GIBCO-BRL, Gaithersburg, Md.), oligonucleotide-mediated, sight-directed-mutagenesis (Kramer, W. and Fritz, H J (1987) Methods in Enzymol. 154:350-367).

Antibodies

The present invention also features an antibody that specifically binds to the polypeptide of the present invention. There is no particular restriction as to the form of the antibody of the present invention and include polyclonal antibodies and monoclonal antibodies. The antiserum obtained by immunizing animals such as rabbits with the polypeptide of the present invention, polyclonal and monoclonal antibodies of all classes, humanized antibodies made by genetic engineering, human antibodies, are also included.

Polyclonal antibodies can be made by, obtaining the serum of small animals such as rabbits immunized with the polypeptide of the present invention, attaining a fraction recognizing only the polypeptide of the invention by an affinity column coupled with the polypeptide of the present invention, and purifying immunoglobulin G or M from this fraction by a protein G or protein A column.

Monoclonal antibodies can be made by immunizing small animals such as mice with the polypeptide of the present invention, excising the spleen from the animal, homogenizing the organ into cells, fusing the cells with mouse myeloma cells using a reagent such as polyethylene glycol, selecting clones that produce antibodies against the polypeptide of the invention from the fused cells (hybridomas), transplanting the obtained hybridomas into the abdominal cavity of a mouse, and extracting ascites. The obtained monoclonal antibodies can be purified by, for example, ammonium sulfate precipitation, protein A or protein G column, DEAE ion exchange chromatography, or an affinity column to which the polypeptide of the present invention is coupled. The antibody of the invention can be used for purifying and detecting the polypeptide of the invention. In particular, it can be used for detecting hepatocellular carcinoma.

The human antibodies or humanized antibodies can be prepared by methods commonly known to one skilled in the art. For example, human antibodies can be made by, immunizing a mouse whose immune system has been changed to that of humans, with the polypeptide of the present invention. Also, humanized antibodies can be prepared by, for example, cloning the antibody gene from monoclonal antibody producing cells and using the CDR graft method which transplants the antigen-recognition site of the gene into a known human antibody.

Detection Methods

The present invention further provides a method of detecting hepatocellular carcinoma using the DDEFL1, VANGL1, or LGN polypeptide as a marker.

The detection can be performed by measuring an expression level of at least one of DDEFL1, VANGL1, and LGN polypeptides in a biological sample from a subject, comparing the expression level with that in a non-cancerous sample, and determining the presence or absence of the cancer in a subject.

A biological sample used herein include any liver tissues or cells obtained from a subject who is in need of detection of hepatocellular carcinoma. In particular, liver biopsy specimen can be used. The biological sample also includes an mRNA, cRNA or cDNA sample prepared from liver tissues or cells. mRNA and cDNA samples can be prepared by a conventional method. cRNA refers to RNA transcribed from a template cDNA with RNA polymerase. cRNA can be synthesized from T7promoter-attached cDNA as a template by using T7 RNA polymerase. A commercially available cRNA transcription kit for DNA chip-based expression profiling can be used.

In specific embodiments, the expression level of DDEFL1, VANGL1 or LGN polypeptide can be measured in the RNA, cDNA, or polypeptide level.

The mRNA expression level can be measured by, for example, a Northern blotting method using a probe that hybridizes with the nucleotide sequence of DDEFL1, VANGL1, or LGN, an RT-PCR method using a primer that hybridizes with the nucleotide sequence of DDEFL1, VANGL1, or LGN, and such.

The probes or primers used in the detection method of the present invention include a nucleic acid specifically hybridizing with the nucleotide sequence of SEQ ID NO: 1, NO: 3, or NO: 5, or its complement. The term "specifically hybridizing" means that hybridizing under a normal hybridization condition, preferably a stringent condition with the nucleotide sequence of SEQ ID NO: 1, NO: 3, or NO: 5, but not crosshybridizing with DNAs encoding other polypeptides.

The primers and probes comprise at least 15 continuous nucleotides within the nucleotide sequence of SEQ ID NO: 1, NO: 3, or NO: 5 or complementary to the sequence. In general, the primers comprises 15 to 100 nucleotides, and preferably 15 to 35 nucleotides, and the probes comprise at least 15 nucleotides, preferably at least 30 nucleotides, containing at least a portion or the whole sequence of SEQ ID NO: 1, NO: 3, or NO: 5. The primers and probes can be prepared, for example, by a commercially available oligonucleotide synthesizing machine. The probes can be also prepared as double-stranded DNA fragments which are obtained by restriction enzyme treatments and the like.

The cDNA expression level can be measured by, for example, a method utilizing a DNA array (Masami Muramatsu and Masashi Yamamoto, New Genetic Engineering Handbook pp.280-284, YODOSHA Co., LTD.). Specifically, first, a cDNA sample prepared from a subject and a solid support, on which polynucleotide probes hybridizing with the nucleotide sequence of DDEFL1, VANGL1, or LGN are fixed, are provided. As the probes, those as described above can be used. Plural kinds of probes can be fixed on the solid support in order to detect plural kinds of target polynucleotides. The cDNA sample is labeled for detection according to needs. The label is not specifically limited so long as it can be detected, and includes, for example, fluorescent labels, radioactive labels, and so on. The labeling can be carried out by conventional methods (L. Luo et al., "Gene expression profiles of laser-captured adjacent neuronal subtypes", Nat. Med. (1999) pp. 117-122).

The cDNA sample is then contacted with the probes on the solid support to allow the cDNA sample to hybridize with the probes. Although the reaction solution and the reaction condition for hybridization varies depending on various factors, such as the length of the probe, they can be determined according to usual methods well known to those skilled in the art.

The intensity of hybridization between the cDNA sample and the probes on the solid support is measured depending on the kind of the label of the cDNA sample. For example, a fluorescent label can be detected by reading out the fluorescent signal with a scanner.

The hybridization intensity of the test cDNA sample and the control cDNA sample (e.g. cDNA from non-cancerous tissues or cells) can be measured simultaneously in one measurement by labeling them with different fluorescent labels. For example, one of the above-mentioned cDNA samples can be labeled with Cy5, and the other with Cy3. The intensity of Cy5 and Cy3 fluorescent signals show the expression level of the respective cDNA samples (Duggan et al., Nat. Genet. 21:10-14, 1999).

In this method, cRNA can be measured in place of cDNA.

Furthermore, the polypeptide expression level can be measured using an antibody against DDEFL1, VANGL1, or LGN polypeptide by, for example, SDS polyacrylamide electrophoresis, Western blotting, dot-blotting, immunoassay such as immunoprecipitation, fluoroimmunoassay, radioimmunoassay, enzyme immunoassay (e.g. enzyme-linked immunosorbent assay (ELISA)), and immunohistochemical staining, etc.

In specific embodiments, a biological sample is contacted with an antibody against DDEFL1, VANGL1, or LGN polypeptide immobilized on a solid support, the antibody-antigen complex on the solid support is contacted with a second antibody labeled with a detectable label, and the label is detected by an appropriate method.

The antibody used in the detection method of the present invention includes any antibody that binds to the DDEFL1, VANGL1, or LGN polypeptide, specifically the polypeptide with the amino acid sequence of SEQ ID NO: 2, NO: 4, or NO: 6, including antiserum obtained by immunizing animals such as rabbits with the DDEFL1, VANGL1, or LGN polypeptide, polyclonal and monoclonal antibodies of all classes, humanized antibodies made by genetic engineering, and human antibodies. These antibodies can be prepared as described above.

The expression level measured as described above is compared with that measured in a non-cancerous sample to determine the presence or absence of hematocellular carcinoma in the subject. When the expression level measured in the sample from the subject is higher than that measured in the non-cancerous sample, the subject is judged to have the cancer or the risk of the cancer. On the other hand, the expression level in the subject sample is not higher compared with that in the non-cancerous sample, then, the subject is judged to be free from the cancer. Specifically, whether the expression level in the subject sample is higher than that in the non-cancerous sample, can be determined based on the relative expression ratio (subject sample/non-cancerous sample); the expression level is judged as being higher when the relative expression ratio is more than 2.0.

Detection Reagents

The present invention provides detection reagents for hepatocellular carcinomas.

In one embodiment, the detection reagent of the present invention comprises a polynucleotide having at least 15 nucleotides which hybridizes with DDEFL1, VANGL1 or LGN, specifically SEQ ID NO: 1, NO: 3, or NO: 5. The polynucleotide can be used in the above-mentioned detection method of the present invention as a probe or a primer. When used as a probe, the polynucleotides contained in the detection reagent of the present invention can be labeled. The method of labeling includes, for example, a labeling method using T4 polynucleotide kinase to phosphorylate the 5'-terminus of the polynucleotide with $^{32}P$; and a method of introducing substrate bases, which are labeled with isotopes such as $^{32}P$, fluorescent dyes, biotin, and so on using random hexamer oligonucleotides and such as primers and DNA polymerase such as Klenow enzyme (the random prime method, etc.).

In another embodiment, the detection reagent of the present invention comprises an antibody that binds to the DDEFL1, VANGL1, or LGN polypeptide, specifically the polypeptide having the amino acid sequence of SEQ ID NO: 2, NO: 4, or NO: 6. The antibodies are used to detect the polypeptides of the present invention in the above-mentioned detection method of the present invention. The antibodies may be labeled according to the diction method. Furthermore, the antibodies may be immobilized on a solid support.

The detection reagent of the present invention may further comprise a medium or additive, including sterilized water, physiological saline, vegetable oils, surfactants, lipids, solubilizers, buffers, protein stabilizers (such as bovine serum albumin and gelatin), preservatives, and such, as long as it does not affect the reactions used in the detection method of the present invention.

Methods for Inhibiting Growth of Hematocellular Carcinomas

The present invention further provides a method for inhibiting growth of hepatocellular carcinomas. In specific embodiments, this method can be performed by introducing an antisense oligonucleotide of DDEFL1, VANGL1, or LGN into the target cells.

The antisense oligonucleotide used in this method hybridizes with any site within the nucleotide sequence of SEQ ID NO: 1, NO: 3, or NO: 5. The antisense oligonucleotides include not only those in which the entire nucleotides corresponding to those constituting a specified region of a DNA or mRNA are complementary, but also those having a mismatch of one or more nucleotides, as long as DNA or mRNA and an oligonucleotide can specifically hybridize with the nucleotide sequence of SEQ ID NO: 1, NO: 3, or NO: 5.

The antisense oligonucleotide is preferably that against at least 15 continuous nucleotides in the nucleotide sequence of SEQ ID NO: 1, NO: 3, or NO: 5. The above-mentioned antisense oligonucleotide, which contains an initiation codon in the above-mentioned at least 15 continuous nucleotides, is even more preferred.

The antisense oligonucleotides includes analogs containing lower alkyl phosphonate (e.g., methyl-phosphonate or ethyl-phosphonate), phosphothioate, and phosphoamidate.

Herein, the target cells may be mammalian cells, preferably human cells.

The introduction method may be in vitro, in vivo, or ex vivo transfer method. In one embodiment, the antisense oligonucleotides can be introduced into the target cells by a conventional transfection method. Alternatively, the introduction can be made by conventional gene transfer technique using a vector carrying the antisense oligonucleotide, such as adenovirus vectors, retrovirus vectors, or cationic liposomes.

Any patents, patent applications, and publications cited herein are incorporated by reference.

BRIEF DESCRIPTION OF DRAWINGS

FIG. 1a shows relative expression ratio (cancer/non-cancer) of B9362 in primary 20 HCCs examined by cDNA microarray. FIG. 1b presents photographs showing expression of B9362 analyzed by semi-quantitative RT-PCR using additional 11 HCC cases. Expression of GAPDH served as an internal control.

FIG. 2a is a photograph showing the results of Northern blot analysis of DDEFL1 in various human tissues. FIG. 2b shows the structure of DDEFL1. FIG. 2c shows similarity between the expected DDEFL1 protein and members of ArfGAP family. FIG. 2d shows identity between the amino acid sequence of the ArfGAP motif in DDEFL1 and that in DDEF2. The arrows indicate a $CXXCX_{16}CXXC$ motif, representing a zinc finger structure essential to GAP activity.

FIG. 3a is a photograph showing the results of Western blot analysis, indicating that cMyc-tagged DDEFL1 protein was expressed in COS7 cells transfected with pcDNA-DDEFL1-myc plasmid. FIG. 3b presents photographs showing immunocytochemistry of the cells, suggesting that cMyc-tagged DDEFL1 protein localized in the cytoplasm.

FIG. 4a presents photographs showing the results of colony formation assays, indicating that DDEFL1 promotes cell growth in NIH3T3, SNU423, and Alexander cells. FIG. 4b presents photographs showing stable expression of exogeneous DDEFL1 by NIH3T3-DDEFL1 cells. FIG. 4c is a graph showing growth of NIH3T3-DDEFL1 cells stably expressing exogeneous DDEFL1 in culture media containing 10% FBS. FIG. 4d is a graph showing growth of NIH3T3-DDEFL1 cells in culture media containing 0.1% FBS ($P<0.01$).

FIG. 5a shows designation of antisense S-oligonucleotides and photographs showing reduced expression of DDEFL1 by the transfection of AS1 or AS5 antisense S-oligonucleotides. FIG. 5b presents photographs showing that AS1 and AS5 suppressed growth of SNU475 cells.

FIG. 6a shows relative expression ratios (cancer/non-cancer) of VANGL1 in primary 20 HCCs examined by cDNA microarray. FIG. 6b presents photographs showing expression of D3244 analyzed by semi-quantitative RT-PCR using additional 10 HCC cases. T, tumor tissue; N, normal tissue. Expression of GAPDH served as an internal control.

FIG. 7a is a photograph showing the results of multiple-tissue Northern blot analysis of VANGL1 in various human tissues. FIG. 7b shows predicted protein structure of VANGL1.

FIG. 8a presents photographs of SNU475 cells transfected with pcDNA3.1-myc/His-VANGL1 stained with mouse anti-mycmonoclonal antibody and visualized by Rhodamine conjugated secondary anti-mouse IgG antibody. Nuclei were counter-stained with DAPI. FIG. 8b presents photographs of mock cells similarly stained and visualized.

FIG. 9a presents photographs showing expression of VANGL1 in SNU475 cells treated with either control or antisense oligonucleotide for 12 hours. FIG. 9b is a photograph showing that S-oligonucleotide suppressed growth of SNU423 cells. FIG. 9c is a graph showing the results of analysis of cell viability by MTT assay. FIG. 9d shows the results of fluorescence activated cell sorting (FACS) analysis of cells treated with sense or antisense oligonucleotide.

FIG. 10a shows relative expression ratios (cancer/non-cancer) of LGN in primary 20 HCCs studied by cDNA microarray. FIG. 10b presents photographs showing expression of LGN analyzed by semi-quantitative RT-PCR using additional ten HCCs. Expression of GAPDH served as an internal control. T, tumor tissue; N, normal tissue.

FIG. 12a is a photograph of COS7 cells transfected with pcDNA3.1-myc/His-LGN, in which nuclei was counterstained with DAPI. FIG. 12b is a photograph of COS7 cells transfected with pcDNA3.1-myc/His-LGN, which were stained with mouse anti c-myc antibody and visualized by Rhodamine conjugated secondary anti-mouse IgG antibody. FIG. 12c is a merge of a and b.

FIG. 13a presents photographs showing the results of colony formation assays, indicating that LGN promotes cell growth in NIH3T3, SNU423, Alexander, and SNU475 cells. FIG. 13b is a graph showing growth of NIH3T3-LGN cells stably expressing exogeneous LGN was higher than that of mock (NIH3T3-LacZ) cells in culture media containing 10% FBS.

FIG. 14a presents photographs showing reduced expression of LGN by the transfection of antisense S-oligonucleotide, antisense 3. FIG. 4b is a photograph showing that antisense 3 suppressed growth of SNU423 cells.

BEST MODE FOR CARRYING OUT THE INVENTION

The present invention will be illustrated with reference to the following examples, but is not construed as being limited thereto.

EXAMPLE 1

Figure 1:
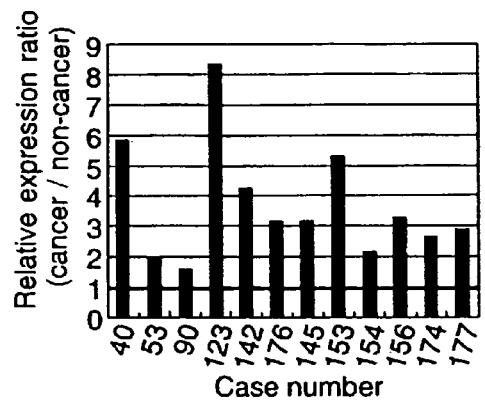
FIGS. 1a-1b show expression of a gene termed B9362 in HCCs.
Figure 1:
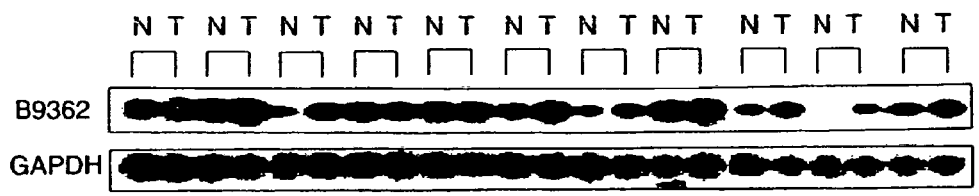

1-1. Identification of DDEFL1 Commonly Up-regulated in Human Hepatocellular Carcinomas By means of a genome-wide cDNA microarray containing 23040 genes, expression profiles of 20 hepatocellular carcinomas (HCC) were compared with their corresponding non-cancerous liver tissues. All HCC tissues and corresponding non-cancerous tissues were obtained with informed consent from surgical specimens of patients who underwent hepatectomy. A gene with an in-house accession number of B9362 corresponding to an EST, Hs.44579 of a UniGene cluster, was found to be over-expressed in a range between 1.57 and 5.83 (FIG. 1a). Its up-regulated expression (Cy3:Cy5 intensity ratio, >2.0) was observed in 11 of the 12 HCCs that passed through the cutoff filter (both Cy3 and Cy5 signals greater than 25,000). Since an open reading frame of this gene encoded a protein approximately 60% identical to that of development and differentiation enhancing factor 2 (DDEF2), this gene was termed development and differentiation enhancing factor-like 1 (DDEFL1). To clarify the results of the cDNA microarray, expression of this transcript was examined in an additional 11 HCCs by semi-quantitative RT-PCR. Expression of GAPDH served as an internal control. RT-PCR was performed as follows. Total RNA was extracted with a Qiagen RNeasy kit (Qiagen) or Trizol reagent (Life Technologies, Inc.) according to the manufacturers' protocols. Ten-microgram aliquots of total RNA were reversely transcribed for single-stranded cDNAs using poly $dT_{12-18}$ primer (Amersham Pharmacia Biotech) with Superscript II reverse transcriptase (Life Technologies). Single-stranded cDNA preparation was diluted for subsequent PCR amplification by standard RT-PCR experiments carried out in 20-µl volumes of PCR buffer (TAKARA). Amplification proceeded for 4 min at 94° C. for denaturing, followed by 20 (for GAPDH) or 33 (for DDEFL1) cycles of 94° C. for 30 s, 56° C. for 30 s, and 72° C. for 45 s, in the GeneAmp PCR system 9700 (Perkin-Elmer, Foster City, Calif.). Primer sequences were; for GAPDH: forward, 5'-ACAACAGCCTCAAGATCATCAG (SEQ ID NO: 7) and reverse, 5'-GGTCCACCACTGA-CACGTTG (SEQ ID NO: 8); for DDEFL1: forward, 5'-AGCTGAGACATTTGTTCTCTTG (SEQ ID NO: 9) and reverse: 5'-TATAAACCAGCTGAGTCCAGAG (SEQ ID NO: 10). The results confirmed increased expression of DDEFL1 in nine of these tumors (FIG. 1b).

1-2. Isolation and Structure of a Novel Gene DDEFL1

Figure 2:
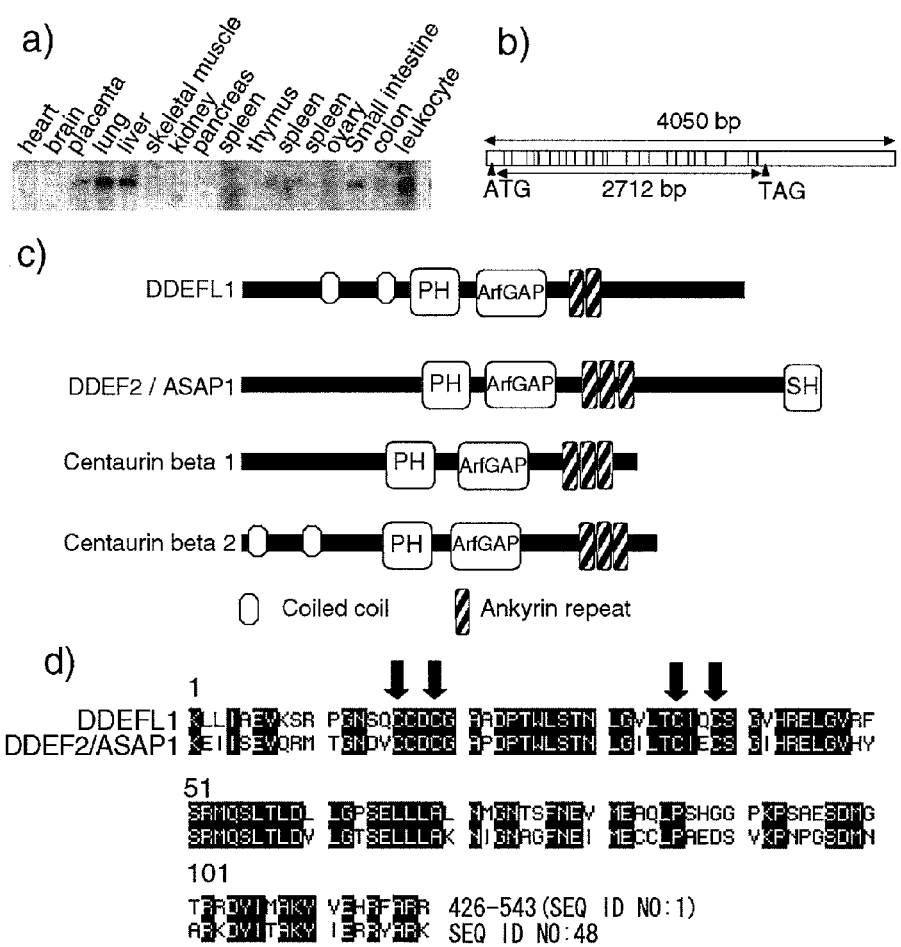
FIG. 2a-2d show the results of identification of DDEFL1.

Expression of DDEFL1 was analyzed by multiple-tissue northern-blot analysis using a PCR product of DDEFL1 as a probe. Human multiple-tissue blots (Clontech, Palo Alto, Calif.) were hybridized with a $^{32}$P-labeled DDEFL1 cDNA. Pre-hybridization, hybridization and washing were performed according to the supplier's recommendations. The blots were autoradiographed within tensifying screens at −80° C. for 72 h. The results revealed a 4-kb transcript that was expressed in lung, liver, small intestine, placenta and peripheral blood leukocyte (FIG. 2a).

Since B9362 was smaller than that detected on the Northern blot, 5' RACE experiments was carried out to determine the entire coding sequence of the gene. 5' RACE experiments were carried out using a Marathon cDNA amplification kit (Clontech, Palo Alto, Calif.) according to the manufacturer's instructions. For the amplification of the 5' part of DDEFL1 cDNAs, gene-specific reverse primers (5'-CT-CACTTGGCACGTCAGCAGGG (SEQ ID NO: 11)) and the AP-1 primer supplied in the kit were used. The cDNA template was synthesized from human liver mRNA. The PCR products were cloned using a TA cloning kit (Invitrogen) and their sequences were determined with an ABI PRISM 3700 DNA sequencer (Applied Biosystems).

The complete cDNA consisted of 4050 nucleotides, with an open reading frame of 2712 nucleotides encoding a 903-amino-acid protein (GenBank accession number AB051853). The first ATG was flanked by a sequence (CCCGCCATGC (SEQ ID NO: 12)) that agreed with the consensus sequence for initiation of translation in eukaryotes, with an in-frame stop codon upstream. The BLAST program to search for homologies in the NCBI (the National Center for Biotechnology Information) database, identified a genomic sequence with GenBank accession number AL357134, which had been assigned to chromosomal band 1p36.12. Comparison of the cDNA and genomic sequences disclosed that DDEFL1 consisted of 25 exons (FIG. 2b).

A search for protein motifs with the Simple Modular Architecture Research Tool (SMART) revealed that the predicted protein contained two coiled-coil regions (codons 141-172 and 241-278), a PH (Pleckstrin homology) motif (codons 303-396), a motif of ArfGAP (GTPase-activating protein for Arf) (codons 426-551) and two ankyrin repeats (codons 585-617 and 621-653). This structure was similar to centaurin beta 1 and centaurin beta 2 (FIG. 2c). In particular, DDEFL1 shared features of centaurin-family proteins such as a PH domain, a target of phosphatidylinositol 3,4,5-trisphosphate, and a motif of ArfGAP. The amino acid sequence of the ArfGAP motif of DDEFL1 was 67.8% identical to that of DDEF2 (FIG. 2d). Notably, the CXXCX$_{16}$CXXC motif, representing a zinc finger structure essential to GAP activity, was completely preserved.

1-3. Subcellular Localization of DDEFL1

Figure 3:
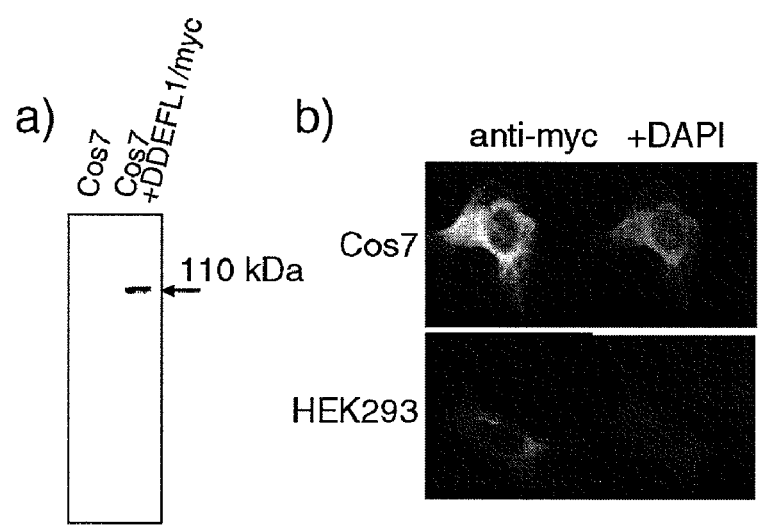
FIG. 3a-3b show subcellular localization of DDEFL1.

The coding sequence of DDEFL1 was cloned into the pcDNA3.1-myc/His vector (Invitrogen). The resulting plasmid expressing myc-tagged DDEFL1 protein (pDNA-myc/His-DDEFL1) was transiently transfected into COS7 cells (American Type Culture Collection (ATCC)). The expected myc-tagged protein was detected by immunoblotting (Western blotting) as follows. Cells transfected with pcDNA3.1-myc/His-DDEFL1 were washed twice with PBS and harvested in lysis buffer (150 mM NaCl, 1% Triton X-100, 50 mM Tris-HCl pH 7.4, 1 mM DTT, and 1×complete Protease Inhibitor Cocktail (Boehringer)). After the cells were homogenized and centrifuged at 10,000×g for 30 min, the supernatant was standardized for protein concentration by the Bradford assay (Bio-Rad). Proteins were separated by 10% SDS-PAGE and immunoblotted with mouse anti-myc antibody. HRP-conjugated goat anti-mouse IgG (Amersham) served as the secondary antibody for the ECL Detection System (Amersham). As a result, the DDEFL1 protein was detected on western blots with an anti-myc antibody (FIG. 3a).

Furthermore, immunocytochemical staining was performed as follows. First, the cells were fixed with PBS containing 4% paraformaldehyde for 15 min, then rendered permeable with PBS containing 0.1% Triton X-100 for 2.5 min at RT. Subsequently the cells were covered with 2% BSA in PBS for 24 h at 4° C. to block non-specific hybridization. Mouse anti-myc monoclonal antibody (Sigma) at 1:1000 dilution or mouse anti-FLAG antibody (Sigma) at 1:2000 dilution was used for the first antibody, and the reaction was visualized after incubation with Rhodamine-conjugated anti-mouse second antibody (Leinco and ICN). Nuclei were counter-stained with 4',6'-diamidine-2'-phenylindole dihydrochloride (DAPI). Fluorescent images were obtained under an ECLIPSE E800 microscope. The microscopic analysis indicated that the protein was present mainly in the cytoplasm (FIG. 3b). DDEFL1 was also localized in the cytoplasm of human embryonal kidney (HEK293) cells (ATCC).

1-4. Effect of DDEFL1 on Cell Growth

Figure 4:
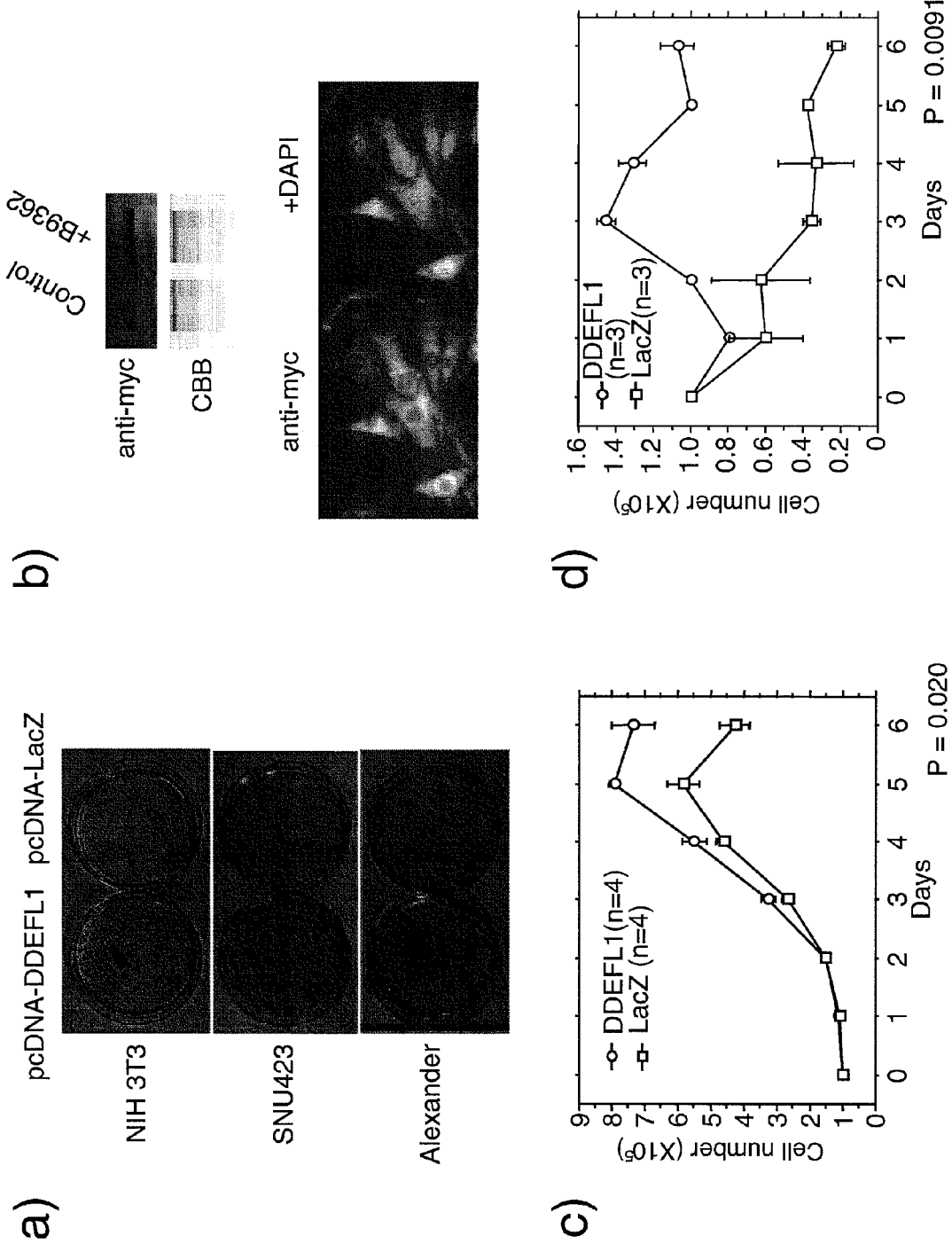
FIG. 4a-4d show growth-promoting effect of DDEFL1.

The coding sequence of DDEFL1 was cloned into the pcDNA 3.1 vector (Invitrogen). NIH3T3 cells (ATCC) platedonto 10-cm dishes (2×10$^5$ cells/dish) were transfected with the resulting plasmid expressing DDEFL1 (pcDNA-DDEFL1) and the control plasmid (pcDNA-LacZ) and cultured in Dulbecco's modified Eagle's medium supplemented with 10% fetal bovine serum and 1% antibiotic/antimycotic solution (Sigma), and further with an appropriate concentration of geneticin for two weeks. The cells were then fixed with 100% methanol and stained by Giemsa solution. Cells transfected with pcDNA-DDEFL1 produced markedly more colonies than control cells. An increase in colony formation similarly occurred with transfected human hepatoma SNU423 (Korea cell-line bank) and Alexander (ATCC) cells, in which endogenous expression of DDEFL1 is very low (FIG. 4a).

To investigate this growth-promoting effect further, NIH3T3 cells that stably expressed exogeneous DDEFL1 were established. pDNA-myc/His-DDEFL1 was transfected into NIH3T3 cells using FuGENE6 reagent (Boehringer) according to the supplier's recommendations. Twenty-four hours after transfection, geneticin was added to the cultures and single colonies were selected two weeks after transfection. Expression of DDEFL1 was determined by semi-quantitative RT-PCR (FIG. 4b). The growth rate of NIH3T3-DDEFL1 cells was statistically higher than that of mock (NIH3T3-LacZ) cells in culture media containing 10% FBS (P<0.05) (FIG. 4c). In media containing only 0.1% FBS, NIH3T3-DDEFL1 cells survived for 6 days, while control NIH3T3 cells died within 6 days under the same conditions. In this case, growth of NIH3T3-DDEFL1 cells was statistically higher than that of mock cells in culture media containing 0.1% FBS (P<0.01) (FIG. 4d).

1-5. Suppression of DDEFL1 Expression in Human Hepatoma SNU475 Cells by Antisense S-oligonucleotides The following six pairs of control (sense) and antisense S-oligonucleotides corresponding to the DDEFL1 gene were synthesized.

Antisense:

```
                                      (SEQ ID NO: 13)
    DDEFL1-AS1    5'-TGCTCCGGCATGGCGG-3';

(SEQ ID NO: 14)
    DDEFL1-AS2    5'-GCTGAACTGCTCCGGC-3';

(SEQ ID NO: 15)
    DDEFL1-AS3    5'-TCCAAGATCTCCTCCC-3';

(SEQ ID NO: 16)
    DDEFL1-AS4    5'-TCTCCTTCCAAGATCT-3';

(SEQ ID NO: 17)
    DDEFL1-AS5    5'-GCGCTGAGCCGGCCTC-3';
    and (SEQ ID NO: 18)
    DDEFL1-AS6    5'-CCTCACCTCCTCCCGC-3'.
```

Control:

```
DDEFL1-S1  5'-CCGCCATGCCGGAGCA-3';   (SEQ ID NO: 19)

DDEFL1-S2  5'-GCCGGAGCAGTTCAGC-3';   (SEQ ID NO: 20)

DDEFL1-S3  5'-GGGAGGAGATCTTGGA-3';   (SEQ ID NO: 21)

DDEFL1-S4  5'-AGATCTTGGAAGGAGA-3';   (SEQ ID NO: 22)

DDEFL1-S5  5'-GAGGCCGGCTCAGCGC-3';   (SEQ ID NO: 23)
and

DDEFL1-S6  5'-GCGGGAGGAGGTGAGG-3'.   (SEQ ID NO: 24)
```

Figure 5:
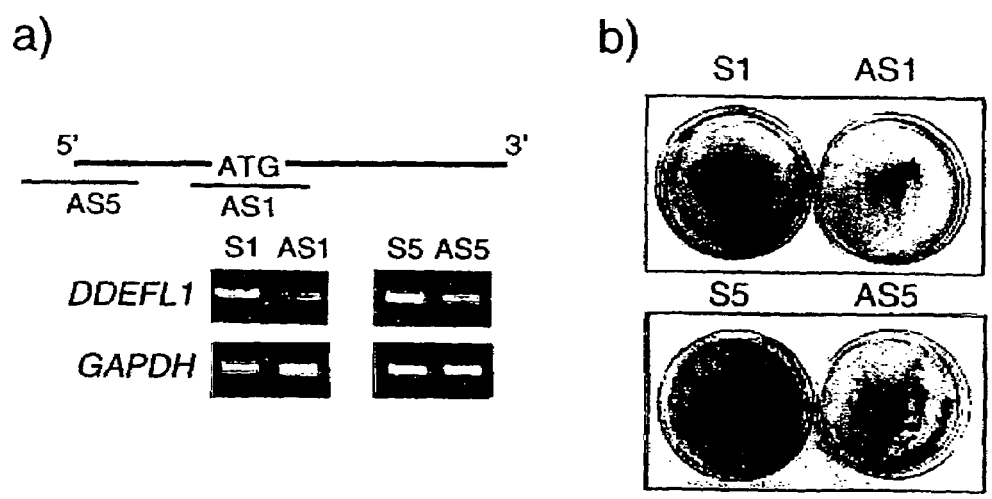
FIG. 5a-5b show growth suppression by antisense S-oligonucleotides designated to suppress DDEFL1 in SNU475 cells.

Using LIPOFECTIN Reagent (GIBCO BRL), the synthetic S-oligonucleotides were transfected into SNU475 cells (Korea cell-line bank), which had shown the highest level of DDEFL1 expression among the six hepatoma cell lines we examined (data not shown). Twelve and twenty-four hours after transfection, antisense S-oligonucleotides AS1 and AS5 significantly suppressed expression of DDEFL1 compared to the respective control S-oligonucleotides S1 and S5 (FIG. 5a). Six days after transfection, surviving cells transfected with antisense S-oligonucleotide AS1 or AS5 were markedly fewer than cells transfected with the respective control S-oligonucleotide S1 or S5 (FIG. 5b). Consistent results were obtained in three independent experiments.

EXAMPLE 2

Figure 6:
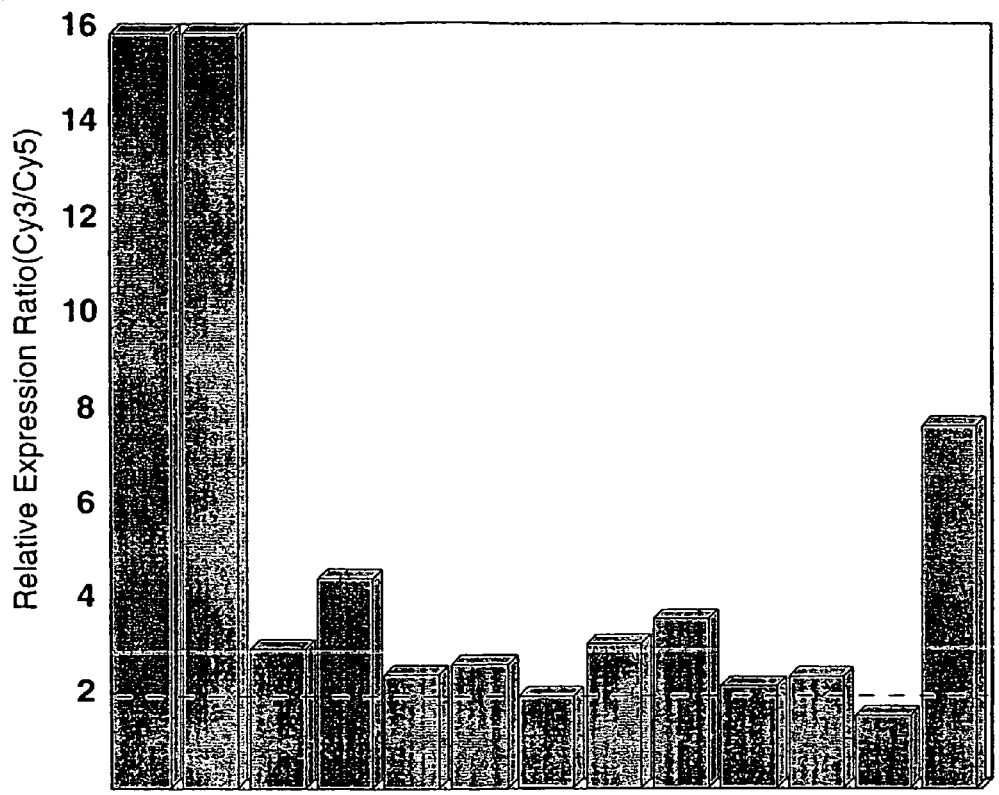
FIG. 6a-6b show expression of VANGL1 in HCCs.
Figure 6:
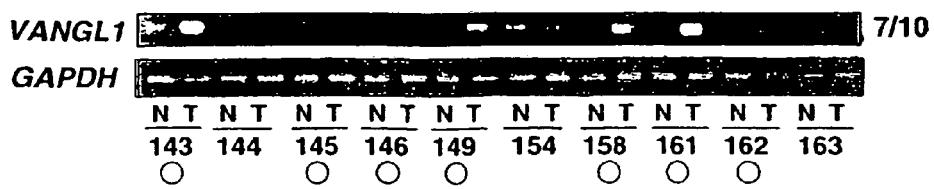

2-1. Identification of VANGL1 Commonly Up-regulated in Human Hepatocellular Carcinomas The genome-wide cDNA microarray analysis carried out in Example 1 also revealed that a gene with an in-house accession number of D3244 corresponding to an EST (Hs.122730) of a UniGene cluster, was found to be significantly up-regulated in ten of twelve clinical HCCs compared with the corresponding non-cancerous liver tissues. The relative expression ratio compared to corresponding non-cancerous tissue of these 12 tumors ranged from 1.5 to 16.0 (FIG. 6a). Up-regulated expression (Cy3:Cy5 intensity ratio, >2.0) was observed in 10 of the 12 HCCs that passed through the cutoff filter (both Cy3 and Cy5 signals greater than 25,000). The elevated expression of D3244 was also confirmed in ten additional HCC cases by semi-quantitative RT-PCR performed similarly to Example 1-1 using the primer set, forward: 5'-GAGTTGTATTATGAAGAGGC-CGA (SEQ ID NO: 25); reverse: 5'-ATGTCTCAGACTG-TAAGCGAAGG (SEQ ID NO: 26) (FIG. 6b).

2-2. Expression of VANGL1 in Human Adult Tissues

Figure 7:
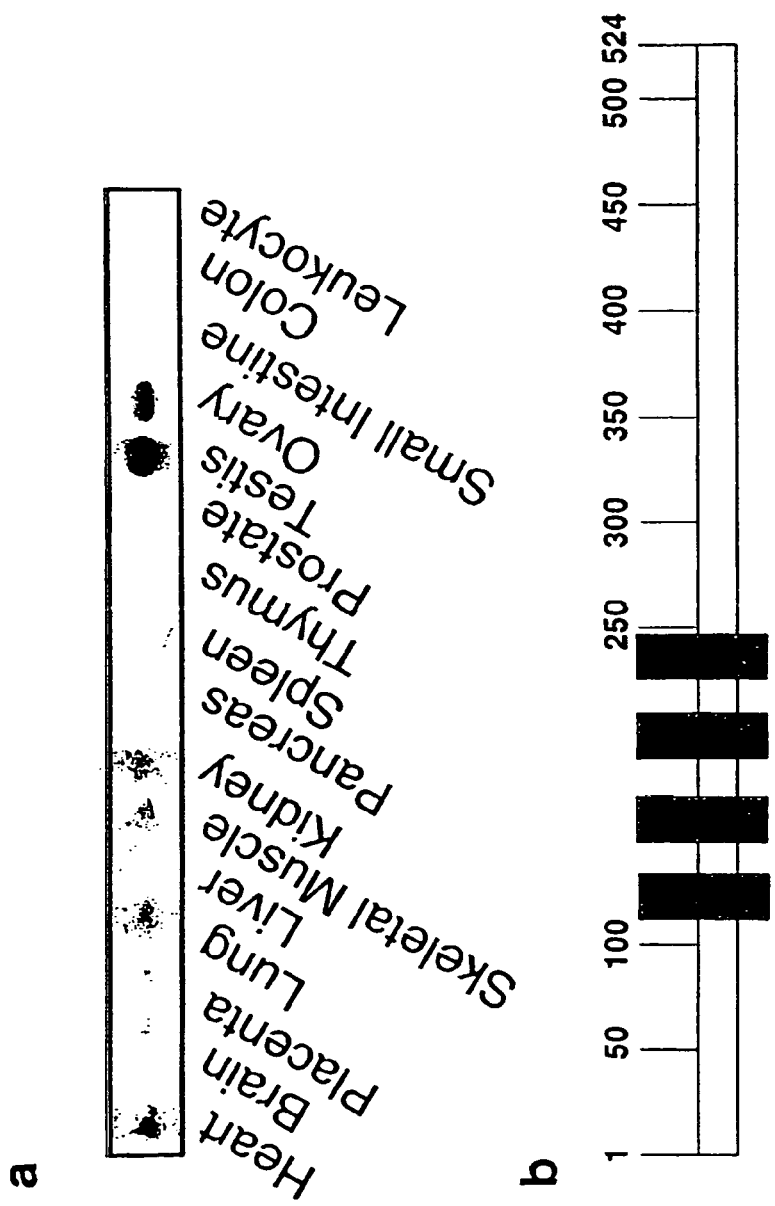
FIGS. 7a and 7B show the results of identification of VANGL1.

Multi-tissue northern blot analysis using D3244 cDNA as a probe was performed in the same manner as in Example 1-2 and the results showed a 1.9-kb transcript abundantly expressed in test is and ovary in a tissue-specific manner (FIG. 7a). NCBI database search for genomic sequences corresponding to D3244 found two sequences (GenBank accession number: AL450389 and AL592436) assigned to chromosomal band 1p22. Using GENSCAN, and Gene Recognition and Assembly Internet Link program, candidate-exon sequences were predicted and exon-connection was performed. In addition, 5' RACE was carried out using a reverse primer (5'-TGTCAGCTCTCCGCTTGCG-GAAAAAAG (SEQ ID NO: 27)) to determine the sequence of the 5' region of the transcript in the same manner as in Example 1-2. As a result, an assembled human cDNA sequence of 1879 nucleotides containing an open reading frame of 1572 nucleotides (GenBank accession number: AB057596) was obtained. The predicted amino acid sequence shared 40% and 63% identity with *strabismus* (VanGogh) and VANGL2. Hence, the gene corresponding D3244 was termed as Van Gogh Like 1 (VANGL1). Simple Modular Architecture Research. Tool suggested that the predicted protein contained putative four transmembrane domains (codons 111-133, 148-170, 182-204, 219-241) (FIG. 7b).

2-3. Subcellular Localization of VANGL1

Figure 8:
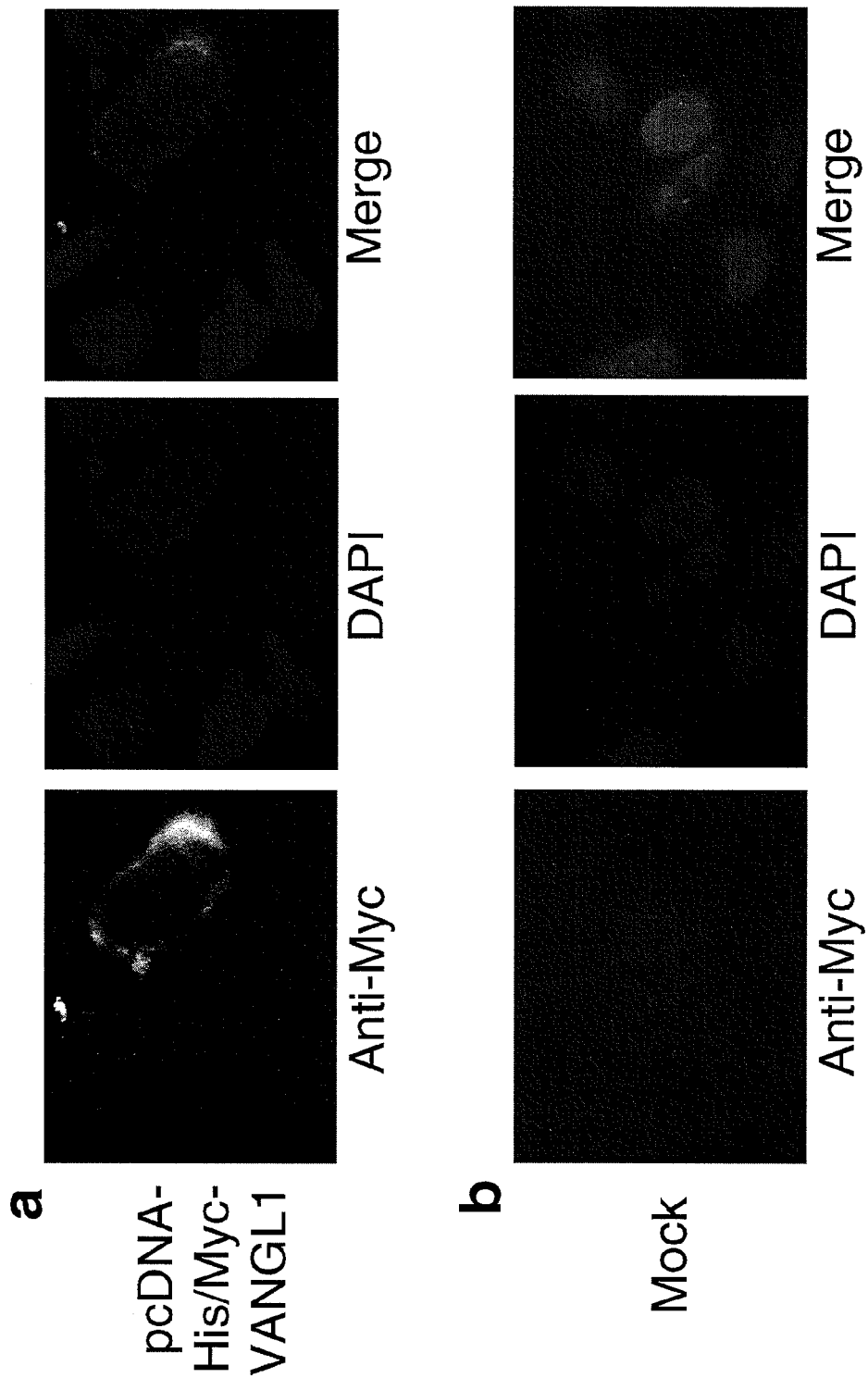
FIGS. 8a and 8b show subcellular localization of VANGL1.

The pcDNA3.1-myc/His-VANGL1 plasmid expressing c-myc-tagged VANGL1 protein was transiently transfected into SNU475 cells (Korea cell-line bank). Immunocytochemical staining was performed in the same manner as in Example 1-3. The results revealed that the tagged VANGL1 protein was present in the cytoplasm (FIGS. 8a and 8b).

2-4. Growth Suppression of Hepatoma Cells by Antisense S-oligonucleotides Designated to Reduce Expression of VANGL1

To test whether suppression of VANGL1 may result in cell cycle arrest and/or cell death of HCC cells, the following four pairs of antisense and control (sense) S-oligonucleotides were synthesized and transfected into SNU475 cells.

Antisense:

```
antisense 1    5'-GTATCCATAGCAATGG-3';   (SEQ ID NO: 28)
antisense 2    5'-TGGATTGGGTATCCAT-3';   (SEQ ID NO: 29)
antisense 3    5'-TAAGTGGATTGGGTAT-3';   (SEQ ID NO: 30)
and
antisense 4    5'-ACTCCTACCTGCCTGT-3'.   (SEQ ID NO: 31)
```

Control:

```
sense 1    5'-CCATTGCTATGGATAC-3';    (SEQ ID NO: 32)
sense 2    5'-ATGGATACCCAATCCA-3';    (SEQ ID NO: 33)
sense 3    5'-ATACCCAATCCACTTA-3';    (SEQ ID NO: 34)
and
sense 4    5'-ACAGGCAGGTAGGAGT-3'.    (SEQ ID NO: 35)
```

Figure 9:
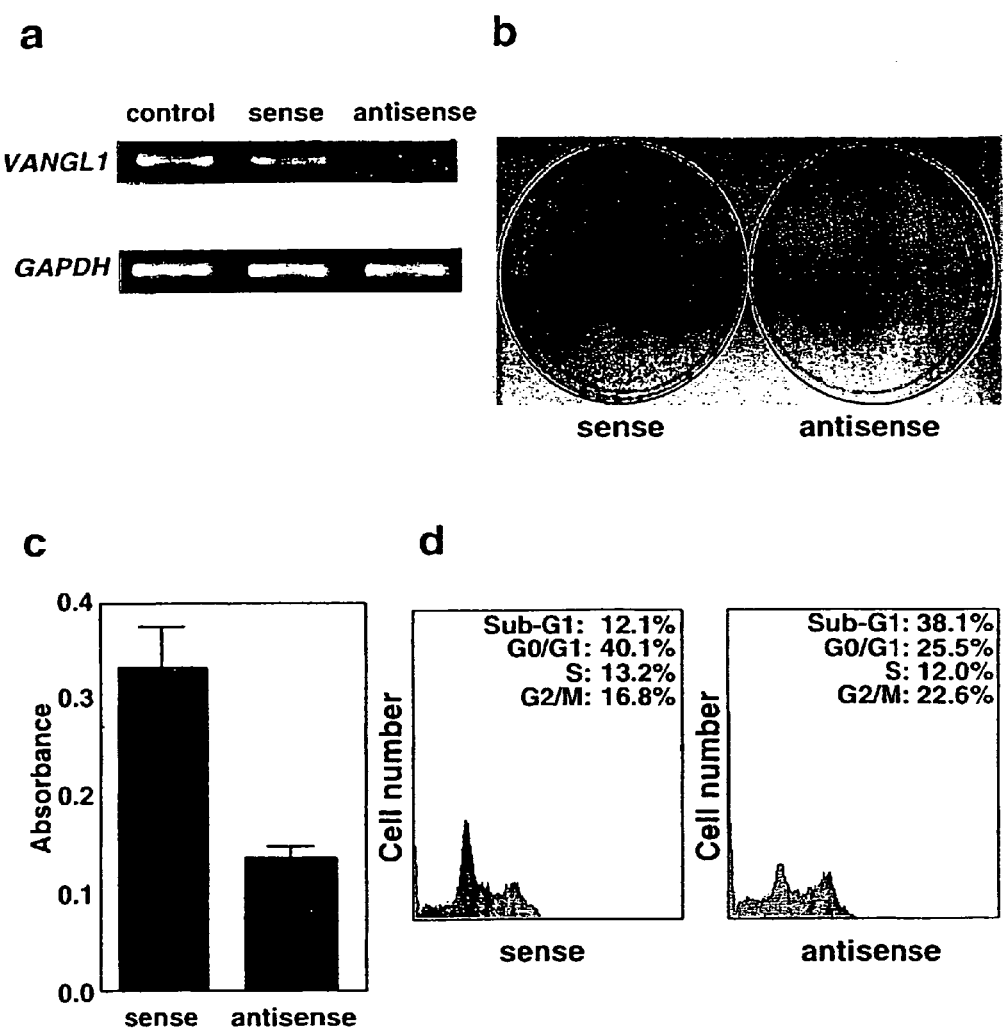
FIG. 9a-9d show growth suppressive effect of antisense S-oligonucleotide designated to suppress VANGL1.

Antisense S-oligonucleotide encompassing the initiation codon (antisense 3) significantly decreased endogenous expression of VANGL1 in SNU475 cells (FIG. 9a).

Cell viability was evaluated by 3-(4,5-dimethyl-thiazol-2-yl)-2,5-diphenyltetrazolium bromide (MTT) assay as follows. Cells were plated at a density of $5 \times 10^5$ cells/100 mm dish. At 24 hours after seeding, the cells were transfected in triplicate with sense or antisense S-oligonucleotide designated to suppress VANGL1. At 72 hours after transfection, the medium was replaced with fresh medium containing 500 μg/ml of 3-(4,5-dimethylthiazol-2-yl)-2,5-diphenyl tetrazolium bromide (MTT) (Sigma) and the plates were incubated for four hours at 37° C. Subsequently, the cells were lysed by the addition of 1 ml of 0.01 N HCl/10% SDS and absorbance of lysates was measured with an ELISA plate reader at a test wavelength of 570 nm (reference, 630 nm). The cell viability was represented by the absorbance compared to that of control cells.

Transfection of the antisense S-oligonucleotide, antisense 3, significantly reduced number of surviving cells compared with control sense S-oligonucleotide, sense 3 (FIG. 9b and 9c). This result was confirmed by three independent experiments.

Furthermore, flow cytometry analysis was performed as follows. Cells were plated at a density of $1 \times 10^5$ cells/100 mm dish and trypsinized at the given time course, followed by fixation in 70% cold ethanol. After RNase treatment, cells were stained with propidium iodide (50 μg/ml) in PBS. Flow cytometry was performed on a Becton Dickinson FACScan and analyzed by CellQuest and ModFit software (Verity Software House). The percentages of nuclei in G0/G1, S and G2/M phases of the cell cycle, and any sub-G1 population were determined from at least 20,000 ungated cells.

FACS analysis demonstrated that inhibition of VANGL1 significantly increased number of cells at sub-G1 phase (FIG. 9d). These results suggest that VANGL1 may play an important role for cell growth and/or survival of hepatocellular carcinoma cells.

EXAMPLE 3

3-1. LGN is Commonly Increased in Human Hepatocellular Carcinomas

Figure 10:
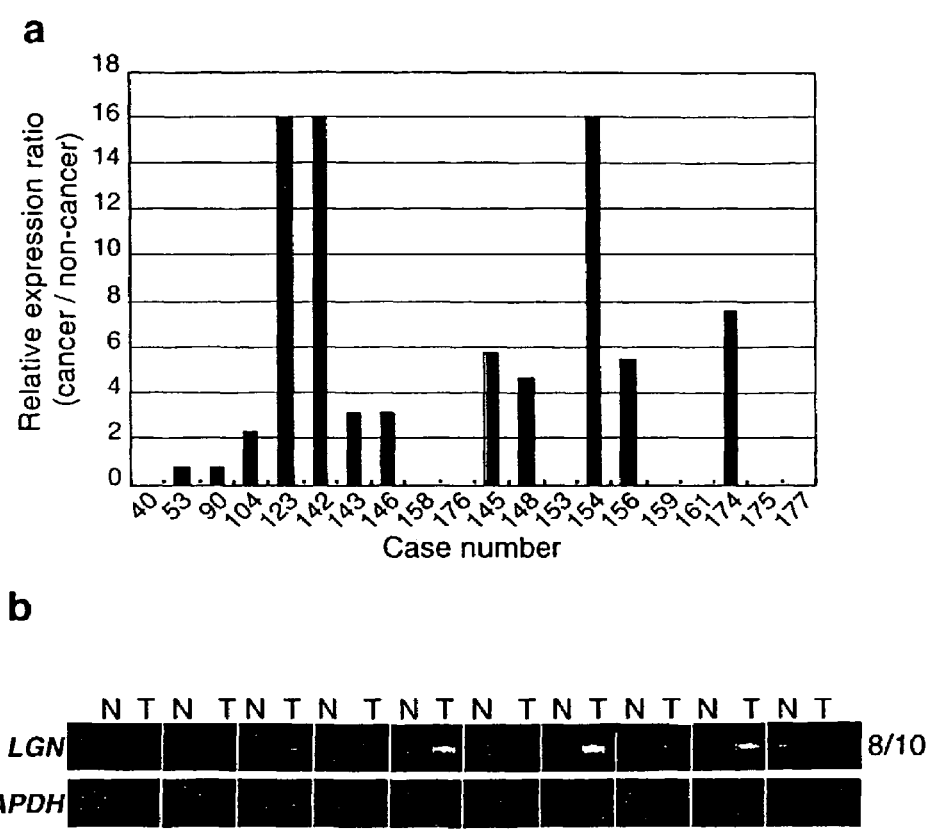
FIGS. 10a and 10b show LGN gene expression of HCCs compared with their corresponding non-cancerous liver tissues.

Among commonly up-regulated genes by the microarray analysis performed in Example 1-1, a gene, D3636 corresponding to LGN (GenBank accession number: U54999) was selected because it was significantly up-regulated in ten of twelve clinical HCCs compared with the corresponding non-cancerous liver tissues. The relative expression ratio compared to corresponding non-cancerous tissue of these 12 tumors ranged from 0.7 to 16.0. Up-regulated expression of LGN (Cy3:Cy5 intensity ratio, >2.0) was observed in 10 of the 12 HCCs that passed through the cutoff filter (both Cy3 and Cy5 signals greater than 25,000) (FIG. 10a). The elevated expression of LGN was also confirmed in additional ten HCC cases by semi-quantitative RT-PCR performed using a primer set, forward: 5'-ATCTGAAGCACT-TAGCAATTGC (SEQ ID NO: 36), reverse: 5'-CTGTAGCTCAGACCAAGAACC (SEQ ID NO: 37), similarly to Example 1-1 (FIG. 10b).

3-2. Genomic Structure of LGN

Figure 11:
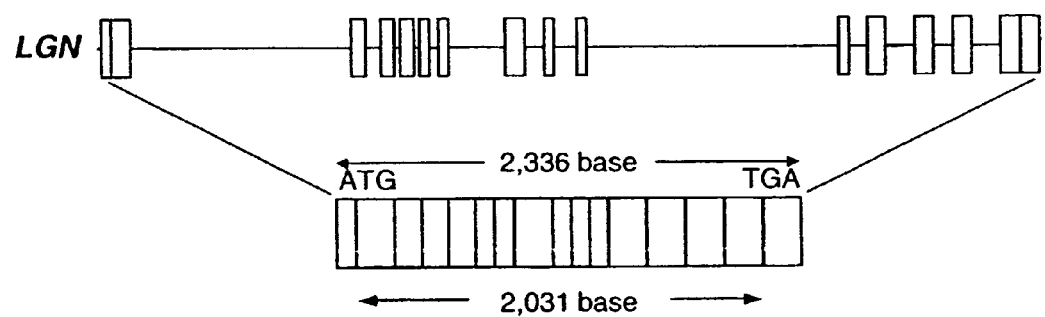
FIG. 11 shows genomic structure of LGN.

LGN cDNA consists of 2,336 nucleotides and encodes a 677 amino acid peptide. Comparison of the cDNA sequence with genomic sequences disclosed that the LGN gene consists of 14 exons (FIG. 11).

3-3. Subcellular Localization of LGN

Figure 12:
FIG. 12a-12c show subcellular localization of LGN.

The pcDNA3.1-myc/His-LGN plasmid expressing c-myc-tagged LGN protein was transiently transfected into COS7 cells. A 72 kDa-band corresponding to myc-tagged LGN protein was detected by immunoblot analysis in the same manner as in Example 1-3 (FIG. 12). Similarly, immunocytochemical staining was performed as in Example 1-3 and the results revealed that the tagged LGN protein was present in the cytoplasm and nucleus in the cells.

3-4. LGN Gene Transfer Can Promote Cell Growth

Figure 13:
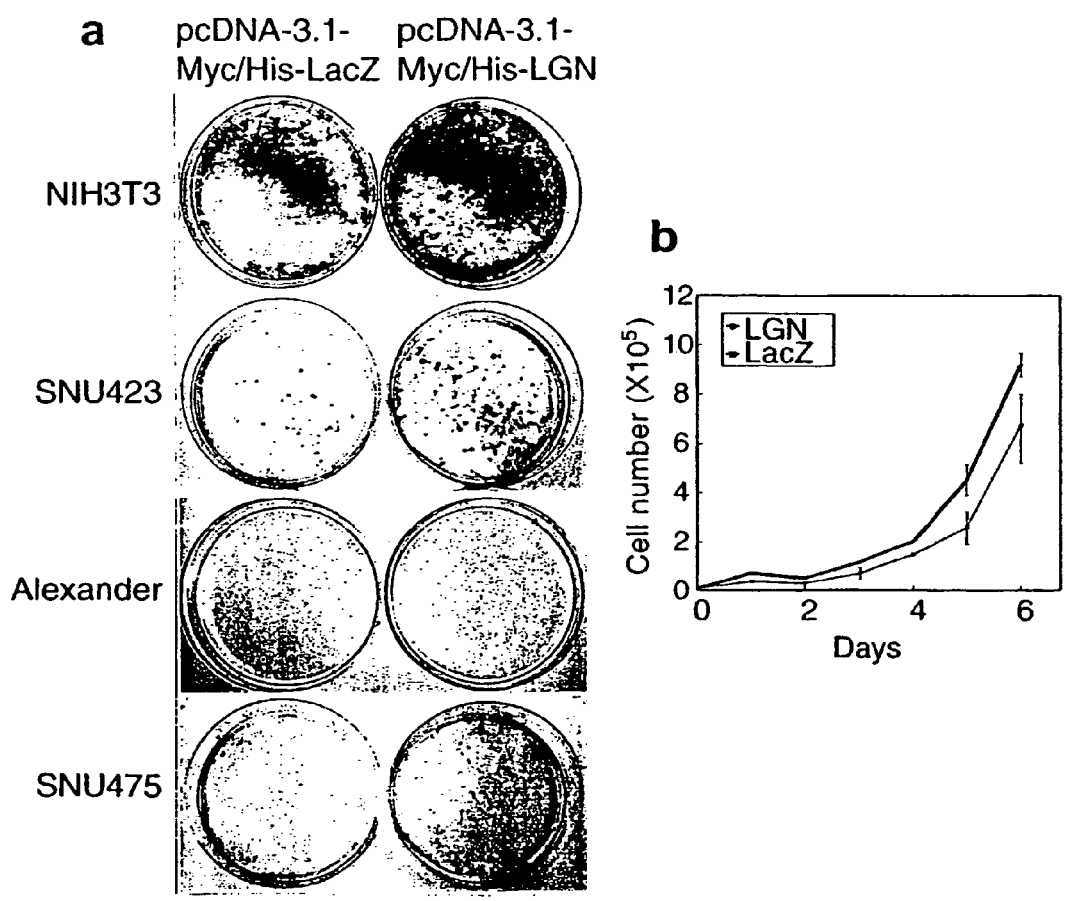
FIGS. 13a and 13b show growth-promoting effect of LGN.

To analyze the effect of LGN on cell growth, a colony-formation assay was carried out as in Example 1-4 by transfecting NIH3T3, SNU423, Alexander and SNU475 cells with a plasmid expressing LGN (pcDNA3.1-myc/His-LGN). Compared with a control plasmid (pcDNA3.1-myc/His-LacZ), pcDNA3.1-myc/His-LGN produced markedly a larger number of colonies in these cells (FIG. 13a). This result was confirmed by three independent experiments.

To further investigate the effect of LGN on cell growth, NIH3T3 cells that stably expressed exogeneous LGN (NIH3T3-LGN cells) were established. NIH3T3-LGN cells showed higher growth rate than control NIH3T3-LacZ cells (FIG. 13b).

3-5. Antisense S-oligonucleotides of LGN Suppressed Growth of Human Hepatoma SNU475 Cells The following five pairs of control (sense) and antisense S-oligonucleotides corresponding to LGN were synthesized and then transfected into SNU423 cells.

Antisense:

```
                            (SEQ ID NO: 38)
antisense 1    5'-CCATCGAGTCATATTA-3';

(SEQ ID NO: 39)
antisense 2    5'-TTCCTCCATCGAGTCA-3';

(SEQ ID NO: 40)
antisense 3    5'-AAATTTTCCTCCATCG-3';

(SEQ ID NO: 41)
antisense 4    5'-AGTCTTACCTGTAACG-3';
and (SEQ ID NO: 42)
antisense 5    5'-GCTTCCATTCTACAAA-3'.
```

Sense:

```
sense 1    5'-TAATATGACTCGATGG-3';    (SEQ ID NO: 43)

sense 2    5'-TGACTCGATGGAGGAA-3';    (SEQ ID NO: 44)

sense 3    5'-CGATGGAGGAAAATTT-3';    (SEQ ID NO: 45)

sense 4    5'-CGTTACAGGTAAGACT-3';    (SEQ ID NO: 46)
and sense 5    5'-TTTGTAGAATGGAAGC-3'.    (SEQ ID NO: 47)
```

Figure 14:
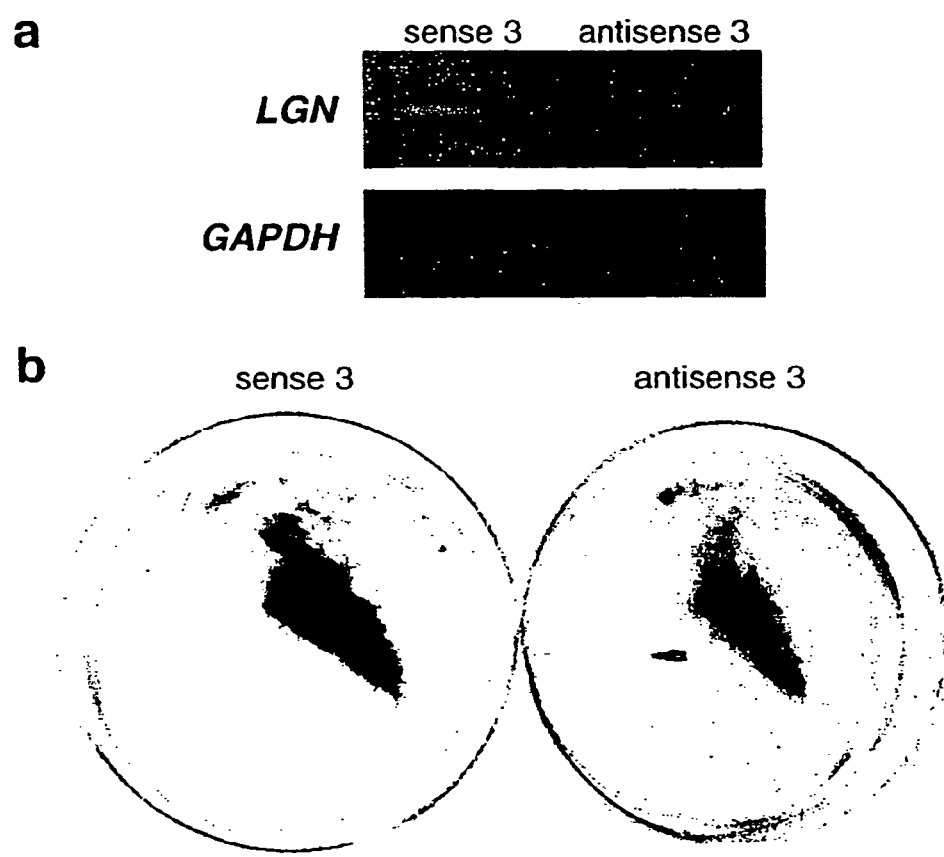
FIGS. 14a and 14b show growth suppression by antisense S-oligonucleotide designated to suppress LGN expression in human hepatoma SNU423 cells.

The antisense S-oligonucleotide encompassing the initiation codon (antisense 3) significantly suppressed expression of LGN compared to control S-oligonucleotide (sense 3) 12 hours after transfection (FIG. 14a). Six days after transfection, the number of surviving cells transfected with antisense 3 were markedly fewer than that with control sense 3 (FIG. 14b). Consistent results were obtained in three independent experiments.

INDUSTRIAL APPLICABILITY

The present invention provides cDNA nucleotide sequences and polypeptide amino acid sequence of DDEFL1, VANGL1 or LGN, which have been found to be commonly up-regulated in hepatocellular carcinomas. Thus, these polypeptides can be used as markers to determine the presence or absence of liver cancers. The information of these nucleotide sequences enables one to design probes and primers to detect or amplify the DDEFL1, VANGL1 or LGN genes. It also enables synthesis of antisense nucleotide sequence that inhibits expression of the DDEFL1, VANGL1 or LGN polypeptides. The amino acid sequence information enables one to prepare antibodies that bind to the DDEFL1, VANGL1 or LGN polypeptides. The probes and primers as well as the antibodies are useful as a reagent for detecting hepatocellular carcinomas. Furthermore, the present inventors demonstrated that suppressing the expression of DDEFL1, VANGL1 or LGN by antisense oligonucleotides markedly decreases growth of HCC cells. Thus, the antisense oligonucleotides can be used to inhibit growth of HCC cells. The present invention also contributes to further clarify the mechanisms of hepatocellular carcinogenesis and to discover molecular targets for development of effective drugs to treat liver cancers.

SEQUENCE LISTING

<160> NUMBER OF SEQ ID NOS: 47

<210> SEQ ID NO 1

-continued

```
<211> LENGTH: 4050
<212> TYPE: DNA
<213> ORGANISM: Homo sapiens

<400> SEQUENCE: 1 gtgcccccg cgctccgctc cggcagctcc acgctcgcgc cgccatgcc ggagcagttc      60 agcgtcgccg agttcctggc cgtcaccgcg gaggacctca gctccccggc tggggccgcc    120
gccttcgccg ccaagatgcc ccggtaccga ggggcggcgc tggcgcggga ggagatcttg    180
gaaggagacc aagccatcct gcagagaata aagaaggctg tgcgggcaat ccatagctcc    240
ggccttggcc atgtggagaa tgaagagcag taccgagagg ccgtggaatc cttaggcaac    300
agccacctgt cccagaacag ccatgagctg tccacaggct tcctaaactt ggccgtgttc    360
acccgcgagg ttgctgcgct cttcaagaac ctgattcaga acttgaacaa cattgtctct    420 ttcccctgg acagtctgat gaaggggcag ctgagggacg tcgacagga ttccaaaaaa     480 cagctggaga aggcatggaa ggactatgaa gccaaaatgg ccaagctgga gaaggagcgc    540
gatcgggcca gggtgacagg agggatccct ggggaggtgg cccaggacat gcagagagag    600
cggcgcatct tccagctgca catgtgtgag tatctgctca aagccgggga gagccagatg    660
aagcaaggtc ctgacttcct tcagagcctc atcaagttct ccacgccca gcacaacttt    720 ttccaagatg gctggaaggc tgcccagagc ctgttcccct tcatcgagaa gctggcggcc    780
tcagtacatg cactccatca ggcccaggag gacgagctac agaagctgac ccagctccgg    840
gactccctcc gagggacact gcagcttgag agcagagagg aacacctgag ccggaagaac    900
tcaggatgtg gctatagcat ccaccagcac caaggcaaca gcagtttgg gacggagaaa    960 gtgggctttc tatacaagaa aagtgacgga attcgaagag tctggcagaa aaggaagtgt   1020
ggagtcaagt atggctgcct gaccatctca cacagcacga taaaccggcc cccggtgaag   1080
ctgaccctgc tgacgtgcca agtgaggcca aaccctgagg agaaaaagtg cttcgacctg   1140
gtgacccaca accggacgta ccactttcag gcagaggacg agcacgagtg tgaggcgtgg   1200
gtgtcagtgt tgcagaacag caaggacgaa gccctgagca cgccttcct cggggagccc   1260 agcgctggcc cggggtcctg ggggtccgcc ggccatgatg gggagccgca cgacctcaca   1320
aagctgctca tcgcggaggt gaagagcagg cctgggaata ccagtgctg cgactgcggg   1380 gctgcagacc ccacgtggct cagcaccaac ctgggcgtgc tcacctgcat ccagtgctcg   1440
ggcgtccacc gcgaactggg cgtgcgcttt tcgcgcatgc agtcactcac cttggacctg   1500 ctgggccccct ccgagttgtt gctggccttg aacatgggaa acacgagctt caatgaggtc   1560
atggaggccc agctaccctc acacggcggc cctaaaccct cagctgagag tgacatgggc   1620
acccgcaggg actacattat ggccaagtat gtggagcata ggtttgcacg ccggtgcaca   1680
cctgagcctc agcgactctg gacagccatt tgcaacaggg acctcctgtc ggtactggag   1740
gcctttgcca atgggcagga cttttggacag ccgctgccag gcctgatgc acaggcacct   1800 gaagaactcg tcttgcattt ggctgtcaaa gtcgccaacc aggcttccct gcctctggtg   1860
gatttcatca tccagaacgg tggtcacctg atgccaaagg ctgctgacgg aacacggct    1920 ctgcactacg cagcactcta caaccagccc gactgcctca agctgctgct gaagggagaa    1980
gctttggttg gcacagtaaa tgaagcaggc gagacagctc tggacatagc caggaagaag    2040
caccacaagg agtgtgagga gctgctggag caggcccagg cggggacctt tgccttccct    2100
ctacatgtgg actactcctg ggtaatttcc acagagcctg gctctgacag tgaggaggat    2160
gaggaagaga agcgctgctt gctgaagctc ccggcccagg ctcactgggc cagtgggagg    2220
```

```
ctggacatca gcaacaagac ctatgagact gtcgccagcc tgggagcagc cacccctcag   2280
ggcgagagtg aggactgtcc cccgcccttg ccagtcaaaa actcttctcg gactttggtc   2340
caagggtgtg caagacatgc cagtggagat cgttctgaag tctccagcct gagttcagag   2400
gcccctgaga cccctgagag cctgggcagt ccagcctcct cctccagtct gatgagcccc   2460
ttggaacctg ggatcccag ccaagcccca cccaactctg aagagggcct ccgagagccc   2520
ccaggcacct ccagacccag cctgacatcc ggaccaccc cttcggagat gtacctcccc   2580
gtcagattca gctccgagag cactcgctcc tatcggcggg gggcgcggag ccctgaagat   2640
ggtccctcag ccaggcagcc tctgcccaga aggaacgtgc cggttggcat cactgaagga   2700
gatggctcaa ggactgggag tctcccagca agttctgtgc aacttttgca agactagctc   2760
cttgctggcc cccacatgcc ccatgctagg ccccaatgtt cagagctggg acttgagctc   2820
acaaaactgg ggagctgaga catttgttct cttggatctc actctctctg tcccttgtgc   2880
ctctgtagct ggccttcttc ctgccacagg ccatgcctct accaaggaca catggccttt   2940
ccctgttagg gctgatggcg gttctttcct atctcattac ccgctagggg cctgggagcc   3000
ctgtggctgg atctgagtgc tcctgagctg gcttcagctg cagaactctc agtccctcat   3060
cagatcgaga ctctatttcc cccgtcagtc tgggggcttc acaagggcag agagccctc   3120
catcactgac ttccagatca gggaccctgc caagtaggga ctgtcttctc agccagccat   3180
ttattagtct aatattcctt cactaaattc caactctatg tctggacctg tgttaggcac   3240
ttcagatacc acacgagtaa gacaagggcc ctgcaggggt ggtcctttgg tggaaagctg   3300
gtcttaaggg ttgggcttgg gaataggcag ggtcagattc cagggcatgg ctctggactc   3360
agctggttta tacctatatg accattacag ttgtctacag atcacatcca ttctggctgg   3420
tcaacatgca tgctgtactg gctgttaaat aaaaatattc tgaatgtcac tccttttgag   3480
ggacagcaca gccttcccta ggcattctcc tatattcccc agccaaattg tagagtcaga   3540
tgcaccaca tttgcctgtg tccttgattt agcaggaagg aaaggaatag tcggggttga   3600
tggatgccca cttctcttct ctttctcttg gtcaactcag gagcctttta gtctgaggga   3660
atggagaggc aaagaaagaa gggagagtaa tagaattggg agggcagaga cttaagggtt   3720
ctgcttccca gccctagaaa ttctatcatt gctcagcccc aatgagaaag cagatacacc   3780
taagccatca tcaaccacta acatctcaac ttgccagttg ctgggtgctg ggccctggca   3840
ggaatgggcc aagccaagca ggggagacta gagagcacca atggccaaca cagctgcctg   3900
gctggggagg ctgtgctgtt tcccctggag acctgactgg tctgtggttc ccacaggaac   3960
agggttgtct tttgagcccc cagtgtctgg tttcattcat ctcagacttg ttatttcact   4020
catctctaat aaaggattgg ggggtcagtt                                    4050
```

<210> SEQ ID NO 2
<211> LENGTH: 903
<212> TYPE: PRT
<213> ORGANISM: Homo sapiens

<400> SEQUENCE: 2

```
Met Pro Glu Gln Phe Ser Val Ala Glu Phe Leu Ala Val Thr Ala Glu
1               5                   10                  15

Asp Leu Ser Ser Pro Ala Gly Ala Ala Ala Phe Ala Ala Lys Met Pro
            20                  25                  30

Arg Tyr Arg Gly Ala Ala Leu Ala Arg Glu Glu Ile Leu Glu Gly Asp
        35                  40                  45
```

-continued

```
Gln Ala Ile Leu Gln Arg Ile Lys Lys Ala Val Arg Ala Ile His Ser
         50                  55                  60

Ser Gly Leu Gly His Val Glu Asn Glu Glu Gln Tyr Arg Glu Ala Val
 65                  70                  75                  80

Glu Ser Leu Gly Asn Ser His Leu Ser Gln Asn Ser His Glu Leu Ser
                 85                  90                  95

Thr Gly Phe Leu Asn Leu Ala Val Phe Thr Arg Glu Val Ala Ala Leu
                100                 105                 110

Phe Lys Asn Leu Ile Gln Asn Leu Asn Asn Ile Val Ser Phe Pro Leu
            115                 120                 125

Asp Ser Leu Met Lys Gly Gln Leu Arg Asp Gly Arg Gln Asp Ser Lys
        130                 135                 140

Lys Gln Leu Glu Lys Ala Trp Lys Asp Tyr Glu Ala Lys Met Ala Lys
145                 150                 155                 160

Leu Glu Lys Glu Arg Asp Arg Ala Arg Val Thr Gly Gly Ile Pro Gly
                165                 170                 175

Glu Val Ala Gln Asp Met Gln Arg Glu Arg Arg Ile Phe Gln Leu His
                180                 185                 190

Met Cys Glu Tyr Leu Leu Lys Ala Gly Glu Ser Gln Met Lys Gln Gly
            195                 200                 205

Pro Asp Phe Leu Gln Ser Leu Ile Lys Phe Phe His Ala Gln His Asn
210                 215                 220

Phe Phe Gln Asp Gly Trp Lys Ala Ala Gln Ser Leu Phe Pro Phe Ile
225                 230                 235                 240

Glu Lys Leu Ala Ala Ser Val His Ala Leu His Gln Ala Gln Glu Asp
                245                 250                 255

Glu Leu Gln Lys Leu Thr Gln Leu Arg Asp Ser Leu Arg Gly Thr Leu
            260                 265                 270

Gln Leu Glu Ser Arg Glu Glu His Leu Ser Arg Lys Asn Ser Gly Cys
        275                 280                 285

Gly Tyr Ser Ile His Gln His Gln Gly Asn Lys Gln Phe Gly Thr Glu
290                 295                 300

Lys Val Gly Phe Leu Tyr Lys Lys Ser Asp Gly Ile Arg Arg Val Trp
305                 310                 315                 320

Gln Lys Arg Lys Cys Gly Val Lys Tyr Gly Cys Leu Thr Ile Ser His
                325                 330                 335

Ser Thr Ile Asn Arg Pro Pro Val Lys Leu Thr Leu Leu Thr Cys Gln
            340                 345                 350

Val Arg Pro Asn Pro Glu Glu Lys Lys Cys Phe Asp Leu Val Thr His
        355                 360                 365

Asn Arg Thr Tyr His Phe Gln Ala Glu Asp Glu His Glu Cys Glu Ala
370                 375                 380

Trp Val Ser Val Leu Gln Asn Ser Lys Asp Glu Ala Leu Ser Ser Ala
385                 390                 395                 400

Phe Leu Gly Glu Pro Ser Ala Gly Pro Gly Ser Trp Gly Ser Ala Gly
                405                 410                 415

His Asp Gly Glu Pro His Asp Leu Thr Lys Leu Leu Ile Ala Glu Val
                420                 425                 430

Lys Ser Arg Pro Gly Asn Ser Gln Cys Cys Asp Cys Gly Ala Ala Asp
            435                 440                 445

Pro Thr Trp Leu Ser Thr Asn Leu Gly Val Leu Thr Cys Ile Gln Cys
        450                 455                 460
```

```
Ser Gly Val His Arg Glu Leu Gly Val Arg Phe Ser Arg Met Gln Ser
465                 470                 475                 480

Leu Thr Leu Asp Leu Leu Gly Pro Ser Glu Leu Leu Ala Leu Asn
        485                 490                 495

Met Gly Asn Thr Ser Phe Asn Glu Val Met Glu Ala Gln Leu Pro Ser
            500                 505                 510

His Gly Gly Pro Lys Pro Ser Ala Glu Ser Asp Met Gly Thr Arg Arg
        515                 520                 525

Asp Tyr Ile Met Ala Lys Tyr Val Glu His Arg Phe Ala Arg Arg Cys
        530                 535                 540

Thr Pro Glu Pro Gln Arg Leu Trp Thr Ala Ile Cys Asn Arg Asp Leu
545                 550                 555                 560

Leu Ser Val Leu Glu Ala Phe Ala Asn Gly Gln Asp Phe Gly Gln Pro
            565                 570                 575

Leu Pro Gly Pro Asp Ala Gln Ala Pro Glu Glu Leu Val Leu His Leu
            580                 585                 590

Ala Val Lys Val Ala Asn Gln Ala Ser Leu Pro Leu Val Asp Phe Ile
        595                 600                 605

Ile Gln Asn Gly Gly His Leu Asp Ala Lys Ala Ala Asp Gly Asn Thr
610                 615                 620

Ala Leu His Tyr Ala Ala Leu Tyr Asn Gln Pro Asp Cys Leu Lys Leu
625                 630                 635                 640

Leu Leu Lys Gly Arg Ala Leu Val Gly Thr Val Asn Glu Ala Gly Glu
            645                 650                 655

Thr Ala Leu Asp Ile Ala Arg Lys Lys His His Lys Glu Cys Glu Glu
                660                 665                 670

Leu Leu Glu Gln Ala Gln Ala Gly Thr Phe Ala Phe Pro Leu His Val
            675                 680                 685

Asp Tyr Ser Trp Val Ile Ser Thr Glu Pro Gly Ser Asp Ser Glu Glu
        690                 695                 700

Asp Glu Glu Glu Lys Arg Cys Leu Leu Lys Leu Pro Ala Gln Ala His
705                 710                 715                 720

Trp Ala Ser Gly Arg Leu Asp Ile Ser Asn Lys Thr Tyr Glu Thr Val
                725                 730                 735

Ala Ser Leu Gly Ala Ala Thr Pro Gln Gly Glu Ser Glu Asp Cys Pro
            740                 745                 750

Pro Pro Leu Pro Val Lys Asn Ser Ser Arg Thr Leu Val Gln Gly Cys
            755                 760                 765

Ala Arg His Ala Ser Gly Asp Arg Ser Glu Val Ser Ser Leu Ser Ser
        770                 775                 780

Glu Ala Pro Glu Thr Pro Glu Ser Leu Gly Ser Pro Ala Ser Ser Ser
785                 790                 795                 800

Ser Leu Met Ser Pro Leu Glu Pro Gly Asp Pro Ser Gln Ala Pro Pro
            805                 810                 815

Asn Ser Glu Glu Gly Leu Arg Glu Pro Pro Gly Thr Ser Arg Pro Ser
            820                 825                 830

Leu Thr Ser Gly Thr Thr Pro Ser Glu Met Tyr Leu Pro Val Arg Phe
            835                 840                 845

Ser Ser Glu Ser Thr Arg Ser Tyr Arg Arg Gly Ala Arg Ser Pro Glu
            850                 855                 860

Asp Gly Pro Ser Ala Arg Gln Pro Leu Pro Arg Arg Asn Val Pro Val
865                 870                 875                 880

Gly Ile Thr Glu Gly Asp Gly Ser Arg Thr Gly Ser Leu Pro Ala Ser
```

```
                885                 890                 895
Ser Val Gln Leu Leu Gln Asp
            900

<210> SEQ ID NO 3
<211> LENGTH: 1879
<212> TYPE: DNA
<213> ORGANISM: Homo sapiens

<400> SEQUENCE: 3
ctcgctcaca aaaaattgag ccggccctgg aggcctgggg ggcgagtccg gttgcgcctc      60
ggagagcgca acaggcagaa tttgttcctg ttgaagagtg gctcctcttc taatttccag    120
actccttgag gttttaggag tctggtaggt gaaattttct acctctaagg agaaacagta    180
cctgctcctt cctcaagcgc aagccctcca ttgctatgga taccgaatcc acttattctg    240
gatattctta ctattcaagt cattcgaaaa aatctcacag acaaggggaa agaactagag    300
agagacacaa gtcaccccgg aataaagacg gcagagggtc agaaaagtct gtcaccattc    360
aacctcccac tggagagccc ctgttgggaa atgattctac tcggacagag gaagttcagg    420
atgacaactg gggagagacc accacggcca tcacaggcac ctcggagcac agcatatccc    480
aagaggacat tgccaggatc agcaaggaca tggaggacag cgtggggctg gattgcaaac    540
gctacctggg cctcaccgtc gcctcttttc ttggacttct agttttcctc accctattg     600 ccttcatcct tttacctccg atcctgtgga gggatgagct ggagccttgt ggcacaattt    660 gtgagggggct ctttatctcc atggcattca aactcctcat tctgctcata gggacctggg    720
cacttttttt ccgcaagcgg agagctgaca tgccacgggt gttttgtgttt cgtgccctt    780 tgttggtcct catctttctc tttgtggttt cctattggct tttttacggg gtccgcattt    840
tggactctcg ggaccggaat taccagggca ttgtgcaata tgcagtctcc cttgtggatg    900
ccctcctctt catccattac ctggccatcg tcctgctgga gctcaggcag ctgcagccca    960
tgttcacgct gcaggtggtc cgctccaccg atggcgagtc ccgcttctac agcctgggac   1020
acctgagtat ccagcgagca gcattggtgg tcctagaaaa ttactacaaa gatttcacca   1080
tctataaccc aaacctccta acagcctcca aattccgagc agccaagcat atggccgggc   1140
tgaaagtcta caatgtagat ggccccagta acaatgccac tggccagtcc cgggccatga   1200
ttgctgcagc tgctcggcgc agggactcaa gccacaacga gttgtattat gaagaggccg   1260
aacatgaacg gcgagtaaag aagcggaaag caaggctggt ggttgcagtg gaagaggcct   1320
tcatccacat tcagcgtctc caggctgagg agcagcagaa agccccaggg gaggtgatgg   1380 acccctaggga ggccgcccag gccattttcc cctccatggc cagggctctc cagaagtacc   1440
tgcgcatcac ccggcagcag aactaccaca gcatggagag catcctgcag cacctggcct   1500
tctgcatcac caacgcatg accccccaagg ccttcctaga acggtaccte agtgcgggcc   1560 ccaccctgca atatgacaag gaccgctggc tctctacaca gtggaggctt gtcagtgatg   1620
aggctgtgac taatggatta cgggatggaa ttgtgttcgt ccttaagtgc ttggacttca   1680
gcctcgtagt caatgtgaag aaaattccat tcatcatact ctctgaagag ttcatagacc   1740
ccaaatctca caaatttgtc cttcgcttac agtctgagac atccgtttaa aagttctata   1800
tttgtggctt tattaaaaaa aaaagaaaaa tatatagaga gatatgcaaa aaaaataaaa   1860
gacaaaaaca aaaaaaaaa                                                 1879

<210> SEQ ID NO 4
```

<211> LENGTH: 524
<212> TYPE: PRT
<213> ORGANISM: Homo sapiens

<400> SEQUENCE: 4

```
Met Asp Thr Glu Ser Thr Tyr Ser Gly Tyr Ser Tyr Ser Ser His
1               5                   10                  15

Ser Lys Lys Ser His Arg Gln Gly Glu Arg Thr Arg Glu Arg His Lys
            20                  25                  30

Ser Pro Arg Asn Lys Asp Gly Arg Gly Ser Glu Lys Ser Val Thr Ile
            35                  40                  45

Gln Pro Pro Thr Gly Glu Pro Leu Leu Gly Asn Asp Ser Thr Arg Thr
50                  55                  60

Glu Glu Val Gln Asp Asp Asn Trp Gly Glu Thr Thr Thr Ala Ile Thr
65                  70                  75                  80

Gly Thr Ser Glu His Ser Ile Ser Gln Glu Asp Ile Ala Arg Ile Ser
                85                  90                  95

Lys Asp Met Glu Asp Ser Val Gly Leu Asp Cys Lys Arg Tyr Leu Gly
                100                 105                 110

Leu Thr Val Ala Ser Phe Leu Gly Leu Leu Val Phe Leu Thr Pro Ile
            115                 120                 125

Ala Phe Ile Leu Leu Pro Pro Ile Leu Trp Arg Asp Glu Leu Glu Pro
130                 135                 140

Cys Gly Thr Ile Cys Glu Gly Leu Phe Ile Ser Met Ala Phe Lys Leu
145                 150                 155                 160

Leu Ile Leu Leu Ile Gly Thr Trp Ala Leu Phe Arg Lys Arg Arg
                165                 170                 175

Ala Asp Met Pro Arg Val Phe Val Phe Arg Ala Leu Leu Leu Val Leu
                180                 185                 190

Ile Phe Leu Phe Val Val Ser Tyr Trp Leu Phe Tyr Gly Val Arg Ile
            195                 200                 205

Leu Asp Ser Arg Asp Arg Asn Tyr Gln Gly Ile Val Gln Tyr Ala Val
210                 215                 220

Ser Leu Val Asp Ala Leu Leu Phe Ile His Tyr Leu Ala Ile Val Leu
225                 230                 235                 240

Leu Glu Leu Arg Gln Leu Gln Pro Met Phe Thr Leu Gln Val Val Arg
                245                 250                 255

Ser Thr Asp Gly Glu Ser Arg Phe Tyr Ser Leu Gly His Leu Ser Ile
                260                 265                 270

Gln Arg Ala Ala Leu Val Val Leu Glu Asn Tyr Tyr Lys Asp Phe Thr
            275                 280                 285

Ile Tyr Asn Pro Asn Leu Leu Thr Ala Ser Lys Phe Arg Ala Ala Lys
290                 295                 300

His Met Ala Gly Leu Lys Val Tyr Asn Val Asp Gly Pro Ser Asn Asn
305                 310                 315                 320

Ala Thr Gly Gln Ser Arg Ala Met Ile Ala Ala Ala Arg Arg Arg
                325                 330                 335

Asp Ser Ser His Asn Glu Leu Tyr Tyr Glu Ala Glu His Glu Arg
            340                 345                 350

Arg Val Lys Lys Arg Lys Ala Arg Leu Val Val Ala Val Glu Glu Ala
            355                 360                 365

Phe Ile His Ile Gln Arg Leu Gln Ala Glu Glu Gln Lys Ala Pro
370                 375                 380

Gly Glu Val Met Asp Pro Arg Glu Ala Ala Gln Ala Ile Phe Pro Ser
```

```
                385                 390                 395                 400
            Met Ala Arg Ala Leu Gln Lys Tyr Leu Arg Ile Thr Arg Gln Gln Asn
                            405                 410                 415

Tyr His Ser Met Glu Ser Ile Leu Gln His Leu Ala Phe Cys Ile Thr
                        420                 425                 430

Asn Gly Met Thr Pro Lys Ala Phe Leu Glu Arg Tyr Leu Ser Ala Gly
                    435                 440                 445

Pro Thr Leu Gln Tyr Asp Lys Asp Arg Trp Leu Ser Thr Gln Trp Arg
                450                 455                 460

Leu Val Ser Asp Glu Ala Val Thr Asn Gly Leu Arg Asp Gly Ile Val
            465                 470                 475                 480

Phe Val Leu Lys Cys Leu Asp Phe Ser Leu Val Val Asn Val Lys Lys
                            485                 490                 495

Ile Pro Phe Ile Ile Leu Ser Glu Glu Phe Ile Asp Pro Lys Ser His
                        500                 505                 510

Lys Phe Val Leu Arg Leu Gln Ser Glu Thr Ser Val
                    515                 520

<210> SEQ ID NO 5
<211> LENGTH: 2336
<212> TYPE: DNA
<213> ORGANISM: Homo sapiens

<400> SEQUENCE: 5
ggcacgagga agaatcagga gcttaggatg tattaacacc aactcattaa tatactaacc      60
ggacaatgtt ctacaaacaa ttctacattg taaaggactg gattggcaca aaataaaata     120
atttattttt attcagctta taatatgact cgatggagga aaatttgata agcatgagag     180
aagaccattc ttttcatgtt cgttacagaa tggaagcttc ttgcctagag ctggccttgg     240
aaggggaacg tctatgtaaa tcaggagact gccgcgctgg cgtgtcattc tttgaagctg     300
cagttcaagt tggaactgaa gacctaaaaa cacttagcgc tatttacagc cagttgggca     360
atgcttattt ctatttgcat gattatgcca aagcattaga atatcaccat catgatttaa     420
cccttgcaag gactattgga gaccagctgg gggaagcgaa agctagtggt aatctgggaa     480
acaccttaaa agttcttggg aattttgacg aagcccatagt ttgttgtcag cgacacctag     540
atatttccag agagcttaat gacaaggtgg agaagcaag agcactttac aatcttggga     600
atgtgtatca tgccaaaggg aaaagttttg gttgccctgg tccccaggat gtaggagaat     660
ttccagaaga agtgagagat gctctgcagg cagccgtgga ttttatgag gaaaacctat     720 cattagtgac tgctttgggt gaccgagcgg cacaaggacg tgcctttgga atcttggaa     780 acacacatta cctccttggc aacttcaggg atgcagttat agctcatgag cagcgtctcc     840
ttattgcaaa agaatttgga gataaagcag ctgaaagaag agcatatagc aaccttggaa     900
atgcatatat atttcttggt gaatttgaaa ctgcctcgga atactacaag aagacactac     960
tgttggcccg acagcttaaa gaccgagctg tagaagcaca gtcttgttac agtcttggaa    1020
atacatatac tttacttcaa gactatgaaa aggccattga ttatcatctg aagcacttag    1080
caattgctca agagctgaat gatagaattg gtgaaggaag agcatgttgg agcttaggaa    1140
atgcatacac agcactagga aatcatgatc aagcaatgca ttttgctgaa aagcacttgg    1200
aaatttcaag agaggttggg gataaaagtg gtgaactaac agcacgactt aatctctcag    1260 acccttcaaat ggttcttggt ctgagctaca gcacaaataa ctccataatg tctgaaaata    1320
ctgaaattga tagcagtttg aatggtgtac tccccaagtt gggacgccgg catagtatgg    1380
```

-continued

```
aaaatatgga acttatgaag ttaacaccag aaaaggtaca gaactggaac agtgaaattc    1440
ttgctaagca aaaacctctt attgccaaac cttctgcaaa gctactcttt gtcaacagac    1500
tgaaggggaa aaaatacaaa acgaattcct ccactaaagt tctccaagat gccagtaatt    1560
ctattgacca ccgaattcca aattctcaga ggaaaatcag tgcagatact attggagatg    1620
aagggttctt tgacttatta agccgatttc aaagcaatag gatggatgat cagagatgtt    1680
gcttacaaga aagaactgc catacagctt caacaacaac ttcttccact cccctaaaa     1740 tgatgctaaa aacatcatct gttcctgtgg tatcccccaa cacgGatgag ttttagatc     1800 ttcttgccag ctcacagagt cgccgtctgg atgaccagag ggctagtttc agtaatttgc    1860
cagggcttcg tctaacacaa aacagccagt cggtacttag ccacctgatg actaatgaca    1920
acaaagaggc tgatgaagat ttctttgaca tccttgtaaa atgtcaagga tccagattag    1980
atgatcaaag atgtgctcca ccacctgcta ccacaaaggg tccgacagta ccagatgaag    2040 acttttcag cctatttta cggtcccagg gaaagagaat ggatgaacag agagttcttt       2100
tacaaagaga tcaaaacaga gacactgact ttgggctaaa ggacttttg caaaataatg       2160 ctttgttgga gtttaaaaat tcagggaaaa aatcggcaga ccattagtta ctatggattt     2220
attttttttc ctttcaaaca cggtaaggaa acaatctatt actttttttcc ttaaaaggag   2280 aatttatagc actgtaatac agcttaaaat attttttagaa tgatgtaaat agttaa      2336
```

<210> SEQ ID NO 6
<211> LENGTH: 677
<212> TYPE: PRT
<213> ORGANISM: Homo sapiens

<400> SEQUENCE: 6

```
Met Arg Glu Asp His Ser Phe His Val Arg Tyr Arg Met Glu Ala Ser
1               5                   10                  15

Cys Leu Glu Leu Ala Leu Glu Gly Glu Arg Leu Cys Lys Ser Gly Asp
            20                  25                  30

Cys Arg Ala Gly Val Ser Phe Phe Glu Ala Ala Val Gln Val Gly Thr
        35                  40                  45

Glu Asp Leu Lys Thr Leu Ser Ala Ile Tyr Ser Gln Leu Gly Asn Ala
    50                  55                  60

Tyr Phe Tyr Leu His Asp Tyr Ala Lys Ala Leu Glu Tyr His His His
65                  70                  75                  80

Asp Leu Thr Leu Ala Arg Thr Ile Gly Asp Gln Leu Gly Glu Ala Lys
                85                  90                  95

Ala Ser Gly Asn Leu Gly Asn Thr Leu Lys Val Leu Gly Asn Phe Asp
            100                 105                 110

Glu Ala Ile Val Cys Cys Gln Arg His Leu Asp Ile Ser Arg Glu Leu
        115                 120                 125

Asn Asp Lys Val Gly Glu Ala Arg Ala Leu Tyr Asn Leu Gly Asn Val
    130                 135                 140

Tyr His Ala Lys Gly Lys Ser Phe Gly Cys Pro Gly Pro Gln Asp Val
145                 150                 155                 160

Gly Glu Phe Pro Glu Glu Val Arg Asp Ala Leu Gln Ala Ala Val Asp
                165                 170                 175

Phe Tyr Glu Glu Asn Leu Ser Leu Val Thr Ala Leu Gly Asp Arg Ala
            180                 185                 190

Ala Gln Gly Arg Ala Phe Gly Asn Leu Gly Asn Thr His Tyr Leu Leu
        195                 200                 205
```

```
Gly Asn Phe Arg Asp Ala Val Ile Ala His Glu Gln Arg Leu Leu Ile
    210                 215                 220

Ala Lys Glu Phe Gly Asp Lys Ala Ala Glu Arg Arg Ala Tyr Ser Asn
225                 230                 235                 240

Leu Gly Asn Ala Tyr Ile Phe Leu Gly Glu Phe Glu Thr Ala Ser Glu
                245                 250                 255

Tyr Tyr Lys Lys Thr Leu Leu Leu Ala Arg Gln Leu Lys Asp Arg Ala
            260                 265                 270

Val Glu Ala Gln Ser Cys Tyr Ser Leu Gly Asn Thr Tyr Thr Leu Leu
        275                 280                 285

Gln Asp Tyr Glu Lys Ala Ile Asp Tyr His Leu Lys His Leu Ala Ile
    290                 295                 300

Ala Gln Glu Leu Asn Asp Arg Ile Gly Glu Gly Arg Ala Cys Trp Ser
305                 310                 315                 320

Leu Gly Asn Ala Tyr Thr Ala Leu Gly Asn His Asp Gln Ala Met His
                325                 330                 335

Phe Ala Glu Lys His Leu Glu Ile Ser Arg Glu Val Gly Asp Lys Ser
            340                 345                 350

Gly Glu Leu Thr Ala Arg Leu Asn Leu Ser Asp Leu Gln Met Val Leu
        355                 360                 365

Gly Leu Ser Tyr Ser Thr Asn Asn Ser Ile Met Ser Glu Asn Thr Glu
    370                 375                 380

Ile Asp Ser Ser Leu Asn Gly Val Leu Pro Lys Leu Gly Arg Arg His
385                 390                 395                 400

Ser Met Glu Asn Met Glu Leu Met Lys Leu Thr Pro Glu Lys Val Gln
                405                 410                 415

Asn Trp Asn Ser Glu Ile Leu Ala Lys Gln Lys Pro Leu Ile Ala Lys
            420                 425                 430

Pro Ser Ala Lys Leu Leu Phe Val Asn Arg Leu Lys Gly Lys Lys Tyr
        435                 440                 445

Lys Thr Asn Ser Ser Thr Lys Val Leu Gln Asp Ala Ser Asn Ser Ile
    450                 455                 460

Asp His Arg Ile Pro Asn Ser Gln Arg Lys Ile Ser Ala Asp Thr Ile
465                 470                 475                 480

Gly Asp Glu Gly Phe Phe Asp Leu Leu Ser Arg Phe Gln Ser Asn Arg
                485                 490                 495

Met Asp Asp Gln Arg Cys Cys Leu Gln Glu Lys Asn Cys His Thr Ala
            500                 505                 510

Ser Thr Thr Thr Ser Ser Thr Pro Pro Lys Met Met Leu Lys Thr Ser
        515                 520                 525

Ser Val Pro Val Val Ser Pro Asn Thr Asp Glu Phe Leu Asp Leu Leu
    530                 535                 540

Ala Ser Ser Gln Ser Arg Arg Leu Asp Asp Gln Arg Ala Ser Phe Ser
545                 550                 555                 560

Asn Leu Pro Gly Leu Arg Leu Thr Gln Asn Ser Gln Ser Val Leu Ser
                565                 570                 575

His Leu Met Thr Asn Asp Asn Lys Glu Ala Asp Glu Asp Phe Phe Asp
            580                 585                 590

Ile Leu Val Lys Cys Gln Gly Ser Arg Leu Asp Asp Gln Arg Cys Ala
        595                 600                 605

Pro Pro Pro Ala Thr Thr Lys Gly Pro Thr Val Pro Asp Glu Asp Phe
    610                 615                 620
```

Phe Ser Leu Ile Leu Arg Ser Gln Gly Lys Arg Met Asp Glu Gln Arg
625                 630                 635                 640

Val Leu Leu Gln Arg Asp Gln Asn Arg Asp Thr Asp Phe Gly Leu Lys
                645                 650                 655

Asp Phe Leu Gln Asn Asn Ala Leu Leu Glu Phe Lys Asn Ser Gly Lys
                660                 665                 670

Lys Ser Ala Asp His
        675

<210> SEQ ID NO 7
<211> LENGTH: 22
<212> TYPE: DNA
<213> ORGANISM: Artificial
<220> FEATURE:
<223> OTHER INFORMATION: an artificially synthesized primer sequence

<400> SEQUENCE: 7
acaacagcct caagatcatc ag                                           22

<210> SEQ ID NO 8
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 8
ggtccaccac tgacacgttg                                              20

<210> SEQ ID NO 9
<211> LENGTH: 22
<212> TYPE: DNA
<213> ORGANISM: Artificial
<220> FEATURE:
<223> OTHER INFORMATION: an artificially synthesized primer sequence

<400> SEQUENCE: 9
agctgagaca tttgttctct tg                                           22

<210> SEQ ID NO 10
<211> LENGTH: 22
<212> TYPE: DNA
<213> ORGANISM: Artificial
<220> FEATURE:
<223> OTHER INFORMATION: an artificially synthesized primer sequence

<400> SEQUENCE: 10
tataaaccag ctgagtccag ag                                           22

<210> SEQ ID NO 11
<211> LENGTH: 22
<212> TYPE: DNA
<213> ORGANISM: Artificial
<220> FEATURE:
<223> OTHER INFORMATION: an artificially synthesized primer sequence

<400> SEQUENCE: 11
ctcacttggc acgtcagcag gg                                           22

<210> SEQ ID NO 12
<211> LENGTH: 10
<212> TYPE: DNA
<213> ORGANISM: Homo sapiens

<400> SEQUENCE: 12

```
cccgccatgc                                                           10

<210> SEQ ID NO 13
<211> LENGTH: 16
<212> TYPE: DNA
<213> ORGANISM: Artificial
<220> FEATURE:
<223> OTHER INFORMATION: an artificially synthesized oligonucleotide
      sequence

<400> SEQUENCE: 13
tgctccggca tggcgg                                                    16

<210> SEQ ID NO 14
<211> LENGTH: 16
<212> TYPE: DNA
<213> ORGANISM: Artificial
<220> FEATURE:
<223> OTHER INFORMATION: an artificially synthesized oligonucleotide
      sequence

<400> SEQUENCE: 14
gctgaactgc tccggc                                                    16

<210> SEQ ID NO 15
<211> LENGTH: 16
<212> TYPE: DNA
<213> ORGANISM: Artificial
<220> FEATURE:
<223> OTHER INFORMATION: an artificially synthesized oligonucleotide
      sequence

<400> SEQUENCE: 15
tccaagatct cctccc                                                    16

<210> SEQ ID NO 16
<211> LENGTH: 16
<212> TYPE: DNA
<213> ORGANISM: Artificial
<220> FEATURE:
<223> OTHER INFORMATION: an artificially synthesized oligonucleotide
      sequence

<400> SEQUENCE: 16
tctccttcca agatct                                                    16

<210> SEQ ID NO 17
<211> LENGTH: 16
<212> TYPE: DNA
<213> ORGANISM: Artificial
<220> FEATURE:
<223> OTHER INFORMATION: an artificially synthesized oligonucleotide
      sequence

<400> SEQUENCE: 17
gcgctgagcc ggcctc                                                    16

<210> SEQ ID NO 18
<211> LENGTH: 16
<212> TYPE: DNA
<213> ORGANISM: Artificial
<220> FEATURE:
<223> OTHER INFORMATION: an artificially synthesized oligonucleotide
      sequence

<400> SEQUENCE: 18
```

```
cctcacctcc tcccgc                                                          16
```

<210> SEQ ID NO 19
<211> LENGTH: 16
<212> TYPE: DNA
<213> ORGANISM: Artificial
<220> FEATURE:
<223> OTHER INFORMATION: an artificially synthesized oligonucleotide
      sequence

<400> SEQUENCE: 19

```
ccgccatgcc ggagca                                                          16
```

<210> SEQ ID NO 20
<211> LENGTH: 16
<212> TYPE: DNA
<213> ORGANISM: Artificial
<220> FEATURE:
<223> OTHER INFORMATION: an artificially synthesized oligonucleotide
      sequence

<400> SEQUENCE: 20

```
gccggagcag ttcagc                                                          16
```

<210> SEQ ID NO 21
<211> LENGTH: 16
<212> TYPE: DNA
<213> ORGANISM: Artificial
<220> FEATURE:
<223> OTHER INFORMATION: an artificially synthesized oligonucleotide
      sequence

<400> SEQUENCE: 21

```
gggaggagat cttgga                                                          16
```

<210> SEQ ID NO 22
<211> LENGTH: 16
<212> TYPE: DNA
<213> ORGANISM: Artificial
<220> FEATURE:
<223> OTHER INFORMATION: an artificially synthesized oligonucleotide
      sequence

<400> SEQUENCE: 22

```
agatcttgga aggaga                                                          16
```

<210> SEQ ID NO 23
<211> LENGTH: 16
<212> TYPE: DNA
<213> ORGANISM: Artificial
<220> FEATURE:
<223> OTHER INFORMATION: an artificially synthesized oligonucleotide
      sequence

<400> SEQUENCE: 23

```
gaggccggct cagcgc                                                          16
```

<210> SEQ ID NO 24
<211> LENGTH: 16
<212> TYPE: DNA
<213> ORGANISM: Artificial
<220> FEATURE:
<223> OTHER INFORMATION: an artificially synthesized oligonucleotide
      sequence

<400> SEQUENCE: 24

```
gcgggaggag gtgagg                                                          16
```

<210> SEQ ID NO 25
<211> LENGTH: 23
<212> TYPE: DNA
<213> ORGANISM: Artificial
<220> FEATURE:
<223> OTHER INFORMATION: an artificially synthesized primer sequence

<400> SEQUENCE: 25
gagttgtatt atgaagaggc cga                                           23

<210> SEQ ID NO 26
<211> LENGTH: 23
<212> TYPE: DNA
<213> ORGANISM: Artificial
<220> FEATURE:
<223> OTHER INFORMATION: an artificially synthesized primer sequence

<400> SEQUENCE: 26
atgtctcaga ctgtaagcga agg                                           23

<210> SEQ ID NO 27
<211> LENGTH: 28
<212> TYPE: DNA
<213> ORGANISM: Artificial
<220> FEATURE:
<223> OTHER INFORMATION: an artificially synthesized primer sequence

<400> SEQUENCE: 27
tgtcagctct ccgcttgcgg aaaaaaag                                      28

<210> SEQ ID NO 28
<211> LENGTH: 16
<212> TYPE: DNA
<213> ORGANISM: Artificial
<220> FEATURE:
<223> OTHER INFORMATION: an artificially synthesized oligonucleotide
      sequence

<400> SEQUENCE: 28
gtatccatag caatgg                                                   16

<210> SEQ ID NO 29
<211> LENGTH: 16
<212> TYPE: DNA
<213> ORGANISM: Artificial
<220> FEATURE:
<223> OTHER INFORMATION: an artificially synthesized oligonucleotide
      sequence

<400> SEQUENCE: 29
tggattgggt atccat                                                   16

<210> SEQ ID NO 30
<211> LENGTH: 16
<212> TYPE: DNA
<213> ORGANISM: Artificial
<220> FEATURE:
<223> OTHER INFORMATION: an artificially synthesized oligonucleotide
      sequence

<400> SEQUENCE: 30
taagtggatt gggtat                                                   16

<210> SEQ ID NO 31
<211> LENGTH: 16

```
<212> TYPE: DNA
<213> ORGANISM: Artificial
<220> FEATURE:
<223> OTHER INFORMATION: an artificially synthesized oligonucleotide
      sequence

<400> SEQUENCE: 31
actcctacct gcctgt                                                      16

<210> SEQ ID NO 32
<211> LENGTH: 16
<212> TYPE: DNA
<213> ORGANISM: Artificial
<220> FEATURE:
<223> OTHER INFORMATION: an artificially synthesized oligonucleotide
      sequence

<400> SEQUENCE: 32
ccattgctat ggatac                                                      16

<210> SEQ ID NO 33
<211> LENGTH: 16
<212> TYPE: DNA
<213> ORGANISM: Artificial
<220> FEATURE:
<223> OTHER INFORMATION: an artificially synthesized oligonucleotide
      sequence

<400> SEQUENCE: 33
atggataccc aatcca                                                      16

<210> SEQ ID NO 34
<211> LENGTH: 16
<212> TYPE: DNA
<213> ORGANISM: Artificial
<220> FEATURE:
<223> OTHER INFORMATION: an artificially synthesized oligonucleotide
      sequence

<400> SEQUENCE: 34
atacccaatc cactta                                                      16

<210> SEQ ID NO 35
<211> LENGTH: 16
<212> TYPE: DNA
<213> ORGANISM: Artificial
<220> FEATURE:
<223> OTHER INFORMATION: an artificially synthesized oligonucleotide
      sequence

<400> SEQUENCE: 35
acaggcaggt aggagt                                                      16

<210> SEQ ID NO 36
<211> LENGTH: 22
<212> TYPE: DNA
<213> ORGANISM: Artificial
<220> FEATURE:
<223> OTHER INFORMATION: an artificially synthesized primer sequence

<400> SEQUENCE: 36
atctgaagca cttagcaatt gc                                               22

<210> SEQ ID NO 37
<211> LENGTH: 21
<212> TYPE: DNA
<213> ORGANISM: Artificial
```

```
<220> FEATURE:
<223> OTHER INFORMATION: an artificially synthesized primer sequence

<400> SEQUENCE: 37
ctgtagctca gaccaagaac c                                              21

<210> SEQ ID NO 38
<211> LENGTH: 16
<212> TYPE: DNA
<213> ORGANISM: Artificial
<220> FEATURE:
<223> OTHER INFORMATION: an artificially synthesized oligonucleotide
      sequence

<400> SEQUENCE: 38
ccatcgagtc atatta                                                    16

<210> SEQ ID NO 39
<211> LENGTH: 16
<212> TYPE: DNA
<213> ORGANISM: Artificial
<220> FEATURE:
<223> OTHER INFORMATION: an artificially synthesized oligonucleotide
      sequence

<400> SEQUENCE: 39
ttcctccatc gagtca                                                    16

<210> SEQ ID NO 40
<211> LENGTH: 16
<212> TYPE: DNA
<213> ORGANISM: Artificial
<220> FEATURE:
<223> OTHER INFORMATION: an artificially synthesized oligonucleotide
      equenece

<400> SEQUENCE: 40
aaatttccct ccatcg                                                    16

<210> SEQ ID NO 41
<211> LENGTH: 16
<212> TYPE: DNA
<213> ORGANISM: Artificial
<220> FEATURE:
<223> OTHER INFORMATION: an artificially synthesized oligonucleotide
      sequence

<400> SEQUENCE: 41
agtcttacct gtaacg                                                    16

<210> SEQ ID NO 42
<211> LENGTH: 16
<212> TYPE: DNA
<213> ORGANISM: Artificial
<220> FEATURE:
<223> OTHER INFORMATION: an artificially synthesized oligonucleotide
      sequence

<400> SEQUENCE: 42
gcttccattc tacaaa                                                    16

<210> SEQ ID NO 43
<211> LENGTH: 16
<212> TYPE: DNA
<213> ORGANISM: Artificial
<220> FEATURE:
<223> OTHER INFORMATION: an artificially synthesized oligonucleotide
```

-continued

```
<400> SEQUENCE: 43
taatatgact cgatgg                                                 16

<210> SEQ ID NO 44
<211> LENGTH: 16
<212> TYPE: DNA
<213> ORGANISM: Artificial
<220> FEATURE:
<223> OTHER INFORMATION: an artificially synthesized oligonucleotide
      sequence

<400> SEQUENCE: 44
tgactcgatg gaggaa                                                 16

<210> SEQ ID NO 45
<211> LENGTH: 16
<212> TYPE: DNA
<213> ORGANISM: Artificial
<220> FEATURE:
<223> OTHER INFORMATION: an artificially synthesized oligonucleotide
      sequence

<400> SEQUENCE: 45
cgatggagga aaattt                                                 16

<210> SEQ ID NO 46
<211> LENGTH: 16
<212> TYPE: DNA
<213> ORGANISM: Artificial
<220> FEATURE:
<223> OTHER INFORMATION: an artificially synthesized oligonucleotide
      sequence

<400> SEQUENCE: 46
cgttacaggt aagact                                                 16

<210> SEQ ID NO 47
<211> LENGTH: 16
<212> TYPE: DNA
<213> ORGANISM: Artificial
<220> FEATURE:
<223> OTHER INFORMATION: an artificially synthesized oligonucleotide
      sequence

<400> SEQUENCE: 47
tttgtagaat ggaagc                                                 16
```

The invention claimed is:

1. An isolated nucleic acid selected from the group consisting of:
   (a) a nucleic acid comprising the nucleotide sequence of SEQ ID NO: 1,
   (b) a nucleic acid encoding a polypeptide comprising the amino acid sequence of SEQ ID NO: 2, and
   (c) a nucleic acid comprising a strand that hybridizes under conditions of high stringency, said conditions comprising the steps of hybridizing and washing at 65° C., 2×SSC, 0,1% SDS, to the entirety of an open reading frame extending from nucleotide 46 to nucleotide 2754 of the nucleotide sequence consisting of SEQ ID NO: 1 or the complement thereof, wherein the nucleic acid encodes a protein having cell proliferative activity.

2. A vector carrying the nucleic acid of claim 1.

3. An isolated transformant carrying the nucleic acid of claim 1 or the vector of claim 2.

4. A method of producing a polypeptide, the method comprising culturing the transformant of claim 3 in a culture, expressing the polypeptide in the transformant, and recovering the polypeptide from the culture.

5. A reagent for detecting hepatocellular carcinomas, comprising a nucleic acid comprising a strand that hybridizes under conditions of high stringency, said conditions comprising the steps of hybridizing and washing at 65° C. 2×SSC, 0,1% SDS, to the entirety of an open reading frame extending from nucleotide 46 to nucleotide 2754 of the nucleotide sequence consisting of SEQ ID NO: 1, or to the complement thereof.

* * * * *

UNITED STATES PATENT AND TRADEMARK OFFICE
CERTIFICATE OF CORRECTION

PATENT NO.         : 7,345,156 B2
APPLICATION NO.    : 10/490605
DATED              : March 18, 2008
INVENTOR(S)        : Nakamura et al.

It is certified that error appears in the above-identified patent and that said Letters Patent is hereby corrected as shown below:

At Column 22, line 58, please delete the Sequence Listing which continues through Column 54 and replace it with the following:

SEQUENCE LISTING

<110>  NAKAMURA, YUSUKE
      FURUKAWA, YOICHI

<120>  HEPATOCELLULAR CARCINOMA-RELATED GENES AND POLYPEPTIDES, AND METHOD FOR DETECTING HEPATOCELLULAR CARCINOMAS

<130>  25371-029NATL/SEN-A0121P-US

<140>  10/490, 605
<141>  2002-09-25

<150>  PCT/JP02/09873
<151>  2002-09-25

<150>  US 60/324,261
<151>  2001-09-25

<150>  CA 2, 399, 569
<151>  2002-08-23

<160>  48

<170>  PatentIn version 3.1

<210>  1
<211>  4050
<212>  DNA
<213>  Homo sapiens

<400>  1
gtgcccccg  cgctccgctc  cggcagctcc  acgctcgcgc  ccgccatgcc  ggagcagttc        60
agcgtcgccg  agttcctggc  cgtcaccgcg  gaggacctca  gctccccggc  tggggccgcc       120
gccttcgccg  ccaagatgcc  ccggtaccga  ggggcggcgc  tggcgcggga  ggagatcttg       180

UNITED STATES PATENT AND TRADEMARK OFFICE
CERTIFICATE OF CORRECTION

PATENT NO. : 7,345,156 B2  
APPLICATION NO. : 10/490605  
DATED : March 18, 2008  
INVENTOR(S) : Nakamura et al.

It is certified that error appears in the above-identified patent and that said Letters Patent is hereby corrected as shown below:

| | | | | | | |
|---|---|---|---|---|---|---|
| gaaggagacc | aagccatcct | gcagagaata | aagaaggctg | tgcgggcaat | ccatagctcc | 240 |
| ggccttggcc | atgtggagaa | tgaagagcag | taccgagagg | ccgtggaatc | cttaggcaac | 300 |
| agccacctgt | cccagaacag | ccatgagctg | tccacaggct | tcctaaactt | ggccgtgttc | 360 |
| acccgcgagg | ttgctgcgct | cttcaagaac | ctgattcaga | acttgaacaa | cattgtctct | 420 |
| ttcccctgg | acagtctgat | gaaggggcag | ctgagggacg | gtcgacagga | ttccaaaaaa | 480 |
| cagctggaga | aggcatggaa | ggactatgaa | gccaaaatgg | ccaagctgga | gaaggagcgc | 540 |
| gatcgggcca | gggtgacagg | agggatccct | ggggaggtgg | cccaggacat | gcagagagag | 600 |
| cggcgcatct | tccagctgca | catgtgtgag | tatctgctca | aagccgggga | gagccagatg | 660 |
| aagcaaggtc | ctgacttcct | tcagagcctc | atcaagttct | tccacgccca | gcacaacttt | 720 |
| ttccaagatg | gctggaaggc | tgcccagagc | ctgttcccct | tcatcgagaa | gctggcggcc | 780 |
| tcagtacatg | cactccatca | ggcccaggag | gacgagctac | agaagctgac | ccagctccgg | 840 |
| gactccctcc | gagggacact | gcagcttgag | agcagagagg | aacacctgag | ccggaagaac | 900 |
| tcaggatgtg | gctatagcat | ccaccagcac | caaggcaaca | agcagtttgg | gacggagaaa | 960 |
| gtgggctttc | tatacaagaa | aagtgacgga | attcgaagag | tctggcagaa | aaggaagtgt | 1020 |
| ggagtcaagt | atggctgcct | gaccatctca | cacagcacga | taaaccggcc | cccggtgaag | 1080 |
| ctgaccctgc | tgacgtgcca | agtgaggcca | aaccctgagg | agaaaaagtg | cttcgacctg | 1140 |
| gtgacccaca | accggacgta | ccactttcag | gcagaggacg | agcacgagtg | tgaggcgtgg | 1200 |
| gtgtcagtgt | tgcagaacag | caaggacgaa | gccctgagca | gcgccttcct | cggggagccc | 1260 |
| agcgctggcc | cggggtcctg | ggggtccgcc | ggccatgatg | gggagccgca | cgacctcaca | 1320 |
| aagctgctca | tcgcggaggt | gaagagcagg | cctgggaata | gccagtgctg | cgactgcggg | 1380 |

UNITED STATES PATENT AND TRADEMARK OFFICE
CERTIFICATE OF CORRECTION

PATENT NO.      : 7,345,156 B2                          Page 3 of 32
APPLICATION NO. : 10/490605
DATED           : March 18, 2008
INVENTOR(S)     : Nakamura et al.

It is certified that error appears in the above-identified patent and that said Letters Patent is hereby corrected as shown below:

| | | | | | |
|---|---|---|---|---|---|
| gctgcagacc | ccacgtggct | cagcaccaac | ctgggcgtgc | tcacctgcat | ccagtgctcg | 1440 |
| ggcgtccacc | gcgaactggg | cgtgcgcttt | tcgcgcatgc | agtcactcac | cttggacctg | 1500 |
| ctgggcccct | ccgagttgtt | gctggccttg | aacatgggaa | acacgagctt | caatgaggtc | 1560 |
| atggaggccc | agctaccctc | acacggcggc | cctaaaccct | cagctgagag | tgacatgggc | 1620 |
| acccgcaggg | actacattat | ggccaagtat | gtggagaata | ggtttgcacg | ccggtgcaca | 1680 |
| cctgagcctc | agcgactctg | gacagccatt | tgcaacaggg | acctcctgtc | ggtactggag | 1740 |
| gcctttgcca | atgggcagga | ctttggacag | ccgctgccsg | ggcctgatgc | acaggcacct | 1800 |
| gaagaactcg | tcttgcattt | ggctgtcaaa | gtcgccaacc | aggcttccct | gcctctggtg | 1860 |
| gatttcatca | tccagaacgg | tggtcacctg | gatgccaagg | ctgctgacgg | gaacacggct | 1920 |
| ctgcactacg | cagcactcta | caaccagccc | gactgcctca | agctgctgct | gaaggggaga | 1980 |
| gctttggttg | gcacagtaaa | tgaagcaggc | gagacagctc | tggacatagc | caggaagaag | 2040 |
| caccacaagg | agtgtgagga | gctgctggag | caggcccagg | cggggaccTt | tgccttccct | 2100 |
| ctacatgtgg | actactccgt | ggtaatttcc | acagagcctg | gctctgacag | tgaggaggat | 2160 |
| gaggaagaga | agcgctgctt | gctgaggctc | ccggcccagg | ctcactgggc | cagtgggagg | 2220 |
| ctggacatca | gcaacaagac | ctatgagact | gtcgccagcc | tgggagcagc | caccccctcag | 2280 |
| ggcgagagtg | aggactgtcc | cccgcccttg | ccagtcaaaa | actcttctcg | gactttggtc | 2340 |
| caagggtgtg | caagacatgc | cagtggagat | cgttctgaag | tctccagcct | gagttcagag | 2400 |
| gcccctgaga | cccctgagag | cctgggcagt | ccagcctcct | cctccagtct | gatgagcccc | 2460 |
| ttggaacctg | gggatcccag | ccaagcccca | cccaactctg | aagagggcct | ccgagagccc | 2520 |
| ccaggcacct | ccagacccag | cctgacatcc | gggaccaccc | cttcggagat | gtacctcccc | 2580 |
| gtcagattca | gctccgagag | cactcgctcc | tatcggcggg | gggcgcggag | ccctgaagat | 2640 |

UNITED STATES PATENT AND TRADEMARK CFFICE
CERTIFICATE CF CCRRECTICN

| | | |
|---|---|---|
| PATENT NC. | : 7,345,156 B2 | Page 4 of 32 |
| APPLICATICN NC. | : 10/490605 | |
| DATED | : March 18, 2008 | |
| INVENTCR(S) | : Nakamura et al. | |

It is certified that error appears in the above-identified patent and that said Letters Patent is hereby corrected as shown below:

| | | | | | | |
|---|---|---|---|---|---|---|
| ggtccctcag | ccaggcagcc | tctgcccaga | aggaacgtgc | cggttggcat | cactgaagga | 2700 |
| gatggctcaa | ggactgggag | tctcccagca | agttctgtgc | aacttttgca | agactagctc | 2760 |
| cttgctggcc | cccacatgcc | ccatgctagg | ccccaatgtt | cagagctggg | acttgagctc | 2820 |
| acaaaactgg | ggagctgaga | catttgttct | cttggatctc | actctctctg | tcccttgtgc | 2880 |
| ctctgtagct | ggccttcttc | ctgccacagg | ccatgcctct | accaaggaca | catggccttt | 2940 |
| ccctgttagg | gctgatggcg | gttctttcct | atctcattac | ccgctagggg | cctgggagcc | 3000 |
| ctgtggctgg | atctgagtgc | tcctgagctg | gcttcagctg | cagaactctc | agtccctcat | 3060 |
| cagatcgaga | ctctatttcc | cccgtcagtc | tgggggcttc | acaagggcag | gagagccctc | 3120 |
| catcactgac | ttccagatca | gggaccctgc | caagtaggga | ctgtcttctc | agccagccat | 3180 |
| ttattagtct | aatattcctt | cactaaattc | caactctatg | tctggacctg | tgttaggcac | 3240 |
| ttcagatacc | acacgagtaa | gacaagggcc | ctgcaggggt | ggtcctttgg | tggaaagctg | 3300 |
| gtcttaaggg | ttgggcttgg | gaataggcag | ggtcagattc | cagggcatgg | ctctggactc | 3360 |
| agctggttta | tacctatatg | accattacag | ttgtctacag | atcacatcca | ttctggctgg | 3420 |
| tcaacatgca | tgctgtactg | gctgttaaat | aaaaatattc | tgaatgtcac | tccttttgag | 3480 |
| ggacagcaca | gccttcccta | ggcattctcc | tatattcccc | agccaaattg | tagagtcaga | 3540 |
| tgcacccaca | tttgcctgtg | tccttgattt | agcaggaagg | aaaggaatag | tcggggttga | 3600 |
| tggatgccca | cttctcttct | ctttctcttg | gtcaactcag | gagccttta | gtctgaggga | 3660 |
| atggagaggc | aaagaaagaa | gggagagtaa | tagaattggg | agggcagaga | cttaagggtt | 3720 |
| ctgcttccca | gccctagaaa | ttctatcatt | gctcagcccc | aatgagaaag | cagatacacc | 3780 |
| taagccatca | tcaaccacta | acatctcaac | ttgccagttg | ctgggtgctg | ggccctggca | 3840 |

UNITED STATES PATENT AND TRADEMARK CFFICE
CERTIFICATE CF CCRRECTICN

PATENT NC.         : 7,345,156 B2                            Page 5 of 32
APPLICATICN NC.    : 10/490605
DATED              : March 18, 2008
INVENTCR(S)        : Nakamura et al.

It is certified that error appears in the above-identified patent and that said Letters Patent is hereby corrected as shown below:

| | | | | | |
|---|---|---|---|---|---|
| ggaatgggcc | aagccaagca | ggggagacta | gagagcacca | atggccaaca | cagctgcctg    3900 |
| gctggggagg | ctgtgctgtt | tccccggag  | acctgactgg | tctgtggttc | ccacaggaac    3960 |
| agggttgtct | tttgagcccc | cagtgtctgg | tttcattcat | ctcagacttg | ttatttcact    4020 |
| catctctaat | aaaggattgg | ggggtcagtt | | |              4050 |

<210> 2
<211> 903
<212> PRT
<213> Homo sapiens

<400> 2
Met Pro Glu Gln Phe Ser Val Ala Glu Phe Leu Ala Val Thr Ala Glu
1               5                   10                  15

Asp Leu Ser Ser Pro Ala Gly Ala Ala Ala Phe Ala Ala Lys Met Pro
            20                  25                  30

Arg Tyr Arg Gly Ala Ala Leu Ala Arg Glu Glu Ile Leu Glu Gly Asp
        35                  40                  45

Gln Ala Ile Leu Gln Arg Ile Lys Lys Ala Val Arg Ala Ile His Ser
    50                  55                  60

Ser Gly Leu Gly His Val Glu Asn Glu Glu Gln Tyr Arg Glu Ala Val
65                  70                  75                  80

Glu Ser Leu Gly Asn Ser His Leu Ser Gln Asn Ser His Glu Leu Ser
                85                  90                  95

Thr Gly Phe Leu Asn Leu Ala Val Phe Thr Arg Glu Val Ala Ala Leu
            100                 105                 110

Phe Lys Asn Leu Ile Gln Asn Leu Asn Asn Ile Val Ser Phe Pro Leu
        115                 120                 125

Asp Ser Leu Met Lys Gly Gln Leu Arg Asp Gly Arg Gln Asp Ser Lys
    130                 135                 140

UNITED STATES PATENT AND TRADEMARK OFFICE
CERTIFICATE OF CORRECTION

PATENT NO. : 7,345,156 B2  Page 6 of 32
APPLICATION NO. : 10/490605
DATED : March 18, 2008
INVENTOR(S) : Nakamura et al.

It is certified that error appears in the above-identified patent and that said Letters Patent is hereby corrected as shown below:

```
Lys Gln Leu Glu Lys Ala Trp Lys Asp Tyr Glu Ala Lys Met Ala Lys
145                 150                 155                 160

Leu Glu Lys Glu Arg Asp Arg Ala Arg Val Thr Gly Gly Ile Pro Gly
            165                 170                 175

Glu Val Ala Gln Asp Met Gln Arg Glu Arg Arg Ile Phe Gln Leu His
        180                 185                 190

Met Cys Glu Tyr Leu Leu Lys Ala Gly Glu Ser Gln Met Lys Gln Gly
        195                 200                 205

Pro Asp Phe Leu Gln Ser Leu Ile Lys Phe Phe His Ala Gln His Asn
    210                 215                 220

Phe Phe Gln Asp Gly Trp Lys Ala Ala Gln Ser Leu Phe Pro Phe Ile
225                 230                 235                 240

Glu Lys Leu Ala Ala Ser Val His Ala Leu His Gln Ala Gln Glu Asp
            245                 250                 255

Glu Leu Gln Lys Leu Thr Gln Leu Arg Asp Ser Leu Arg Gly Thr Leu
            260                 265                 270

Gln Leu Glu Ser Arg Glu Glu His Leu Ser Arg Lys Asn Ser Gly Cys
            275                 280                 285

Gly Tyr Ser Ile His Gln His Gln Gly Asn Lys Gln Phe Gly Thr Glu
        290                 295                 300

Lys Val Gly Phe Leu Tyr Lys Lys Ser Asp Gly Ile Arg Arg Val Trp
305                 310                 315                 320

Gln Lys Arg Lys Cys Gly Val Lys Tyr Gly Cys Leu Thr Ile Ser His
                325                 330                 335

Ser Thr Ile Asn Arg Pro Pro Val Lys Leu Thr Leu Leu Thr Cys Gln
            340                 345                 350
```

UNITED STATES PATENT AND TRADEMARK OFFICE
CERTIFICATE OF CORRECTION

PATENT NO. : 7,345,156 B2
APPLICATION NO. : 10/490605
DATED : March 18, 2008
INVENTOR(S) : Nakamura et al.

It is certified that error appears in the above-identified patent and that said Letters Patent is hereby corrected as shown below:

Val Arg Pro Asn Pro Glu Glu Lys Lys Cys Phe Asp Leu Val Thr His
        355                  360                 365

Asn Arg Thr Tyr His Phe Gln Ala Glu Asp Glu His Glu Cys Glu Ala
      370                  375              380

Trp Val Ser Val Leu Gln Asn Ser Lys Asp Glu Ala Leu Ser Ser Ala
    385                  390                395              400

Phe Leu Gly Glu Pro Ser Ala Gly Pro Gly Ser Trp Gly Ser Ala Gly
          405                410              415

His Asp Gly Glu Pro His Asp Leu Thr Lys Leu Leu Ile Ala Glu Val
          420                425              430

Lys Ser Arg Pro Gly Asn Ser Gln Cys Cys Asp Cys Gly Ala Ala Asp
      435                  440              445

Pro Thr Trp Leu Ser Thr Asn Leu Gly Val Leu Thr Cys Ile Gln Cys
      450                  455              460

Ser Gly Val His Arg Glu Leu Gly Val Arg Phe Ser Arg Met Gln Ser
  465                470                475              480

Leu Thr Leu Asp Leu Leu Gly Pro Ser Glu Leu Leu Leu Ala Leu Asn
            485                490              495

Met Gly Asn Thr Ser Phe Asn Glu Val Met Glu Ala Gln Leu Pro Ser
          500                505              510

His Gly Gly Pro Lys Pro Ser Ala Glu Ser Asp Met Gly Thr Arg Arg
        515                520              525

Asp Tyr Ile Met Ala Lys Tyr Val Glu His Arg Phe Ala Arg Arg Cys
      530                535              540

Thr Pro Glu Pro Gln Arg Leu Trp Thr Ala Ile Cys Asn Arg Asp Leu
  545                550                555              560

Leu Ser Val Leu Glu Ala Phe Ala Asn Gly Gln Asp Phe Gly Gln Pro
        565                570              575

UNITED STATES PATENT AND TRADEMARK CFFICE
CERTIFICATE CF CCRRECTICN

PATENT NC.        : 7,345,156 B2
APPLICATICN NC.   : 10/490605
DATED             : March 18, 2008
INVENTCR(S)       : Nakamura et al.

It is certified that error appears in the above-identified patent and that said Letters Patent is hereby corrected as shown below:

Leu Pro Gly Pro Asp Ala Gln Ala Pro Glu Glu Leu Val Leu His Leu
          580              585              590

Ala Val Lys Val Ala Asn Gln Ala Ser Leu Pro Leu Val Asp Phe Ile
       595               600              605

Ile Gln Asn Gly Gly His Leu Asp Ala Lys Ala Ala Asp Gly Asn Thr
       610               615              620

Ala Leu His Tyr Ala Ala Leu Tyr Asn Gln Pro Asp Cys Leu Lys Leu
   625             630              635              640

Leu Leu Lys Gly Arg Ala Leu Val Gly Thr Val Asn Glu Ala Gly Glu
         645               650              655

Thr Ala Leu Asp Ile Ala Arg Lys Lys His His Lys Glu Cys Glu Glu
         660               665              670

Leu Leu Glu Gln Ala Gln Ala Gly Thr Phe Ala Phe Pro Leu His Val
         675               680              685

Asp Tyr Ser Trp Val Ile Ser Thr Glu Pro Gly Ser Asp Ser Glu Glu
      690               695              700

Asp Glu Glu Glu Lys Arg Cys Leu Leu Lys Leu Pro Ala Gln Ala His
   705              710              715              720

Trp Ala Ser Gly Arg Leu Asp Ile Ser Asn Lys Thr Tyr Glu Thr Val
          725              730              735

Ala Ser Leu Gly Ala Ala Thr Pro Gln Gly Glu Ser Glu Asp Cys Pro
        740              745              750

Pro Pro Leu Pro Val Lys Asn Ser Ser Arg Thr Leu Val Gln Gly Cys
        755              760              765

Ala Arg His Ala Ser Gly Asp Arg Ser Glu Val Ser Ser Leu Ser Ser
      770              775              780

UNITED STATES PATENT AND TRADEMARK CFFICE
CERTIFICATE CF CCRRECTICN

PATENT NC. : 7,345,156 B2
APPLICATICN NC. : 10/490605
DATED : March 18, 2008
INVENTCR(S) : Nakamura et al.

Page 9 of 32

It is certified that error appears in the above-identified patent and that said Letters Patent is hereby corrected as shown below:

Glu Ala Pro Glu Thr Pro Glu Ser Leu Gly Ser Pro Ala Ser Ser Ser
    785                  790                  795                  800

Ser Leu Met Ser Pro Leu Glu Pro Gly Asp Pro Ser Gln Ala Pro Pro
                  805                  810                  815

Asn Ser Glu Glu Gly Leu Arg Glu Pro Pro Gly Thr Ser Arg Pro Ser
                  820                  825                  830

Leu Thr Ser Gly Thr Thr Pro Ser Glu Met Tyr Leu Pro Val Arg Phe
                  835                  840                  845

Ser Ser Glu Ser Thr Arg Ser Tyr Arg Arg Gly Ala Arg Ser Pro Glu
            850                  855                  860

Asp Gly Pro Ser Ala Arg Gln Pro Leu Pro Arg Arg Asn Val Pro Val
    865                  870                  875                  880

Gly Ile Thr Glu Gly Asp Gly Ser Arg Thr Gly Ser Leu Pro Ala Ser
                  885                  890                  895

Ser Val Gln Leu Leu Gln Asp
                  900

<210> 3
<211> 1879
<212> DNA
<213> Homo Sapiens

<400> 3

| ctcgctcaca | aaaaattgag | ccggccctgg | aggcctgggg | ggcgagtccg | gttgcgcctc | 60 |
| ggagagcgca | acaggcagaa | tttgttcctg | ttgaagagtg | gctcctcttc | taatttccag | 120 |
| actccttgag | gttttaggag | tctggtaggt | gaaattttct | acctctaagg | agaaacagta | 180 |
| cctgctcctt | cctcaagcgc | aagccctcca | ttgctatgga | taccgaatcc | acttattctg | 240 |
| gatattctta | ctattcaagt | cattcgaaaa | aatctcacag | acaaggggaa | agaactagag | 300 |
| agagacacaa | gtcaccccgg | aataaagacg | gcagagggtc | agaaaagtct | gtcaccattc | 360 |

UNITED STATES PATENT AND TRADEMARK OFFICE
CERTIFICATE OF CORRECTION

| | |
|---|---|
| PATENT NO. | : 7,345,156 B2 |
| APPLICATION NO. | : 10/490605 |
| DATED | : March 18, 2008 |
| INVENTOR(S) | : Nakamura et al. |

Page 10 of 32

It is certified that error appears in the above-identified patent and that said Letters Patent is hereby corrected as shown below:

| | | | | | | |
|---|---|---|---|---|---|---|
| aacctcccac | tggagagccc | ctgttgggaa | atgattctac | tcggacagag | gaagttcagg | 420 |
| atgacaactg | gggagagacc | accacggcca | tcacaggcac | ctcggagcac | agcatatccc | 480 |
| aagaggacat | tgccaggatc | agcaaggaca | tggaggacag | cgtggggctg | gattgcaaac | 540 |
| gctacctggg | cctcaccgtc | gcctcttttc | ttggacttct | agttttcctc | acccctattg | 600 |
| ccttcatcct | tttacctccg | atcctgtgga | gggatgagct | ggagccttgt | ggcacaattt | 660 |
| gtgaggggct | ctttatctcc | atggcattca | aactcctcat | tctgctcata | gggacctggg | 720 |
| cacttttttt | ccgcaagcgg | agagctgaca | tgccacgggt | gtttgtgttt | cgtgcccttt | 780 |
| tgttggtcct | catctttctc | tttgtggttt | cctattggct | tttttacggg | gtccgcattt | 840 |
| tggactctcg | ggaccggaat | taccagggca | ttgtgcaata | tgcagtctcc | cttgtggatg | 900 |
| ccctcctctt | catccattac | ctggccatcg | tcctgctgga | gctcaggcag | ctgcagccca | 960 |
| acctgagtat | ccagcgagca | gcattggtgg | tcctagaaaa | ttactacaaa | gatttcacaa | 1080 |
| tctataaccc | aaacctccta | acagcctcca | aattccgagc | agccaagcat | atggccgggc | 1140 |
| tgaaagtcta | caatgtagat | ggccccagta | acaatgccac | tggccagtcc | cgggccatga | 1200 |
| ttgctgcagc | tgctcggcgc | agggactcaa | gccacaacga | gttgtattat | gaagaggccg | 1260 |
| aacatgaacg | gcgagtaaag | aagcggaaag | caaggctggt | ggttgcagtg | gaagaggcct | 1320 |
| tcatccacat | tcagcgtctc | caggctgagg | agcagcagaa | agccccaggg | gaggtgatgg | 1380 |
| accctaggga | ggccgcccag | gccattttcc | cctccatggc | cagggctctc | cagaagtacc | 1440 |
| tgcgcatcac | ccggcagcag | aactaccaca | gcatggagag | catcctgcag | cacctggcct | 1500 |
| tctgcatcac | caacggcatg | accccaagg | ccttcctaga | acggtacctc | agtgcgggcc | 1560 |

UNITED STATES PATENT AND TRADEMARK OFFICE
CERTIFICATE OF CORRECTION

PATENT NO. : 7,345,156 B2
APPLICATION NO. : 10/490605
DATED : March 18, 2008
INVENTOR(S) : Nakamura et al.

It is certified that error appears in the above-identified patent and that said Letters Patent is hereby corrected as shown below:

| | | | | | | |
|---|---|---|---|---|---|---|
| ccaccctgca | atatgacaag | gaccgctggc | tctctacaca | gtggaggctt | gtcagtgatg | 1620 |
| aggctgtgac | taatggatta | cgggatggaa | ttgtgttcgt | ccttaagtgc | ttggacttca | 1680 |
| gcctcgtagt | caatgtgaag | aaaattccat | tcatcatact | ctctgaagag | ttcatagacc | 1740 |
| ccaaatctca | caaatttgtc | cttcgcttac | agtctgagac | atccgtttaa | aagttctata | 1800 |
| tttgtggctt | tattaaaaaa | aaaagaaaaa | tatatagaga | gatatgcaaa | aaaaataaaa | 1860 |
| gacaaaaaca | aaaaaaaaa | | | | | 1879 |

<210> 4
<211> 524
<212> PRT
<213> Homo sapiens

<400> 4
Met Asp Thr Glu Ser Thr Tyr Ser Gly Tyr Ser Tyr Tyr Ser Ser His
1               5                   10                  15

Ser Lys Lys Ser His Arg Gln Gly Glu Arg Thr Arg Glu Arg His Lys
            20                  25                  30

Ser Pro Arg Asn Lys Asp Gly Arg Gly Ser Glu Lys Ser Val Thr Ile
        35                  40                  45

Gln Pro Pro Thr Gly Glu Pro Leu Leu Gly Asn Asp Ser Thr Arg Thr
    50                  55                  60

Glu Glu Val Gln Asp Asp Asn Trp Gly Glu Thr Thr Thr Ala Ile Thr
65              70                  75                  80

Gly Thr Ser Glu His Ser Ile Ser Gln Glu Asp Ile Ala Arg Ile Ser
            85                  90                  95

Lys Asp Met Glu Asp Ser Val Gly Leu Asp Cys Lys Arg Tyr Leu Gly
            100                 105                 110

Leu Thr Val Ala Ser Phe Leu Gly Leu Leu Val Phe Leu Thr Pro Ile
        115                 120                 125

UNITED STATES PATENT AND TRADEMARK OFFICE
CERTIFICATE OF CORRECTION

PATENT NO. : 7,345,156 B2
APPLICATION NO. : 10/490605
DATED : March 18, 2008
INVENTOR(S) : Nakamura et al.

It is certified that error appears in the above-identified patent and that said Letters Patent is hereby corrected as shown below:

Ala Phe Ile Leu Leu Pro Pro Ile Leu Trp Arg Asp Glu Leu Glu Pro
      130                   135                   140

Cys Gly Thr Ile Cys Glu Gly Leu Phe Ile Ser Met Ala Phe Lys Leu
    145                  150                 155              160

Leu Ile Leu Leu Ile Gly Thr Trp Ala Leu Phe Phe Arg Lys Arg Arg
               165                  170                175

Ala Asp Met Pro Arg Val Phe Val Phe Arg Ala Leu Leu Leu Val Leu
        180                  185                190

Ile Phe Leu Phe Val Val Ser Tyr Trp Leu Phe Tyr Gly Val Arg Ile
       195                  200               205

Leu Asp Ser Arg Asp Arg Asn Tyr Gln Gly Ile Val Gln Tyr Ala Val
      210                 215                220

Ser Leu Val Asp Ala Leu Leu Phe Ile His Tyr Leu Ala Ile Val Leu
    225                  230               235           240

Leu Glu Leu Arg Gln Leu Gln Pro Met Phe Thr Leu Gln Val Val Arg
         245                 250               255

Ser Thr Asp Gly Glu Ser Arg Phe Tyr Ser Leu Gly His Leu Ser Ile
          260                265               270

Gln Arg Ala Ala Leu Val Val Leu Glu Asn Tyr Tyr Lys Asp Phe Thr
      275                 280                285

Ile Tyr Asn Pro Asn Leu Leu Thr Ala Ser Lys Phe Arg Ala Ala Lys
    290                  295                300

His Met Ala Gly Leu Lys Val Tyr Asn Val Asp Gly Pro Ser Asn Asn
    305                  310               315           320

Ala Thr Gly Gln Ser Arg Ala Met Ile Ala Ala Ala Ala Arg Arg Arg
         325                 330               335

Asp Ser Ser His Asn Glu Leu Tyr Tyr Glu Glu Ala Glu His Glu Arg
      340                 345                350

UNITED STATES PATENT AND TRADEMARK OFFICE
CERTIFICATE OF CORRECTION

PATENT NO. : 7,345,156 B2
APPLICATION NO. : 10/490605
DATED : March 18, 2008
INVENTOR(S) : Nakamura et al.

It is certified that error appears in the above-identified patent and that said Letters Patent is hereby corrected as shown below:

```
Arg Val Lys Lys Arg Lys Ala Arg Leu Val Val Ala Val Glu Glu Ala
    355                 360                 365

Phe Ile His Ile Gln Arg Leu Gln Ala Glu Glu Gln Gln Lys Ala Pro
    370                 375                 380

Gly Glu Val Met Asp Pro Arg Glu Ala Ala Gln Ala Ile Phe Pro Ser
385                 390                 395                 400

Met Ala Arg Ala Leu Gln Lys Tyr Leu Arg Ile Thr Arg Gln Gln Asn
            405                 410                 415

Tyr His Ser Met Glu Ser Ile Leu Gln His Leu Ala Phe Cys Ile Thr
            420                 425                 430

Asn Gly Met Thr Pro Lys Ala Phe Leu Glu Arg Tyr Leu Ser Ala Gly
            435                 440                 445

Pro Thr Leu Gln Tyr Asp Lys Asp Arg Trp Leu Ser Thr Gln Trp Arg
        450                 455                 460

Leu Val Ser Asp Glu Ala Val Thr Asn Gly Leu Arg Asp Gly Ile Val
465                 470                 475                 480

Phe Val Leu Lys Cys Leu Asp Phe Ser Leu Val Val Asn Val Lys Lys
            485                 490                 495

Ile Pro Phe Ile Ile Leu Ser Glu Glu Phe Ile Asp Pro Lys Ser His
            500                 505                 510

Lys Phe Val Leu Arg Leu Gln Ser Glu Thr Ser Val
        515                 520
```

<210> 5
<211> 2336
<212> DNA
<213> Homo sapiens

<400> 5
ggcacgagga agaatcagga gcttaggatg tattaacacc aactcattaa tatactaacc        60

UNITED STATES PATENT AND TRADEMARK OFFICE
CERTIFICATE OF CORRECTION

PATENT NO. : 7,345,156 B2
APPLICATION NO. : 10/490605
DATED : March 18, 2008
INVENTOR(S) : Nakamura et al.

It is certified that error appears in the above-identified patent and that said Letters Patent is hereby corrected as shown below:

| | | | | | | |
|---|---|---|---|---|---|---|
| ggacaatgtt | ctacaaacaa | ttctacattg | taaaggactg | gattggcaca | aaataaaata | 120 |
| attttatttt | attcagctta | taatatgact | cgatggagga | aaatttgata | agcatgagag | 180 |
| aagaccattc | ttttcatgtt | cgttacagaa | tggaagcttc | ttgcctagag | ctggccttgg | 240 |
| aaggggaacg | tctatgtaaa | tcaggagact | gccgcgctgg | cgtgtcattc | tttgaagctg | 300 |
| cagttcaagt | tggaactgaa | gacctaaaaa | cacttagcgc | tatttacagc | cagttgggca | 360 |
| atgcttattt | ctatttgcat | gattatgcca | aagcattaga | atatcaccat | catgatttaa | 420 |
| cccttgcaag | gactattgga | gaccagctgg | gggaagcgaa | agctagtggt | aatctgggaa | 480 |
| acaccttaaa | agttcttggg | aattttgacg | aagccatagt | ttgttgtcag | cgacacctag | 540 |
| atatttccag | agagcttaat | gacaaggtgg | gagaagcaag | agcactttac | aatcttggga | 600 |
| atgtgtatca | tgccaagggg | aaaagttttg | gttgccctgg | tccccaggat | gtaggagaat | 660 |
| ttccagaaga | agtgagagat | gctctgcagg | cagccgtgga | tttttatgag | gaaaacctat | 720 |
| cattagtgac | tgctttgggt | gaccgagcgg | cacaaggacg | tgcctttgga | aatcttggaa | 780 |
| acacacatta | cctccttggc | aacttcaggg | atgcagttat | agctcatgag | cagcgtctcc | 840 |
| ttattgcaaa | agaatttgga | gataaagcag | ctgaaagaag | agcatatagc | aaccttggaa | 900 |
| atgcatatat | atttcttggt | gaatttgaaa | ctgcctcgga | atactacaag | aagacactac | 960 |
| tgttggcccg | acagcttaaa | gaccgagctg | tagaagcaca | gtcttgttac | agtcttggaa | 1020 |
| atacatatac | tttacttcaa | gactatgaaa | aggccattga | ttatcatctg | aagcacttag | 1080 |
| caattgctca | agagctgaat | gatagaattg | gtgaaggaag | agcatgttgg | agcttaggaa | 1140 |
| atgcatacac | agcactagga | aatcatgatc | aagcaatgca | ttttgctgaa | aagcacttgg | 1200 |
| aaatttcaag | agaggttggg | gataaaagtg | gtgaactaac | agcacgactt | aatctctcag | 1260 |

UNITED STATES PATENT AND TRADEMARK CFFICE
CERTIFICATE CF CCRRECTICN

| | |
|---|---|
| PATENT NC. | : 7,345,156 B2 |
| APPLICATICN NC. | : 10/490605 |
| DATED | : March 18, 2008 |
| INVENTCR(S) | : Nakamura et al. |

Page 15 of 32

It is certified that error appears in the above-identified patent and that said Letters Patent is hereby corrected as shown below:

| | | | | | | |
|---|---|---|---|---|---|---|
| accttcaaat | ggttcttggt | ctgagctaca | gcacaaataa | ctccataatg | tctgaaaata | 1320 |
| ctgaaattga | tagcagtttg | aatggtgtac | tccccaagtt | gggacgccgg | catagtatgg | 1380 |
| aaaatatgga | acttatgaag | ttaacaccag | aaaaggtaca | gaactggaac | agtgaaattc | 1440 |
| ttgctaagca | aaaacctctt | attgccaaac | cttctgcaaa | gctactcttt | gtcaacagac | 1500 |
| tgaaggggaa | aaaatacaaa | acgaattcct | ccactaaagt | tctccaagat | gccagtaatt | 1560 |
| ctattgacca | ccgaattcca | aattctcaga | ggaaaatcag | tgcagatact | attggagatg | 1620 |
| aagggttctt | tgacttatta | agccgatttc | aaagcaatag | gatggatgat | cagagatgtt | 1680 |
| gcttacaaga | aaagaactgc | catacagctt | caacaacaac | ttcttccact | cccccctaaaa | 1740 |
| tgatgctaaa | aacatcatct | gttcctgtgg | tatcccccaa | cacggatgag | tttttagatc | 1800 |
| ttcttgccag | ctcacagagt | cgccgtctgg | atgaccagag | ggctagtttc | agtaatttgc | 1860 |
| cagggcttcg | tctaacacaa | aacagccagt | cggtacttag | ccacctgatg | actaatgaca | 1920 |
| acaaagaggc | tgatgaagat | ttctttgaca | tccttgtaaa | atgtcaagga | tccagattag | 1980 |
| atgatcaaag | atgtgctcca | ccacctgcta | ccacaaaggg | tccgacagta | ccagatgaag | 2040 |
| actttttcag | ccttatttta | cggtcccagg | gaaagagaat | ggatgaacag | agagttcttt | 2100 |
| tacaaagaga | tcaaaacaga | gacactgact | ttgggctaaa | ggacttttttg | caaaataatg | 2160 |
| ctttgttgga | gtttaaaaat | tcagggaaaa | aatcggcaga | ccattagtta | ctatggattt | 2220 |
| attttttttc | ctttcaaaca | cggtaaggaa | acaatctatt | acttttttcc | ttaaaaggag | 2280 |
| aatttatagc | actgtaatac | agcttaaaat | attttagaa | tgatgtaaat | agttaa | 2336 |

<210> 6
<211> 677
<212> PRT
<213> Homo sapiens

UNITED STATES PATENT AND TRADEMARK OFFICE
CERTIFICATE OF CORRECTION

PATENT NO. : 7,345,156 B2
APPLICATION NO. : 10/490605
DATED : March 18, 2008
INVENTOR(S) : Nakamura et al.

It is certified that error appears in the above-identified patent and that said Letters Patent is hereby corrected as shown below:

<400> 6
Met Arg Glu Asp His Ser Phe His Val Arg Tyr Arg Met Glu Ala Ser
1               5                   10                  15

Cys Leu Glu Leu Ala Leu Glu Gly Glu Arg Leu Cys Lys Ser Gly Asp
            20                  25                  30

Cys Arg Ala Gly Val Ser Phe Phe Glu Ala Ala Val Gln Val Gly Thr
        35                  40                  45

Glu Asp Leu Lys Thr Leu Ser Ala Ile Tyr Ser Gln Leu Gly Asn Ala
    50                  55                  60

Tyr Phe Tyr Leu His Asp Tyr Ala Lys Ala Leu Glu Tyr His His His
65                  70                  75                  80

Asp Leu Thr Leu Ala Arg Thr Ile Gly Asp Gln Leu Gly Glu Ala Lys
            85                  90                  95

Ala Ser Gly Asn Leu Gly Asn Thr Leu Lys Val Leu Gly Asn Phe Asp
            100                 105                 110

Glu Ala Ile Val Cys Cys Gln Arg His Leu Asp Ile Ser Arg Glu Leu
        115                 120                 125

Asn Asp Lys Val Gly Glu Ala Arg Ala Leu Tyr Asn Leu Gly Asn Val
    130                 135                 140

Tyr His Ala Lys Gly Lys Ser Phe Gly Cys Pro Gly Pro Gln Asp Val
145                 150                 155                 160

Gly Glu Phe Pro Glu Glu Val Arg Asp Ala Leu Gln Ala Ala Val Asp
            165                 170                 175

Phe Tyr Glu Glu Asn Leu Ser Leu Val Thr Ala Leu Gly Asp Arg Ala
            180                 185                 190

Ala Gln Gly Arg Ala Phe Gly Asn Leu Gly Asn Thr His Tyr Leu Leu
            195                 200                 205

UNITED STATES PATENT AND TRADEMARK CFFICE
CERTIFICATE CF CCRRECTICN

PATENT NC.      : 7,345,156 B2
APPLICATICN NC. : 10/490605
DATED           : March 18, 2008
INVENTCR(S)     : Nakamura et al.

It is certified that error appears in the above-identified patent and that said Letters Patent is hereby corrected as shown below:

Gly Asn Phe Arg Asp Ala Val Ile Ala His Glu Gln Arg Leu Leu Ile
        210                        215                    220

Ala Lys Glu Phe Gly Asp Lys Ala Ala Glu Arg Arg Ala Tyr Ser Asn
    225                      230                    235                    240

Leu Gly Asn Ala Tyr Ile Phe Leu Gly Glu Phe Glu Thr Ala Ser Glu
                245                    250                    255

Tyr Tyr Lys Lys Thr Leu Leu Leu Ala Arg Gln Leu Lys Asp Arg Ala
        260                    265                    270

Val Glu Ala Gln Ser Cys Tyr Ser Leu Gly Asn Thr Tyr Thr Leu Leu
       275                    280                    285

Gln Asp Tyr Glu Lys Ala Ile Asp Tyr His Leu Lys His Leu Ala Ile
        290                    295                    300

Ala Gln Glu Leu Asn Asp Arg Ile Gly Glu Gly Arg Ala Cys Trp Ser
    305                      310                    315                  320

Leu Gly Asn Ala Tyr Thr Ala Leu Gly Asn His Asp Gln Ala Met His
                325                    330                    335

Phe Ala Glu Lys His Leu Glu Ile Ser Arg Glu Val Gly Asp Lys Ser
                340                    345                    350

Gly Glu Leu Thr Ala Arg Leu Asn Leu Ser Asp Leu Gln Met Val Leu
                355                    360                    365

Gly Leu Ser Tyr Ser Thr Asn Asn Ser Ile Met Ser Glu Asn Thr Glu
       370                    375                    380

Ile Asp Ser Ser Leu Asn Gly Val Leu Pro Lys Leu Gly Arg Arg His
    385                      390                    395                  400

Ser Met Glu Asn Met Glu Leu Met Lys Leu Thr Pro Glu Lys Val Gln
                405                    410                    415

Asn Trp Asn Ser Glu Ile Leu Ala Lys Gln Lys Pro Leu Ile Ala Lys
        420                    425                    430

UNITED STATES PATENT AND TRADEMARK CFFICE
CERTIFICATE CF CCRRECTICN

PATENT NC. : 7,345,156 B2
APPLICATICN NC. : 10/490605
DATED : March 18, 2008
INVENTCR(S) : Nakamura et al.

It is certified that error appears in the above-identified patent and that said Letters Patent is hereby corrected as shown below:

Pro Ser Ala Lys Leu Leu Phe Val Asn Arg Leu Lys Gly Lys Lys Tyr
        435                 440                 445

Lys Thr Asn Ser Ser Thr Lys Val Leu Gln Asp Ala Ser Asn Ser Ile
      450                 455                460

Asp His Arg Ile Pro Asn Ser Gln Arg Lys Ile Ser Ala Asp Thr Ile
  465                470                475               480

Gly Asp Glu Gly Phe Phe Asp Leu Leu Ser Arg Phe Gln Ser Asn Arg
        485                 490                495

Met Asp Asp Gln Arg Cys Cys Leu Gln Glu Lys Asn Cys His Thr Ala
        500                 505                510

Ser Thr Thr Thr Ser Ser Thr Pro Pro Lys Met Met Leu Lys Thr Ser
        515                 520                525

Ser Val Pro Val Val Ser Pro Asn Thr Asp Glu Phe Leu Asp Leu Leu
        530                 535                540

Ala Ser Ser Gln Ser Arg Arg Leu Asp Asp Gln Arg Ala Ser Phe Ser
  545                550                555               560

Asn Leu Pro Gly Leu Arg Leu Thr Gln Asn Ser Gln Ser Val Leu Ser
        565                 570                575

His Leu Met Thr Asn Asp Asn Lys Glu Ala Asp Glu Asp Phe Phe Asp
          580                 585                590

Ile Leu Val Lys Cys Gln Gly Ser Arg Leu Asp Asp Gln Arg Cys Ala
        595                 600                605

Pro Pro Pro Ala Thr Thr Lys Gly Pro Thr Val Pro Asp Glu Asp Phe
      610                 615                620

Phe Ser Leu Ile Leu Arg Ser Gln Gly Lys Arg Met Asp Glu Gln Arg
      625                 630                635              640

UNITED STATES PATENT AND TRADEMARK CFFICE
CERTIFICATE CF CCRRECTICN

| | | |
|---|---|---|
| PATENT NC. | : 7,345,156 B2 | Page 19 of 32 |
| APPLICATICN NC. | : 10/490605 | |
| DATED | : March 18, 2008 | |
| INVENTCR(S) | : Nakamura et al. | |

It is certified that error appears in the above-identified patent and that said Letters Patent is hereby corrected as shown below:

Val Leu Leu Gln Arg Asp Gln Asn Arg Asp Thr Asp Phe Gly Leu Lys
        645       650       655

Asp Phe Leu Gln Asn Asn Ala Leu Leu Glu Phe Lys Asn Ser Gly Lys
      660       665       670

Lys Ser Ala Asp His
     675

<210> 7
<211> 22
<212> DNA
<213> Artificial

<220>
<223> an artificially synthesized primer sequence

<400> 7
acaacagcct caagatcatc ag                22

<210> 8
<211> 20
<212> DNA
<213> Artificial

<220>
<223> an artificially synthesized primer sequence

<400> 8
ggtccaccac tgacacgttg                20

<210> 9
<211> 22
<212> DNA
<213> Artificial

<220>
<223> an artificially synthesized primer sequence

<400> 9
agctgagaca tttgttctct tg                22

UNITED STATES PATENT AND TRADEMARK OFFICE
CERTIFICATE OF CORRECTION

PATENT NO.      : 7,345,156 B2
APPLICATION NO. : 10/490605
DATED           : March 18, 2008
INVENTOR(S)     : Nakamura et al.

It is certified that error appears in the above-identified patent and that said Letters Patent is hereby corrected as shown below:

<210>  10
<211>  22
<212>  DNA
<213>  Artificial

<220>
<223>  an artificially synthesized primer sequence

<400>  10
tataaaccag  ctgagtccag  ag                                            22

<210>  11
<211>  22
<212>  DNA
<213>  Artificial

<220>
<223>  an artificially synthesized primer sequence

<400>  11
ctcacttggc  acgtcagcag  gg                                            22

<210>  12
<211>  10
<212>  DNA
<213>  Homo sapiens

<400>  12
cccgccatgc                                                            10

<210>  13
<211>  16
<212>  DNA
<213>  Artificial

<220>
<223>  an artificially synthesized oligonucleotide sequence

<400>  13
tgctccggca  tggcgg                                                    16

UNITED STATES PATENT AND TRADEMARK OFFICE
CERTIFICATE OF CORRECTION

| | | |
|---|---|---|
| PATENT NO. | : 7,345,156 B2 | |
| APPLICATION NO. | : 10/490605 | |
| DATED | : March 18, 2008 | |
| INVENTOR(S) | : Nakamura et al. | |

It is certified that error appears in the above-identified patent and that said Letters Patent is hereby corrected as shown below:

At Column 22, line 58, please delete the Sequence Listing which continues through Column 54 and replace it with the following:

<210> 14
<211> 16
<212> DNA
<213> Artificial

<220>
<223> an artificially synthesized oligonucleotide sequence

<400> 14
gctgaactgc tccggc     16

<210> 15
<211> 16
<212> DNA
<213> Artificial

<220>
<223> an artificially synthesized oligonucleotide sequence

<400> 15
tccaagatct cctccc     16

<210> 16
<211> 16
<212> DNA
<213> Artificial

<220>
<223> an artificially synthesized oligonucleotide sequence

<400> 16
tctccttcca agatct     16

UNITED STATES PATENT AND TRADEMARK OFFICE
CERTIFICATE OF CORRECTION

| | | |
|---|---|---|
| PATENT NO. | : 7,345,156 B2 | |
| APPLICATION NO. | : 10/490605 | |
| DATED | : March 18, 2008 | |
| INVENTOR(S) | : Nakamura et al. | |

It is certified that error appears in the above-identified patent and that said Letters Patent is hereby corrected as shown below:

At Column 22, line 58, please delete the Sequence Listing which continues through Column 54 and replace it with the following:

<210> 17
<211> 16
<212> DNA
<213> Artificial

<220>
<223> an artificially synthesized oligonucleotide sequence

<400> 17
gcgctgagcc ggcctc                                                     16

<210> 18
<211> 16
<212> DNA
<213> Artificial

<220>
<223> an artificially synthesized oligonucleotide sequence

<400> 18
cctcacctcc tcccgc                                                     16

<210> 19
<211> 16
<212> DNA
<213> Artificial

<220>
<223> an artificially synthesized oligonucleotide sequence

<400> 19
ccgccatgcc ggagca                                                     16

UNITED STATES PATENT AND TRADEMARK CFFICE
CERTIFICATE CF CCRRECTICN

| | | |
|---|---|---|
| PATENT NC. | : 7,345,156 B2 | Page 23 of 32 |
| APPLICATICN NC. | : 10/490605 | |
| DATED | : March 18, 2008 | |
| INVENTCR(S) | : Nakamura et al. | |

It is certified that error appears in the above-identified patent and that said Letters Patent is hereby corrected as shown below:

At Column 22, line 58, please delete the Sequence Listing which continues through Column 54 and replace it with the following:

<210> 20
<211> 16
<212> DNA
<213> Artificial

<220>
<223> an artificially synthesized oligonucleotide sequence

<400> 20
gccggagcag ttcagc                                         16

<210> 21
<211> 16
<212> DNA
<213> Artificial

<220>
<223> an artificially synthesized oligonucleotide sequence

<400> 21
gggaggagat cttgga                                         16

<210> 22
<211> 16
<212> DNA
<213> Artificial

<220>
<223> an artificially synthesized oligonucleotide sequence

<400> 22
agatcttgga aggaga                                         16

UNITED STATES PATENT AND TRADEMARK CFFICE
CERTIFICATE CF CCRRECTICN

PATENT NC. : 7,345,156 B2
APPLICATICN NC. : 10/490605
DATED : March 18, 2008
INVENTCR(S) : Nakamura et al.

It is certified that error appears in the above-identified patent and that said Letters Patent is hereby corrected as shown below:

At Column 22, line 58, please delete the Sequence Listing which continues through Column 54 and replace it with the following:

<210> 23
<211> 16
<212> DNA
<213> Artificial

<220>
<223> an artificially synthesized oligonucleotide sequence

<400> 23
gaggccggct cagcgc            16

<210> 24
<211> 16
<212> DNA
<213> Artificial

<220>
<223> an artificially synthesized oligonucleotide sequence

<400> 24
gcgggaggag gtgagg            16

<210> 25
<211> 23
<212> DNA
<213> Artificial

<220>
<223> an artificially synthesized primer sequence

<400> 25
gagttgtatt atgaagaggc cga            23

UNITED STATES PATENT AND TRADEMARK CFFICE
CERTIFICATE CF CCRRECTICN

| | | |
|---|---|---|
| PATENT NC. | : 7,345,156 B2 | |
| APPLICATICN NC. | : 10/490605 | |
| DATED | : March 18, 2008 | |
| INVENTCR(S) | : Nakamura et al. | |

It is certified that error appears in the above-identified patent and that said Letters Patent is hereby corrected as shown below:

At Column 22, line 58, please delete the Sequence Listing which continues through Column 54 and replace it with the following:

<210> 26
    <211> 23
    <212> DNA
    <213> Artificial

<220>
    <223> an artificially synthesized primer sequence

<400> 26
    atgtctcaga ctgtaagcga agg            23

<210> 27
    <211> 28
    <212> DNA
    <213> Artificial

<220>
    <223> an artificially synthesized primer sequence

<400> 27
    tgtcagctct ccgcttgcgg aaaaaaag        28

<210> 28
    <211> 16
    <212> DNA
    <213> Artificial

<220>
    <223> an artificially synthesized oligonucleotide sequence

<400> 28
    gtatccatag caatgg              16

<210> 29
    <211> 16
    <212> DNA
    <213> Artificial

UNITED STATES PATENT AND TRADEMARK CFFICE
CERTIFICATE CF CCRRECTICN

| | | |
|---|---|---|
| PATENT NC. | : 7,345,156 B2 | |
| APPLICATICN NC. | : 10/490605 | |
| DATED | : March 18, 2008 | |
| INVENTCR(S) | : Nakamura et al. | |

It is certified that error appears in the above-identified patent and that said Letters Patent is hereby corrected as shown below:

At Column 22, line 58, please delete the Sequence Listing which continues through Column 54 and replace it with the following:

<220>
    <223>   an artificially synthesized oligonucleotide sequence

<400>  29
    tggattgggt   atccat                                 16

<210>  30
    <211>  16
    <212>  DNA
    <213>  Artificial

<220>
    <223>   an artificially synthesized oligonucleotide sequence

<400>  30
    taagtggatt   gggtat                                 16

<210>  31
    <211>  16
    <212>  DNA
    <213>  Artificial

<220>
    <223>   an artificially synthesized oligonucleotide sequence

<400>  31
    actcctacct   gcctgt                                 16

<210>  32
    <211>  16
    <212>  DNA
    <213>  Artificial

<220>
    <223>   an artificially synthesized oligonucleotide sequence

<400>  32
    ccattgctat   ggatac                                 16

UNITED STATES PATENT AND TRADEMARK CFFICE
CERTIFICATE CF CCRRECTICN

PATENT NC. : 7,345,156 B2
APPLICATICN NC. : 10/490605
DATED : March 18, 2008
INVENTCR(S) : Nakamura et al.

It is certified that error appears in the above-identified patent and that said Letters Patent is hereby corrected as shown below:

At Column 22, line 58, please delete the Sequence Listing which continues through Column 54 and replace it with the following:

<210> 33
<211> 16
<212> DNA
<213> Artificial

<220>
<223> an artificially synthesized oligonucleotide sequence

<400> 33
atggataccc   aatcca                                                                 16

<210> 34
<211> 16
<212> DNA
<213> Artificial

<220>
<223> an artificially synthesized oligonucleotide soquence

<400> 34
atacccaatc   cactta                                                                 16

<210> 35
<211> 16
<212> DNA
<213> Artificial

<220>
<223> an artificially synthesized oligonucleotide sequence

<400> 35
acaggcaggt   aggagt                                                                 16

UNITED STATES PATENT AND TRADEMARK OFFICE
CERTIFICATE OF CORRECTION

PATENT NO. : 7,345,156 B2
APPLICATION NO. : 10/490605
DATED : March 18, 2008
INVENTOR(S) : Nakamura et al.

It is certified that error appears in the above-identified patent and that said Letters Patent is hereby corrected as shown below:

At Column 22, line 58, please delete the Sequence Listing which continues through Column 54 and replace it with the following:

<210> 36
<211> 22
<212> DNA
<213> Artificial

<220>
<223> an artificially synthesized primer sequence

<400> 36
atctgaagca cttagcaatt gc                                              22

<210> 37
<211> 21
<212> DNA
<213> Artificial

<220>
<223> an artificially synthesized primer sequence

<400> 37
ctgtagctca gaccaagaac c                                               21

<210> 38
<211> 16
<212> DNA
<213> Artificial

<220>
<223> an artificially synthesized oligonucleotide sequence

<400> 38
ccatcgagtc atatta                                                     16

UNITED STATES PATENT AND TRADEMARK CFFICE
CERTIFICATE CF CCRRECTICN

| | | |
|---|---|---|
| PATENT NC. | : 7,345,156 B2 | |
| APPLICATICN NC. | : 10/490605 | |
| DATED | : March 18, 2008 | |
| INVENTCR(S) | : Nakamura et al. | |

It is certified that error appears in the above-identified patent and that said Letters Patent is hereby corrected as shown below:

At Column 22, line 58, please delete the Sequence Listing which continues through Column 54 and replace it with the following:

<210> 39
<211> 16
<212> DNA
<213> Artificial

<220>
<223> an artificially synthesized oligonucleotide sequence

<400> 39
ttcctccatc gagtca            16

<210> 40
<211> 16
<212> DNA
<213> Artificial

<220>
<223> an artificially synthesized oligonucleotide sequenece

<400> 40
aaattttcct ccatcg            16

<210> 41
<211> 16
<212> DNA
<213> Artificial

<220>
<223> an artificially synthesized oligonucleotide sequence

<400> 41
agtcttacct gtaacg            16

<210> 42
<211> 16
<212> DNA
<213> Artificial

UNITED STATES PATENT AND TRADEMARK CFFICE
CERTIFICATE CF CCRRECTICN

| | | |
|---|---|---|
| PATENT NC. | : 7,345,156 B2 | |
| APPLICATICN NC. | : 10/490605 | |
| DATED | : March 18, 2008 | |
| INVENTCR(S) | : Nakamura et al. | |

It is certified that error appears in the above-identified patent and that said Letters Patent is hereby corrected as shown below:

At Column 22, line 58, please delete the Sequence Listing which continues through Column 54 and replace it with the following:

<220>
<223>  an artificially synthesized oligonucleotide sequence

<400>  42
gcttccattc   tacaaa                                                                16

<210>  43
<211>  16
<212>  DNA
<213>  Artificial

<220>
<223>  an artificially synthesized oligonucleotide sequence

<400>  43
taatatgact   cgatgg                                                                16

<210>  44
<211>  16
<212>  DNA
<213>  Artificial

<220>
<223>  an artificially synthesized oligonucleotide sequence

<400>  44
tgactcgatg   gaggaa                                                                16

<210>  45
<211>  16
<212>  DNA
<213>  Artificial

<220>
<223>  an artificially synthesized oligonucleotide sequence

<400>  45
cgatggagga   aaattt                                                                16

UNITED STATES PATENT AND TRADEMARK OFFICE
CERTIFICATE OF CORRECTION

PATENT NO. : 7,345,156 B2
APPLICATION NO. : 10/490605
DATED : March 18, 2008
INVENTOR(S) : Nakamura et al.

It is certified that error appears in the above-identified patent and that said Letters Patent is hereby corrected as shown below:

At Column 22, line 58, please delete the Sequence Listing which continues through Column 54 and replace it with the following:

<210> 46
<211> 16
<212> DNA
<213> Artificial

<220>
<223> an artificially synthesized oligonucleotide sequence

<400> 46
cgttacaggt aagact 16

<210> 47
<211> 16
<212> DNA
<213> Artificial

<220>
<223> an artificially synthesized oligonucleotide sequence

<400> 47
tttgtagaat ggaagc 16

<210> 48
<211> 118
<212> PRT
<213> Homo sapiens

<400> 48
Lys Glu Ile Ile Ser Glu Val Gln Arg Met Thr Gly Asn Asp Val Cys
1               5                   10                  15

Cys Asp Cys Gly Ala Pro Asp Pro Thr Trp Leu Ser Thr Asn Leu Gly
            20                  25                  30

Ile Leu Thr Cys Ile Glu Cys Ser Gly Ile His Arg Glu Leu Gly Val
        35                  40                  45

UNITED STATES PATENT AND TRADEMARK CFFICE
CERTIFICATE CF CCRRECTICN

PATENT NC.         : 7,345,156 B2
APPLICATICN NC.    : 10/490605
DATED              : March 18, 2008
INVENTCR(S)        : Nakamura et al.

It is certified that error appears in the above-identified patent and that said Letters Patent is hereby corrected as shown below:

At Column 22, line 58, please delete the Sequence Listing which continues through Column 54 and replace it with the following:

His Tyr Ser Arg Met Gln Ser Leu Thr Leu Asp Val Leu Gly Thr Ser
    50                  55                  60

Glu Leu Leu Leu Ala Lys Asn Ile Gly Asn Ala Gly Phe Asn Glu Ile
65                  70                  75                  80

Met Glu Cys Cys Leu Pro Ala Glu Asp Ser Val Lys Pro Asn Pro Gly
                85                  90                  95

Ser Asp Met Asn Ala Arg Lys Asp Tyr Ile Thr Ala Lys Tyr Ile Glu
            100                 105                 110

Arg Arg Tyr Ala Arg Lys
        115

Signed and Sealed this

Seventh Day of October, 2008

JON W. DUDAS
*Director of the United States Patent and Trademark Office*